United States Patent
Mitha et al.

(10) Patent No.: US 11,504,254 B2
(45) Date of Patent: Nov. 22, 2022

(54) SYSTEM AND METHODS FOR COMPRESSING ENDOVASCULAR DEVICES

(71) Applicant: FLUID BIOMED INC., Calgary (CA)

(72) Inventors: Alim P. Mitha, Calgary (CA); Mehdi Jamshidi, Calgary (CA)

(73) Assignee: FLUID BIOMED INC., Calgary (CA)

( * ) Notice: Subject to any disclaimer, the term of this patent is extended or adjusted under 35 U.S.C. 154(b) by 0 days.

(21) Appl. No.: 16/810,481

(22) Filed: Mar. 5, 2020

(65) Prior Publication Data
US 2021/0275334 A1 Sep. 9, 2021

(51) Int. Cl.
A61F 2/966 (2013.01)
A61F 2/958 (2013.01)
A61F 2/95 (2013.01)

(52) U.S. Cl.
CPC ............. *A61F 2/966* (2013.01); *A61F 2/958* (2013.01); *A61F 2002/9511* (2013.01); *A61F 2002/9665* (2013.01)

(58) Field of Classification Search
CPC .. A61F 2/966; A61F 2/958; A61F 2002/9665; A61F 2002/9511
See application file for complete search history.

(56) References Cited

U.S. PATENT DOCUMENTS

| | | | |
|---|---|---|---|
| 6,202,272 B1 | 3/2001 | Jackson | |
| 8,151,445 B1 | 4/2012 | Warriner et al. | |
| 8,608,795 B2 | 12/2013 | Melsheimer et al. | |
| 8,753,384 B2 | 6/2014 | Leanna | |
| 9,717,502 B2 | 8/2017 | Teoh et al. | |
| 9,814,466 B2 | 11/2017 | Kadam | |
| 10,182,931 B2 | 1/2019 | Pung et al. | |
| 10,201,444 B2 | 2/2019 | Rusk et al. | |
| 10,292,851 B2 | 5/2019 | Gorochow | |
| 10,405,868 B2 | 9/2019 | Tompkins et al. | |
| 10,555,824 B2 | 2/2020 | Dorn et al. | |
| 2008/0127707 A1 | 6/2008 | Kokish et al. | |
| 2008/0262592 A1* | 10/2008 | Jordan | A61F 2/95 623/1.11 |
| 2009/0192518 A1* | 7/2009 | Golden | A61F 2/966 606/108 |
| 2009/0299449 A1* | 12/2009 | Styrc | A61F 2/966 623/1.11 |
| 2013/0268064 A1* | 10/2013 | Duffy | A61F 2/2436 623/2.11 |
| 2014/0012369 A1 | 1/2014 | Murry, III et al. | |

(Continued)

FOREIGN PATENT DOCUMENTS

WO WO 99/51167 A2 10/1999
WO WO 2017/139421 A1 8/2017

OTHER PUBLICATIONS

Pumar, et al; Preliminary Experience with Leo Self-Expanding Stent for the Treatment of Intracranial Aneurysms; Am J Neuroradiol; Nov.-Dec. 2005; 26:2573-2577.

(Continued)

*Primary Examiner* — Ryan J. Severson
*Assistant Examiner* — Andrew P. Restaino
(74) *Attorney, Agent, or Firm* — Kilpatrick Townsend & Stockton LLP

(57) ABSTRACT

This disclosure relates to systems and methods for compressing reversibly compressible endovascular devices for loading into delivery catheters prior to deployment in lumen of a vessel.

22 Claims, 28 Drawing Sheets

(56) References Cited

U.S. PATENT DOCUMENTS

| | | | | |
|---|---|---|---|---|
| 2016/0166372 A1* | 6/2016 | Villareal | ............. | A61F 2/01 |
| | | | | 606/200 |
| 2016/0250051 A1* | 9/2016 | Lim | ............. | A61F 2/95 |
| | | | | 623/1.11 |
| 2017/0296791 A1 | 10/2017 | Benjamin et al. | | |
| 2017/0348099 A1* | 12/2017 | Mendelson | ............. | A61F 2/95 |
| 2018/0280174 A1* | 10/2018 | Dwork | ............. | A61F 2/966 |
| 2019/0151067 A1* | 5/2019 | Zucker | ............. | A61F 2/82 |

OTHER PUBLICATIONS

ISA, Canadian Intellectual Property Office; International Search Report of PCT/CA2021/050300; dated May 13, 2021; 3 pgs.

* cited by examiner

SYSTEM AND METHODS FOR COMPRESSING ENDOVASCULAR DEVICES

BACKGROUND OF THE INVENTION

1. Field of Invention

This disclosure relates to endovascular devices. In particular, this disclosure relates systems and methods compressing reversibly compressible endovascular devices for loading into delivery catheters prior to deployment in the body.

2. Description of Related Art

An endovascular device (ED) is an implantable medical device, such as a stent, which can be used to treat a variety of vascular conditions. Most typically, an ED is a tubular or cylindrical structure which is surgically inserted into a blood vessel to effect mechanical support for the walls of the vessel, to effect some change in the blood flow such as flow diversion, and/or to deliver therapeutics at the point of deployment within the vessel.

Often, an ED will be resiliently deformable/compressible so that it can be compressed for loading in a delivery catheter, and then be expanded upon deployment into a lumen of a vessel of a patient. Currently, reversibly compressible EDs are compressed or crimped to a significantly smaller diameter than the blood vessel, and provided by manufacturers in a compressed position within a delivery sheath. The compressed ED can then be transferred into a delivery catheter when needed, and advanced through the delivery catheter to the intended location in the patient's blood vessel. The reversibly compressible ED will typically have an elastic bias to have a nominal size compared with the blood vessel when it is in a compressed within the delivery catheter, such that it self-expands to fit the vessel when deployed in situ.

Reversibly compressible EDs are compressed and pre-loaded into a delivery sheath at the site of factory manufacture. The equipment for this compression may be pneumatic compression dies as disclosed in, for example, U.S. Pat. No. 8,151,445 B1, WO 2017/139421, and US20080127707A1. Such equipment is typically large, powered, metal, immobile, and difficult to sterilize. Accordingly, such equipment may be well-suited for use at an ED manufacturing facility, but is generally unsuitable for use at a point of care such as a surgical setting.

Hand-held crimping tools exist and are disclosed in, for example, U.S. Pat. No. 6,202,272 B1. However, such tools are large, heavy, and impractical to provide with every packaged ED. Accordingly, they are not practical to sterilize in the surgical setting.

SUMMARY OF THE INVENTION

The present inventors recognized a need to develop an ED loading system that can be used at the point of care so that reversibly compressible EDs can be packaged and provided by the manufacturer, and stored, in a non-compressed position. Otherwise, EDs that are maintained in a compressed position may suffer from stress relaxation of the materials used to manufacture the ED, which include but are not limited to, non-shape memory metals and polymers. Current EDs do not include a method of crimping the ED in case the ED needs to be packaged in the fully expanded configuration and then crimped at the point of care for immediate delivery into the patient.

The delivery systems disclosed herein can be used for EDs that are provided in a non-compressed configuration, in order to crimp them into a delivery sheath at the point of care or before packaging. It has the advantage of use for laser-cut (either open cell or closed cell designs) as well as for braided stents. It can be used at the point of care for EDs that are required to be delivered in the fully expanded configuration, due to the avoidance of stress relaxation of the stent ED which includes, but are not limited to, non-shape memory metals as well as polymers.

Various aspects of this disclosure relate to a system for the radial compression of a reversibly compressible endovascular device (ED) prior to deployment. The system comprises the ED, wherein the ED comprises a tubular body, wherein the body is expandable between a compressed position and an non-compressed position, the tubular body having an inner surface, an outer surface, and opposed distal and proximal ED openings. The system further comprises a delivery sheath sized to receive and maintain the ED in the compressed position, the delivery sheath having a delivery sheath opening having a width sized to receive the ED into the delivery sheath in a compressed form. The system further comprises a compressor for compressing the ED for reception by the delivery sheath through the delivery sheath opening. The compressor comprises a generally tapered structure defining an interior space, the tapered structure comprising distal and proximal compressor ends, wherein the proximal compressor end is proximal to the delivery sheath opening, wherein the distal compressor end comprises a distal compressor opening sized to receive the ED in the non-compressed position, wherein the tapered structure tapers from the distal compressor opening toward the proximal compressor end such that the cross section of the interior space diminishes toward the proximal compressor end, wherein the cross sectional area of the interior space at the second end is equal to or less than the cross sectional area of the delivery sheath opening. The system further comprises a push wire detachably attached to the ED and disposed within the delivery sheath. The push wire is operable to be advanced proximally through the delivery sheath to urge the ED through the compressor, whereby the ED is deformed into the compressed position as it is urged proximally through the compressor.

In various embodiments, the compressor comprises a second compressor opening at the second compressor end. In various embodiments, the second compressor opening is in communication with the delivery sheath opening. In various embodiments, the width of the second compressor opening is smaller than the radial diameter of the ED when the ED is in the non-compressed position. In various embodiments, the push wire is disposed within the ED through the second compressor opening. In various embodiments, the push wire is operable to be advanced proximally through the delivery sheath to urge the ED through the second compressor opening and into the delivery sheath.

In various embodiments, the compressor is a funnel. In various embodiments, the tapered structure comprises a unitary body.

In various embodiments, the compressor is detachable.

In various embodiments, the compressor is collapsible. In various embodiments, the compressor is reversibly collapsible. In various embodiments, the compressor comprises a braided structure, for example, a braided polypropylene structure. In various embodiments, the compressor comprises a plurality of overlapping tongues coupled at the second compressor end, wherein each tongue tapers toward the second compressor end. In various embodiments, the second compressor end is sized to be received within the delivery sheath through the delivery sheath opening. In various embodiments, the compressor is sized to be received within the delivery sheath when the compressor is in a collapsed position. In various embodiments, an inner wall of the delivery sheath is operable to exert a force against the side of the tapered structure, as the compressor is received within the delivery sheath that is sufficient to collapse the compressor.

In various embodiments, the push wire is attached to the compressor, wherein the compressor is attached to the ED by one or more threads. In various embodiments, the one or more threads are attached to the inner surface of the ED. In various embodiments, the one or more threads are electrolytically detachable from the ED. In various embodiments, the one or more threads are mechanically detachable from the ED. In various embodiments, the one or more threads is a single wire comprising a lasso looped around the tubular body at a proximal end of the ED.

In various embodiments, the push wire is attached to the compressor, wherein an interior surface of the tapered structure is operable to frictionally engage the outer surface of the ED.

In various embodiments, the push wire is operable to be advanced proximally through the delivery sheath to urge the ED and the compressor toward the delivery sheath, whereby collapse of the compressor upon reception within the delivery sheath exerts a radial force upon the ED sufficient to compress the ED for reception in the delivery sheath.

In various embodiments, an interior surface of the tapered structure is operable to frictionally engage the outer surface of the ED.

In various embodiments, the system comprises a hollow compressor wire attached to the compressor and disposed within the delivery sheath. The compressor wire is operable to be advanced through the delivery sheath to urge the compressor through the delivery sheath opening to collapse the compressor, whereby the ED is deformed into the compressed position as the compressor collapses as the ED and the compressor are urged through the delivery sheath opening. In various embodiments, the push wire is disposed within the compressor wire, wherein the push wire is operable to be advanced through the delivery sheath independently of the compressor wire to urge the ED independently of the compressor. In various embodiments, the compressor further comprises a bump member disposed on the push wire between the ED and the compressor, wherein the bump member is for abutting the ED along the circumference of the proximal ED opening to urge the ED distally through the delivery sheath when the push wire is advanced distally through the delivery sheath. In various embodiments, the push wire and compressor wire are operable to be advanced proximally through the delivery sheath to urge the ED and the compressor toward the delivery sheath, whereby collapse of the compressor upon reception within the delivery sheath exerts a radial force upon the ED sufficient to compress the ED for reception in the delivery sheath.

In various embodiments, the ED is a self-expanding ED.

Various aspects of the disclosure relate to a system for deploying a reversibly compressible endovascular device within a lumen of a vessel. The system comprises a system for the radial compression of a reversibly compressible endovascular device (ED) prior to deployment as described above. The system further comprises a delivery catheter comprising proximal and distal delivery catheter openings. The distal delivery catheter opening is for deploying the ED in to the lumen. The proximal delivery catheter opening is for receiving the ED from the delivery sheath. The proximal delivery catheter opening is of a width equal to or greater than the width of the delivery sheath opening. The system further comprises a hub connected to the proximal delivery catheter opening. The hub has a hub opening for receiving the delivery sheath in the hub when the ED is positioned in the delivery sheath, and positioning the delivery sheath in abutment with the proximal delivery catheter opening. The push wire is operable to be advanced through the delivery catheter to urge the ED through the delivery catheter and out distal delivery catheter opening.

In various embodiments, the push wire is operable to be advanced through the delivery catheter to urge the compressor through the delivery catheter and out the distal delivery catheter opening, wherein the compressor is operable to expand.

In various embodiments, the push wire is operable to be retracted toward the hub to urge a deployed ED and expanded compressor toward the distal delivery catheter opening, whereby collapse of the compressor upon reception within the delivery catheter exerts a radial force upon the ED sufficient to compress the ED for reception in the delivery catheter.

Various aspects of the disclosure relate to system for deploying a reversibly compressible endovascular device within a lumen of a vessel. The system comprises a system for the radial compression of a reversibly compressible endovascular device (ED) prior to deployment as described above. The system further comprises a delivery catheter. The delivery catheter comprises proximal and distal delivery catheter openings The distal delivery catheter opening is for deploying the ED in to the lumen. The proximal delivery catheter opening is for receiving the ED from the delivery sheath. The proximal delivery catheter opening is of a width equal to or greater than the width of the delivery sheath opening. The system further comprises a hub connected to the proximal delivery catheter opening. The hub has a hub opening for receiving the delivery sheath in the hub when the ED is positioned in the delivery sheath, and positioning the delivery sheath in abutment with the proximal delivery catheter opening. The push wire and compressor wire are operable to be advanced through the delivery catheter to urge the ED and the compressor through the delivery catheter and out distal delivery catheter opening, wherein the compressor is operable to expand. In various embodiments, the push wire is operable to be retracted toward the hub to urge a deployed ED and expanded compressor toward the distal delivery catheter opening, whereby collapse of the compressor upon reception within the delivery catheter exerts a radial force upon the ED sufficient to compress the ED for reception in the delivery catheter.

Various aspects of the disclosure relate to a method of loading a reversibly compressible endovascular device (ED) into a delivery sheath having an interior width less than the radial width of the ED in an unexpanded position. The method comprises compressing the ED from an expanded position to an unexpanded position for reception in the delivery sheath. Compressing comprises urging the ED in the expanded position through an interior space of a compressor. The compressor comprises a tapered structure tapered from a distal compressor end toward a proximal compressor end of the tapered structure. The width of the interior space at the distal compressor end is greater than the diameter of the ED in the expanded position. The width of the interior space at the proximal compressor end is less than the diameter of the ED in the expanded position. Accordingly, urging the ED in the expanded position through the interior space of the compressor radially compresses the ED to an unexpanded position. The method further comprises urging the ED in the unexpanded position through a proximal compressor opening at the proximal compressor end and into the delivery sheath through a delivery sheath opening.

In various embodiments, the tapered structure is resiliently collapsible. In various embodiments, the tapered structure comprises a braided structure, for example, a polypropylene braided structure. In various embodiments, the tapered structure comprises a plurality of overlapping tongues coupled at the proximal compressor end, wherein each tongue tapers toward the proximal compressor end. In various embodiments, each tongue is slidable over an adjacent tongue to change the cross sectional area of the interior space.

Various aspects of the disclosure relate to a method of loading a reversibly compressible endovascular device (ED) into a delivery sheath having a width less than the ED in an unexpanded position. The method comprises compressing the ED from an expanded position to an unexpanded position for reception in the delivery sheath. Compressing comprises collapsing a compressor. The compressor comprising a tapered structure having a wall defining an interior space in which the ED is positioned in the expanded position. The wall exerts a radial force upon the ED to compress the ED, wherein the tapered structure is sized to be received in the delivery sheath when collapsed. The method further comprises urging the compressor, with the ED positioned in the interior space in the unexpanded position, into the delivery sheath through a delivery sheath opening sized to receive the compressor in a collapsed position.

In various embodiments, collapsing the compressor comprises progressively reducing the radial cross sectional area of the interior space across the length of the tapered structure.

In various embodiments, the wall comprises a braded structure, for example, a braided polypropylene structure. In various embodiments, the wall comprises a plurality of overlapping tongues coupled at a proximal end of the compressor, wherein each tongue tapers toward the proximal end of the compressor. In various embodiments, the collapsing the compressor comprises sliding the overlapping tongues over each other to progressively reducing the radial cross sectional area of the interior space across the length of the tapered structure.

In various embodiments, the method further comprises frictionally engaging the ED with an interior surface of the wall to retain the ED in the interior space.

Various aspects of the disclosure relate to a method of deploying a reversibly compressible endovascular device in a vessel. The method comprises loading the ED in a delivery sheath according to a method as described above. The method further comprises registering the delivery sheath opening with a proximal delivery catheter opening of a delivery catheter. The delivery catheter is disposed within the vessel. A distal delivery catheter opening of the delivery catheter is at a target site in the vessel. The method further comprises advancing the ED through the delivery sheath opening into the delivery catheter through the proximal delivery catheter opening, and through the delivery catheter toward a distal delivery catheter opening of the delivery catheter. The method further comprises advancing the ED through the distal delivery catheter opening and into the lumen of the vessel at the target site. The method further comprises expanding the ED in the lumen at the target site.

In various embodiments, the ED is a self-expanding ED and expanding the ED in the lumen involves allowing the ED to self-expand in the lumen. In various embodiments, expanding the ED within the lumen comprises inflating a balloon disposed within the tubular body to expand the ED. In various embodiments, the compressor is a reversibly collapsible compressor, and the method further comprises advancing the reversibly collapsible compressor through the distal delivery catheter opening into the lumen, and expanding the compressor to an expanded position. In various embodiments, the compressor is a self-expanding compressor. In various embodiments, the method further comprises positioning the expanded ED within the interior space of the expanded compressor. In various embodiments, the method further comprises compressing the ED from the expanded position to a compressed position for reception in the delivery catheter, wherein compressing comprises collapsing the compressor, wherein the wall exerts a radial force upon the ED to compress the ED, wherein the tapered structure is sized to be received in the delivery catheter when collapsed. In various embodiments, the method further comprises urging the compressor, with the ED positioned in the interior space in the compressed position, into the delivery catheter through the distal delivery catheter opening to receive the compressor in a collapsed position. In various embodiments, the method further comprises repositioning the delivery catheter in the lumen at a second position and advancing the ED through the distal delivery catheter opening into the lumen of the vessel, and expanding the ED in the lumen. In various embodiments, the ED is a self-expanding ED, and wherein expanding the ED in the lumen involves allowing the ED to self-expand in the lumen.

In various embodiments, the delivery catheter comprises a hub connected to the proximal delivery catheter opening and sized to receive the distal delivery sheath end. Registering the delivery sheath opening with the proximal deliver catheter opening comprises inserting the delivery sheath within the hub and abutting the delivery sheath opening to the proximal delivery catheter opening.

Various aspects of the disclosure relate to a system for the radial compression of a reversibly compressible endovascular device (ED) prior to deployment. The system comprises the ED. The ED comprises a tubular body. The tubular body is reversibly expandable, optionally self expanding, between a compressed position and an non-compressed position. The tubular body has an inner surface, an outer surface, and opposed distal and proximal ED openings. The system further comprises a delivery catheter sized to receive and maintain the ED in the compressed position. The delivery catheter has proximal and distal delivery catheter ends. The delivery catheter has a distal delivery catheter opening at the distal delivery catheter end, wherein the distal delivery catheter opening has a width sized to receive the ED into the delivery catheter in a compressed form. The system further comprises a compressor for compressing the ED for reception by the delivery catheter through the distal delivery catheter opening. The compressor comprises, in operation, a generally tapered structure defining an interior space. The tapered structure comprises distal and proximal compressor ends. The distal compressor end comprises a distal compressor opening sized to receive the ED in the non-compressed position. The tapered structure tapers from the distal compressor end toward the proximal compressor end such that the cross section of the interior space diminishes toward the proximal end. The cross sectional area of the interior space at the proximal compressor end is equal to or less than the cross sectional area of the distal delivery catheter opening. The system further comprises a push wire detachably attached to the ED and disposed within the delivery catheter. The push wire is operable to be advanced proximally through the delivery catheter toward the proximal delivery catheter end to urge the ED through the compressor, whereby the ED is deformed into the compressed position as it is urged through the compressor.

In various embodiments, the compressor comprises a proximal compressor opening at the proximal compressor end. In various embodiments, the proximal compressor opening is in communication with the distal delivery catheter opening. In various embodiments, the width of the proximal compressor opening is smaller than the radial diameter of the ED when the ED is in the non-compressed position. In various embodiments, the push wire is disposed within the ED through the proximal compressor opening.

In various embodiments, the push wire is operable to be advanced proximally through the delivery catheter to urge the ED through the proximal compressor opening and into the delivery catheter.

In various embodiments, the compressor is a funnel. In various embodiments, the tapered structure comprises a unitary body.

In various embodiments, the push wire is detachably attached to the ED by one or more threads. In various embodiments, the one or more threads are attached to the inner surface of the ED. In various embodiments, the one or more threads are electrolytically detachable from the ED. In various embodiments, the one or more threads are mechanically detachable from the ED. In various embodiments, the one or more threads is a single wire comprising a lasso looped around the tubular body at a proximal end of the ED.

In various embodiments, the compressor is detachable. In various embodiments, the compressor is collapsible. In various embodiments, the compressor is reversibly collapsible. In various embodiments, the tapered structure comprises a braided structure, for example, a polypropylene braided structure.

In various embodiments, the tapered structure comprises a plurality of overlapping tongues coupled at the proximal compressor end, wherein each tongue tapers toward the proximal compressor end.

In various embodiments, the proximal compressor end is sized to be received within the delivery catheter through the distal delivery catheter opening. In various embodiments, the compressor is sized to be received within the delivery catheter when the compressor is in a collapsed position.

In various embodiments, an inner wall of the delivery catheter is operable to exert a force against the side of the tapered structure, as the compressor is received within the delivery catheter, that is sufficient to collapse the compressor.

In various embodiments, the push wire is attached to the compressor, wherein the compressor is attached to the ED by one or more threads. In various embodiments, the one or more threads are attached to the inner surface of the ED. In various embodiments, the one or more wires are electrolytically detachable from the ED. In various embodiments, the one or more wires are mechanically detachable from the ED. In various embodiments, the one or more threads is a single wire comprising a lasso looped around the tubular body at a proximal end of the ED.

In various embodiments, push wire is attached to the compressor, wherein an interior surface of the tapered structure is operable to frictionally engage the outer surface of the ED.

In various embodiments, the push wire is operable to be advanced through the delivery catheter to urge the ED and the compressor toward the distal delivery catheter opening. Collapse of the compressor upon reception within the delivery catheter exerts a radial force upon the ED sufficient to compress the ED for reception in the delivery catheter.

In various embodiments, the one or more threads are attached to the inner surface of the ED. In various embodiments, the one or more wires are electrolytically detachable from the ED. In various embodiments, the one or more wires are mechanically detachable from the ED. In various embodiments, the one or more threads is a single wire comprising a lasso looped around the tubular body at a proximal end of the ED.

In various embodiments, an interior surface of the tapered structure is operable to frictionally engage the outer surface of the ED.

In various embodiments, the system further comprises a hollow compressor wire attached to the compressor and disposed within the delivery catheter. The compressor wire is operable to be advanced through the delivery catheter to urge the compressor through the distal delivery catheter opening, whereby the ED is deformed into the compressed position as it is urged through the compressor. In various embodiments, the push wire is disposed within the compressor wire, wherein the push wire is operable to be advanced through the delivery catheter independently of the compressor wire to urge the ED independently of the compressor. In various embodiments, the system further comprises a bump member disposed on the push wire between the ED and the compressor. The bump member is for abutting the ED along the circumference of the proximal ED opening to urge the ED distally through the delivery sheath when the push wire is advanced distally through the delivery sheath. In various embodiments, the push wire and compressor wire are operable to be advanced proximally through the delivery catheter to urge the ED and the compressor toward the delivery catheter. Collapse of the compressor upon reception within the delivery catheter exerts a radial force upon the ED sufficient to compress the ED for reception in the delivery sheath.

In various embodiments, the ED is a self-expanding ED.

Various aspects of the disclosure related to a system for deploying a reversibly compressible endovascular device within a lumen of a vessel of a patient. The system comprises a system for the radial compression of a reversibly compressible endovascular device (ED) prior to deployment as described above. The system further comprises a guide catheter comprising proximal and distal guide catheter openings. The distal guide catheter opening is for positioning at a target site in the lumen. The proximal guide catheter opening is for receiving the delivery catheter external to the patient. The proximal guide catheter opening is of a width greater than the width of the delivery catheter. The delivery catheter is operable to be inserted in the guide catheter through the proximal guide catheter opening and advanced through the guide catheter and out the distal guide catheter opening at the target site. The push wire is operable to be advanced through the delivery catheter to urge the ED through the delivery catheter and out distal delivery catheter, wherein the ED is operable to expand.

In various embodiments, the push wire is operable to be advanced through the delivery catheter to urge the compressor through the delivery catheter and out distal delivery catheter opening, wherein the compressor is operable to expand.

In various embodiments, the push wire is operable to be retracted proximally to urge a deployed ED and expanded compressor toward the distal delivery catheter opening. Collapse of the compressor upon reception within the delivery catheter exerts a radial force upon the ED sufficient to compress the ED for reception in the delivery catheter.

Various aspects of the disclosure relate to system for deploying a reversibly compressible endovascular device within a lumen of a vessel of a patient.

The system comprises a system for the radial compression of a reversibly compressible endovascular device (ED) prior to deployment as described above. The system further comprises a guide catheter comprising proximal and distal guide catheter openings. The distal guide catheter opening is for positioning at a target site in the lumen. The proximal guide catheter opening is for receiving the delivery catheter external to the patient. The proximal guide catheter opening is of a width greater than the width of the delivery catheter. The push wire and compressor wire are operable to be advanced through the delivery catheter to urge the ED and the compressor through the delivery catheter and out distal delivery catheter opening, wherein the compressor is operable to expand.

In various embodiments, the push wire and compressor wire are operable to be retracted proximally to urge a deployed ED and expanded compressor toward the distal delivery catheter opening. Collapse of the compressor upon reception within the delivery catheter exerts a radial force upon the ED sufficient to compress the ED for reception in the delivery catheter.

Various aspects of the disclosure related to a method of loading a reversibly compressible endovascular device (ED) into a delivery catheter having an interior width less than the radial width of the ED in an unexpanded position. The method comprises compressing the ED from an expanded position to an unexpanded position for reception in the delivery catheter. Compressing comprises urging the ED in the expanded position through an interior space of a compressor to radially compress the ED to an unexpanded position. The compressor comprises a tapered structure tapered from a distal compressor end toward a proximal compressor end. The width of the interior space at the distal compressor end is greater than the diameter of the ED in the expanded position. The width of the interior space at the proximal compressor end is less than the diameter of the ED in the expanded position. Accordingly, urging the ED in the expanded position through the interior space of the compressor radially compresses the ED to an unexpanded position. The method further comprises urging the ED in the unexpanded position through a proximal compressor opening at the proximal compressor end and into the delivery catheter through a distal delivery catheter opening.

In various embodiments, the tapered structure is resiliently collapsible. In various embodiments, the tapered structure comprises a braided structure, for example, a polypropylene braided structure. In various embodiments, the tapered structure comprises a plurality of overlapping tongues coupled at the proximal compressor end. Each tongue tapers toward the second compressor end. In various embodiments, each tongue is slidable over an adjacent tongue to change the cross sectional area of the interior space.

Various aspects of the disclosure relate to a method of loading a reversibly compressible endovascular device (ED) into a delivery sheath having a width less than the ED in an unexpanded position. The method comprises compressing the ED from an expanded position to an unexpanded position for reception in the delivery catheter. Compressing comprises collapsing a compressor. The compressor comprises a tapered structure having a wall defining an interior space in which the ED is positioned in the expanded position. The wall exerts a radial force upon the ED to compress the ED. The tapered structure is sized to be received in the delivery catheter when collapsed. The method further comprises urging the compressor, with the ED positioned in the interior space in the unexpanded position, into the delivery catheter through a distal delivery catheter opening sized to receive the compressor in a collapsed position.

In various embodiments, collapsing the compressor comprises progressively reducing the radial cross sectional area of the interior space across the length of the tapered structure.

In various embodiments, the wall comprises a plurality of overlapping tongues coupled at a proximal compressor end of the compressor. Each tongue tapers toward the proximal compressor end. In various embodiments, collapsing the compressor comprises sliding the overlapping tongues over each other to progressively reducing the radial cross sectional area of the interior space across the length of the tapered structure.

In various embodiments, the method comprises frictionally engaging the ED with an interior surface of the wall to retain the ED in the interior space.

Various aspects of the disclosure relate to method of deploying a reversibly compressible endovascular device in a vessel. The method comprises loading the ED in a delivery catheter according to a method as described above. The method further comprises advancing the delivery catheter through a guide catheter disposed within the vessel, wherein the guide catheter has a distal guide catheter opening positioned at a target site in the vessel, to position the distal delivery catheter opening at the target site. The method further comprises advancing the ED through the distal delivery catheter opening into the lumen of the vessel at a first position. The method further comprises expanding the ED in the lumen.

In various embodiments, the ED is a self-expanding ED. Expanding the ED in the lumen involves allowing the ED to self-expand in the lumen.

In various embodiments, expanding the ED within the lumen comprises inflating a balloon disposed within the tubular body to expand the ED.

In various embodiments, the compressor is a reversibly collapsible compressor. In such embodiments, the method further comprises advancing the reversibly collapsible compressor through the distal delivery catheter opening and into the lumen, and expanding the compressor to an expanded position. In various embodiments, the compressor is a self-expanding compressor.

In various embodiments, the method further comprises positioning the expanded ED within the interior space of the expanded compressor. In such embodiments, the method further comprises compressing the ED from the expanded position to a compressed position for reception in the delivery catheter, wherein compressing comprises collapsing the compressor, wherein the wall exerts a radial force upon the ED to compress the ED, wherein the tapered structure is sized to be received in the delivery catheter when in a collapsed form. The method further comprises urging the compressor, with the ED positioned in the interior space in the compressed position, into the delivery catheter through the distal delivery catheter opening to receive the compressor in a collapsed position.

In various embodiments, the method further comprises repositioning the delivery catheter in the lumen at a second position and advancing the ED through the distal delivery catheter opening into the lumen of the vessel, and expanding the ED in the lumen at the second position.

In various embodiments, the ED is a self-expanding ED, and expanding the ED in the lumen involves allowing the ED to self-expand in the lumen.

BRIEF DESCRIPTION OF THE DRAWINGS

In drawings which illustrate embodiments of the invention.

DEFINITIONS

"Bioabsorbable", "biodegradable", and "bioresorbable" are used herein synonymously to refer to a material or structure that degrades or dissolves in living tissues or systems of a body over time.

"Endovascular device" as used herein refers to a prosthesis that can be implanted within a body lumen or body conduit.

"Comprising", "including", and "involving", as used herein mean "including, but not limited to".

"Consisting" as used herein means "including and limited to".

"Proximal", as used herein with respect to the features of the systems of the present disclosure, refers to a feature closer to an operator of the system.

"Distal", as used herein with respect to the features of the systems of the present disclosure, refers to a feature away from the an operator of the system.

"Lumen" as used herein refers to the cavity defined by a tubular structure of a mammalian body including, but not limited to, a blood vessel, a ureter, a urethra, a bile duct.

"Resiliently deformable" as used herein pertains to an object that is capable of autonomously returning to its original shape upon release from a bent, stretched, compressed, or otherwise deformed shape.

DETAILED DESCRIPTION

Rigid or Removable Compressors

This disclosure generally relates to implantable devices, and particularly systems and methods of compressing resiliently deformable endovascular devices in a surgical setting prior to deployment in a vessel of a body of a patient. Any term or expression not expressly defined herein shall have its commonly accepted definition understood by a person skilled in the art. To the extent that the following description is of a specific embodiment or a particular use of the invention, it is intended to be illustrative only, and not limiting of the invention, which should be given the broadest interpretation consistent with the description as a whole and with the claims.

Figure 1:
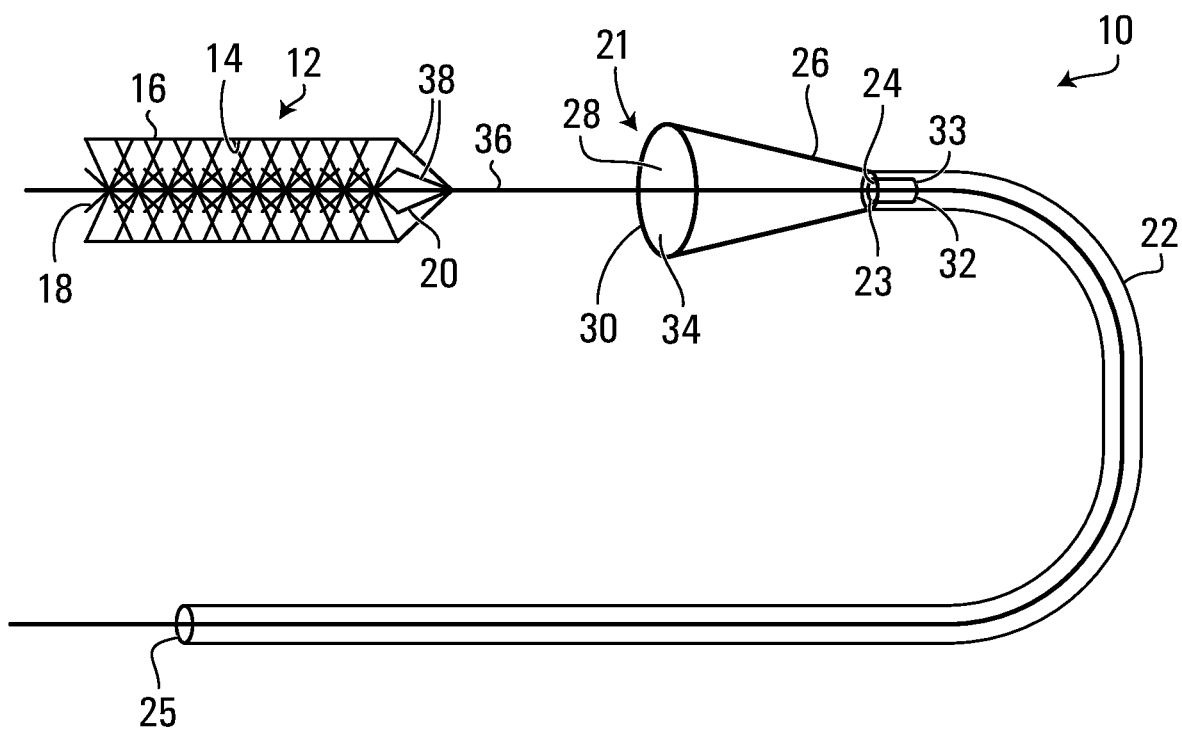
FIG. 1 is a drawing of a system for the radial compression of a reversibly compressible endovascular device prior to deployment according to a first embodiment of the invention.

Referring to FIG. 1, a system for the radial compression of a reversibly compressible endovascular device (ED) prior to deployment according to a first embodiment of the invention is shown generally at 10. The system includes a reversibly compressible ED shown generally at 12 as are generally known in the art. In general, the ED comprises a tubular body that is expandable between a non-compressed position, as depicted in FIG. 1, and a compressed position for loading within a catheter for delivery to a target site in the lumen of a vessel within the body of a subject. The tubular body has an inner surface 14, an outer surface 16, and opposed distal and proximal opposed ED openings 18 and 20.

The system further includes a delivery sheath 22 sized to receive and maintain ED 12 in the compressed position upon reception in the delivery sheath in the compressed position. Delivery sheath 22 has a distal delivery sheath end 23 having a delivery sheath opening 24. Delivery sheath opening 24 has a width sized to receive the ED 12 into delivery sheath 22 in a compressed form. Delivery sheath 22 further has a proximal delivery sheath end 25.

The system further includes a compressor shown generally at 21 for radially compressing the ED 12 for reception by the delivery sheath 22 through the delivery sheath opening 24. The compressor includes a generally tapered structure 26 defining an interior space 28. The tapered structure comprises distal and proximal compressor ends 30 and 32, wherein proximal end 32 is proximal to the delivery sheath opening 24.

Distal compressor end 30 comprises a distal compressor opening 34 sized to receive ED 12 in the non-compressed position. As illustrated in FIG. 1, tapered structure 26 tapers from distal compressor opening 34 toward proximal end 32 such that the radial cross section of interior space 28 diminishes from distal compressor end 30 toward proximal compressor end 32. Proximal compressor end 32 comprises a proximal compressor opening 33 in communication with delivery sheath opening 24. The width of proximal compressor opening 33 is less than the radial diameter of ED 12 when the ED is in the non-compressed position. The radial cross sectional area of interior space 28 proximal to the proximal compressor end 32, e.g. at proximal compressor opening 33, is equal to or less than the radial cross sectional area of delivery sheath opening 24. In this way, as ED 12 moves through tapered structure 26, it will be compressed to have a radial cross section less than the radial cross section of delivery sheath opening 24, such that ED 12 can be received within delivery sheath 22 in the compressed position. As such, ED 12, in a compressed form, can be urged through second compressor opening 33 and received within delivery sheath 22.

The system further comprises a push wire 36 that is detachably attached to ED 12. Push wire 36 is attached to ED 12 by at least one (i.e. one or more) threads 38. Threads 38 can be made of any suitable material for attaching the push wire to the ED, including metal wire. In FIG. 1, threads 38 are shown radiating from push wire 36 and attached to ED 12 at second ED opening 20. However, the skilled person understands that threads 38 may be attached to ED 12 at a different position, for example, to inner surface 14 or outer surface 16. In some embodiments, threads 38 could be attached at distal ED opening 18.

In some embodiments, the at least one thread is a single thread comprising a lasso, wherein the lasso is looped and tightened around the tubular body of the ED proximal to proximal ED opening to form a cincture about the proximal end of the ED.

Threads 38 may be electrolytically detachable from ED 12 once the ED is positioned at the target site within the lumen of the vessel, as is known in the field. Alternatively, threads 38 may be mechanically detachable from ED 12. It is within the purview of the skilled person to select an appropriate means of detaching threads 38 from the ED. In embodiments involving a lasso-style attachment, the loop of the lasso may be broken to release ED. The skilled person will understand that a variety of suitable detachment systems are available in the art as described in, for example, U.S. Pat. No. 10,405,868, 9,717,502, 10,182,931, and 9,814,466. Lasso-style mechanisms are known in the art as described, for example, by Pumar et al. (American Journal of Neuroradiology, 26: 2573-2577).

Threads 38 may be made of any suitable materials as are known in the field. For example, threads 38 may be made of metal wire.

As shown in FIG. 1, push wire 36 is disposed within delivery sheath 22 through delivery sheath opening 24. Push wire 36 further extends distally through proximal compressor opening 33, interior space 28, and distal compressor opening 34, to where it is attached to ED 12. Push wire 36 is operable to be advanced proximally through delivery sheath 22 to urge ED 12 through the compressor (i.e. tapered structure 26), whereby ED 12 is deformed into a compressed position as it is urged through the compressor from distal end 30 to proximal end 32, i.e. due to the progressively diminished cross sectional area of interior space 28, and further urged through proximal compressor opening 33 and delivery sheath opening 24 into delivery sheath 22 in a compressed position.

As shown in FIG. 1, push wire 36 may also be disposed within ED 12 through proximal ED opening 20.

A depicted in FIG. 1, tapered structure 26 may take the form of a funnel. In some embodiments, the width of proximal compressor end 32 is less than the width of delivery sheath opening 24 such that proximal compressor end 32 is sized to be received within delivery sheath 22 through delivery sheath opening 24. However, in alternative embodiments, the proximal compressor end may abut the delivery sheath end 23. The skilled person understands that the proximal compressor end and the delivery sheath end can be designed to cooperate in numerous different ways, and that it is only important that proximal compressor opening have a width equal to or less than the delivery sheath opening so that the ED will be in a sufficiently compressed position to be received within the delivery sheath as the ED approaches the proximal compressor end. In some embodiments, for example, the compressor may be integral with the delivery sheath, i.e. the compressor and delivery sheath are a single continuous unitary unit.

As depicted in FIG. 1, the tapered structure itself may have a unitary (i.e. one-piece) body. In some embodiments, such as depicted in FIG. 1, tapered structure 26 is removable once ED 12 has been received in a compressed position within delivery sheath 22

In operation, starting with ED 12 in an expanded position, retracting push wire 36 proximally into delivery sheath 22 toward proximal delivery sheath end 25 urges ED 12 into interior space 28 of tapered structure 26 through distal compressor opening 34, and toward proximal compressor end 32 to radially compress ED 12 to a compressed (i.e. unexpanded) position as the cross sectional area of interior space 28 diminishes from distal compressor end 30 toward proximal compressor end 32. Further retraction of push wire 36 toward proximal delivery sheath end 25 urges ED 12 in the compressed position through proximal compressor opening 33 and into delivery sheath 22.

Deployment

Once ED 12 has been received within delivery sheath 22 in a compressed position, the delivery sheath 22 can be used in conjunction with a delivery catheter for delivery of the ED to the target site.

Figure 2A:
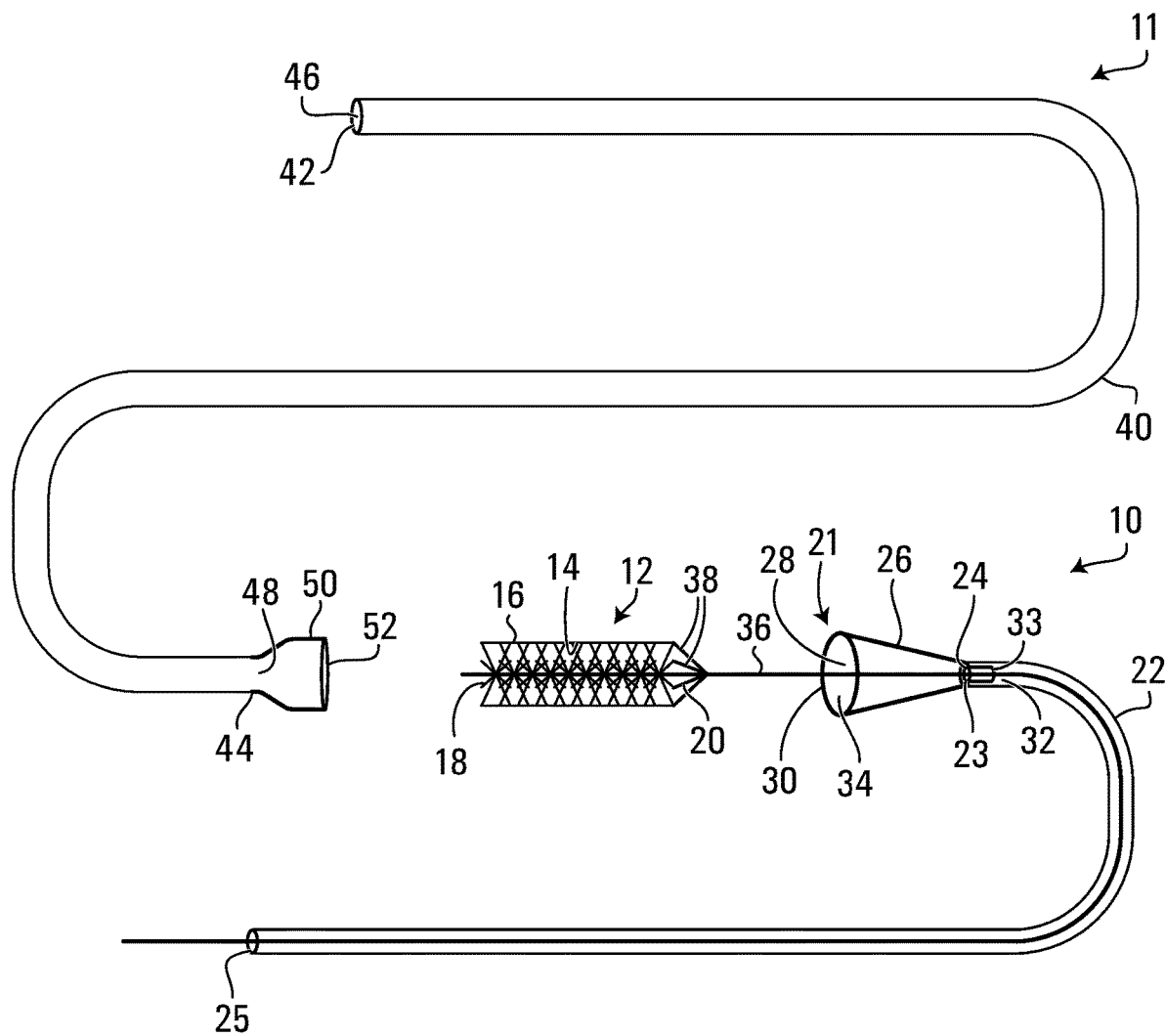
FIG. 2A is a drawing of a system for the deployment of a reversibly compressible endovascular device according to a first embodiment of the invention.
Figure 2B:
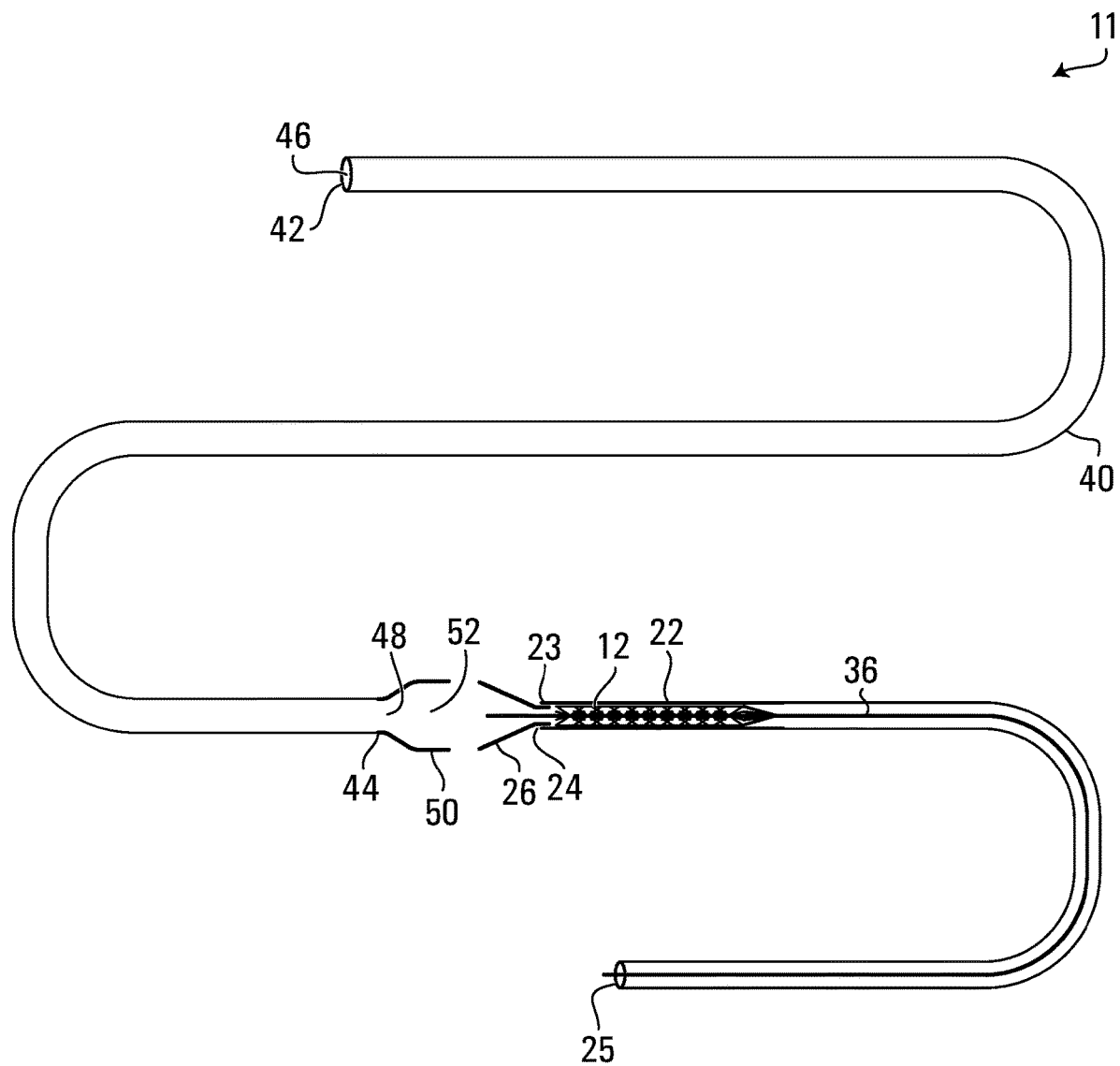
FIG. 2B is a drawing of a system for the deployment of a reversibly compressible endovascular device according to the embodiment illustrated in FIG. 2A, but with the endovascular device compressed within the delivery sheath.

Referring to FIGS. 2A and 2B, a system for deploying a reversibly compressible endovascular device within a lumen of a vessel is shown generally at 11. The system comprises a system for the radial compression of a reversibly compressible endovascular device (ED) prior to deployment as described above with reference to FIG. 1. The system further comprises a delivery catheter 40 having distal and proximal delivery catheter ends 42 and 44 having distal and proximal delivery catheter openings 46 and 48, respectively. Proximal delivery catheter opening 48 is for receiving ED 12 from delivery sheath 22 in a compressed position, whereas distal delivery catheter opening 46 is for deploying ED 12 into the lumen of the vessel. Accordingly, proximal end opening 48 is of a width equal to or greater than the width of delivery sheath opening 24.

The system further comprises a hub 50 connected to proximal delivery catheter end 44 and in communication with proximal delivery catheter opening 48. Hub 50 has hub opening 52 for receiving delivery sheath 22 in hub 50 when ED 12 is positioned within the delivery sheath. Hub 50 is for registering delivery sheath opening 24 in abutment with proximal delivery catheter opening 48.

Push wire 36 is operable to be advanced distally through delivery sheath 22 and delivery catheter 40 to urge ED 12 from the delivery sheath and into the delivery catheter through proximal delivery catheter opening 48, and through the delivery catheter distally toward and out distal catheter opening 46.

Figure 2C:
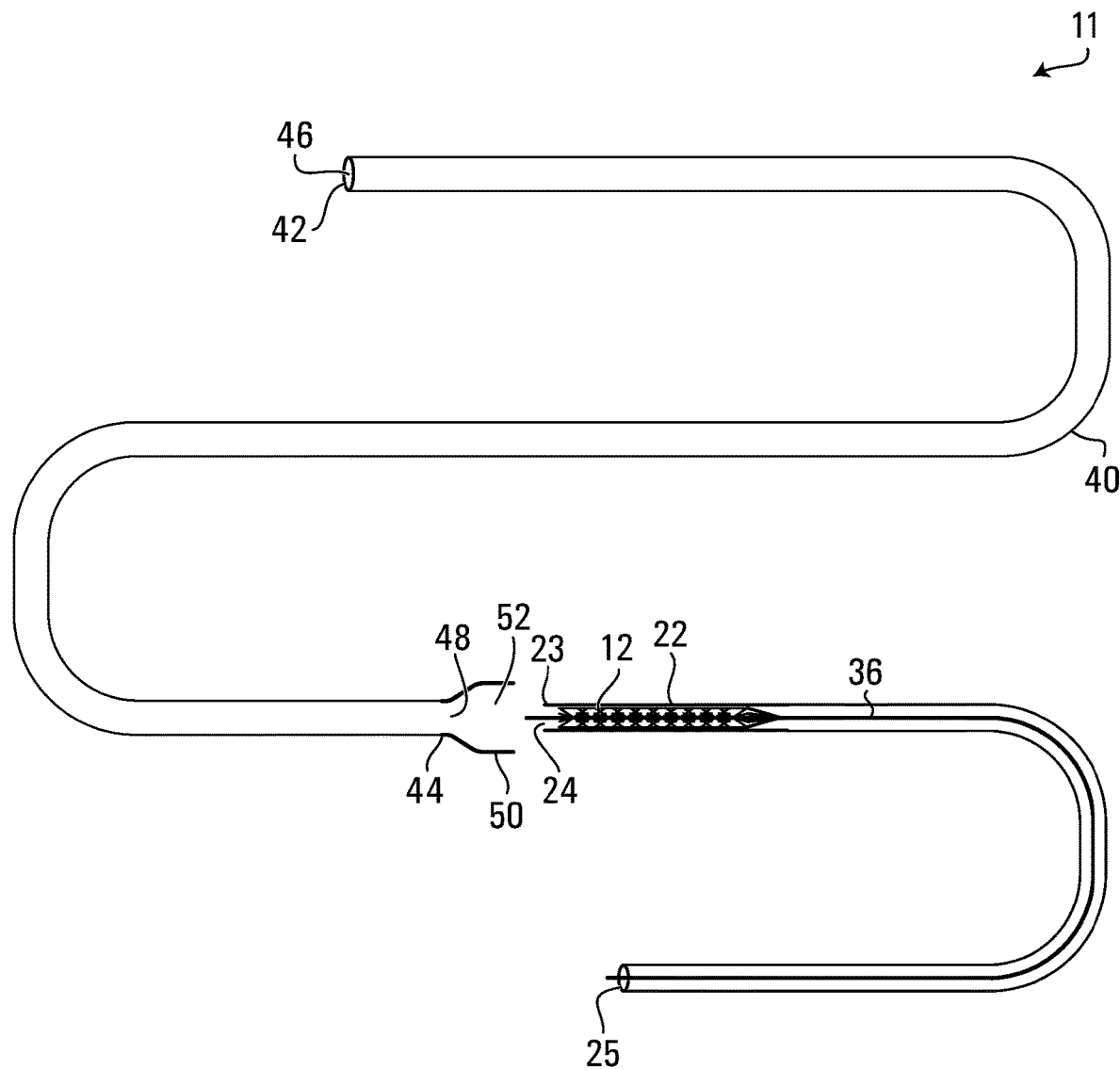
FIG. 2C is a drawing of a system for the deployment of a reversibly compressible endovascular device according to the embodiment illustrated in FIGS. 2A and 2B, but after the compressor has been removed.
Figure 2D:
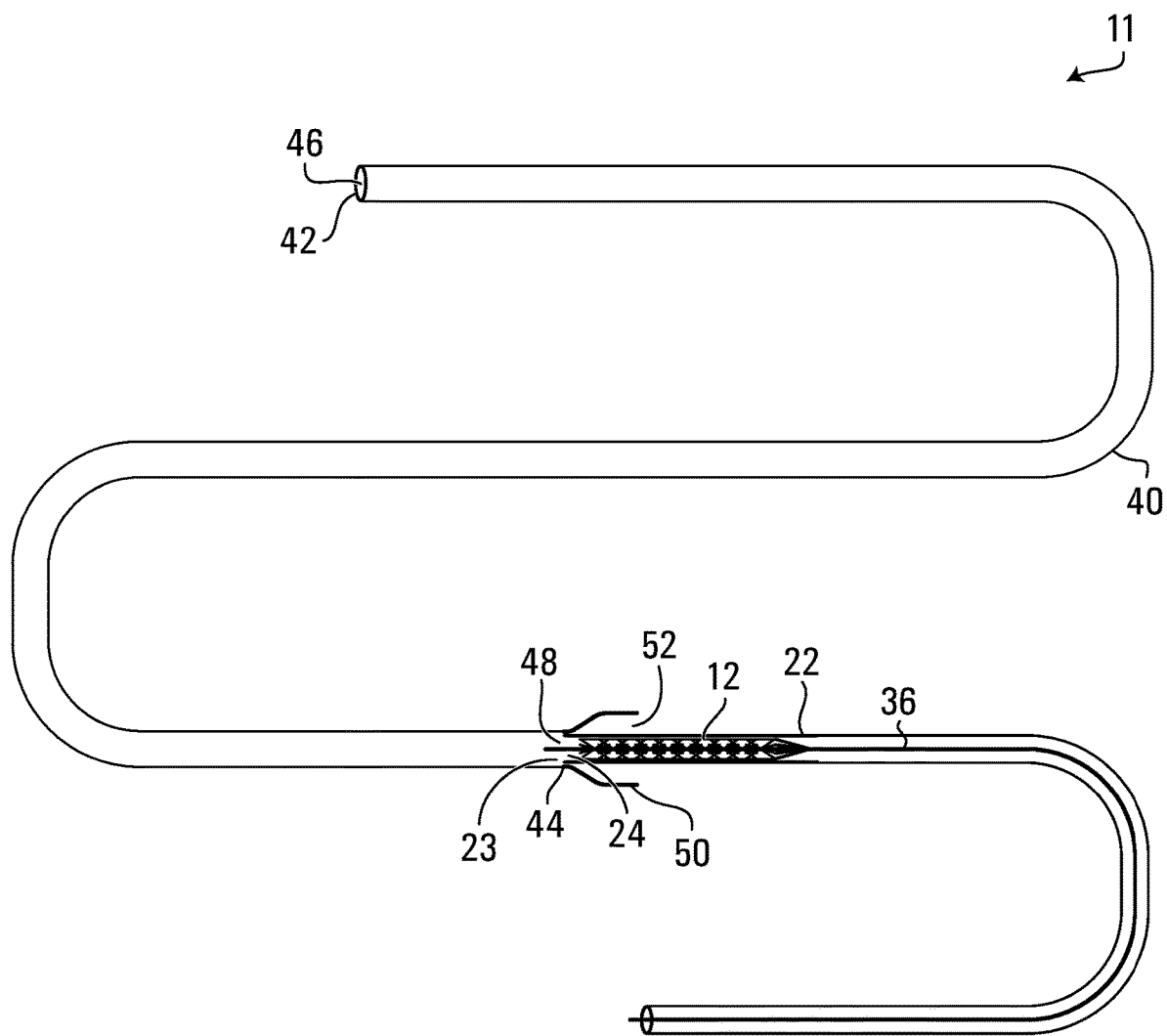
FIG. 2D is a drawing of a system for the deployment of a reversibly compressible endovascular device according to the embodiment illustrated in FIGS. 2A, 2B, and 2C, but with the delivery sheath registered with the delivery catheter prior to transfer of the compressed endovascular device from the delivery sheath to the delivery catheter.
Figure 2E:
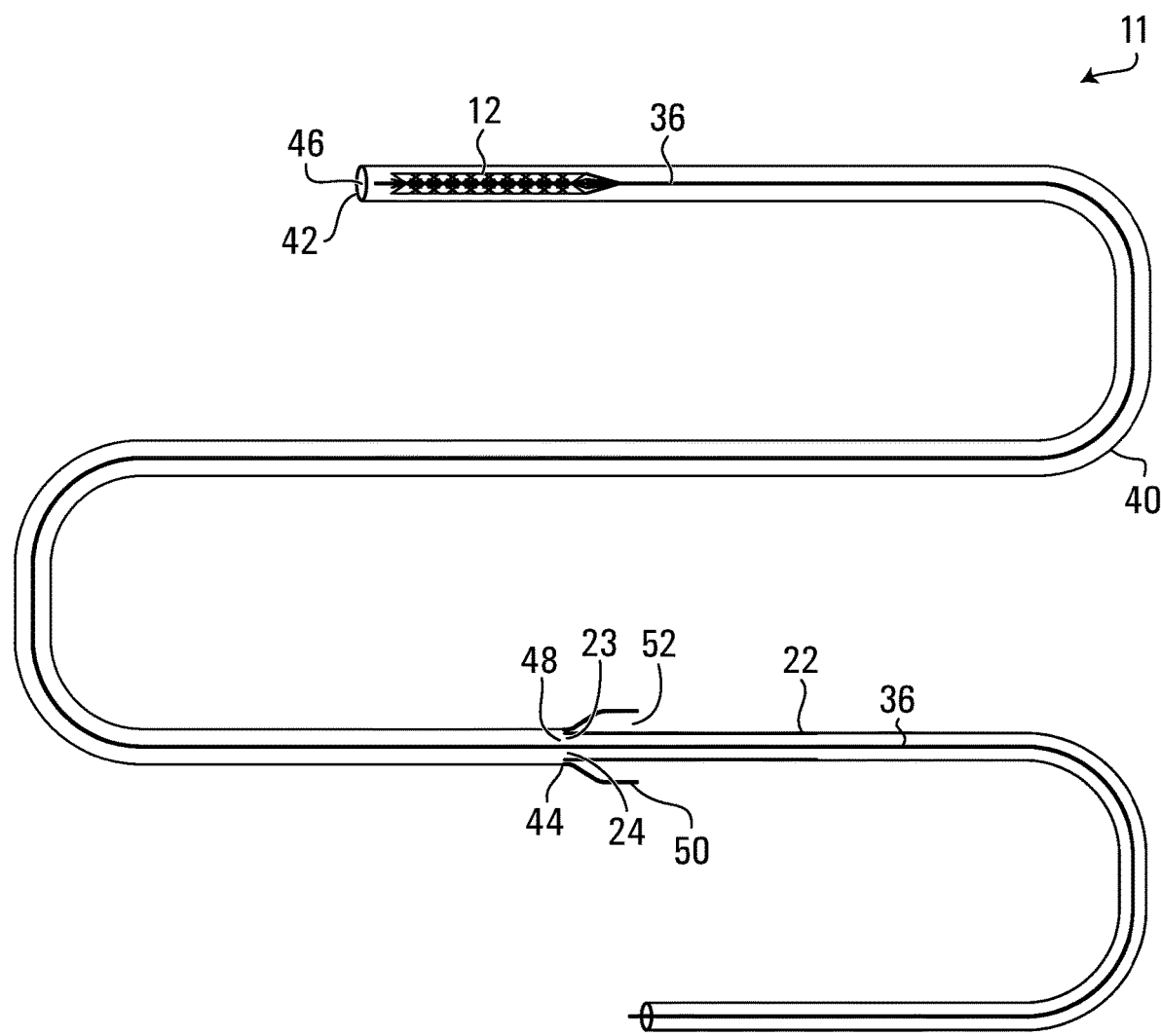
FIG. 2E is a drawing of a system for the deployment of a reversibly compressible endovascular device according to the embodiment illustrated in FIGS. 2A, 2B, 2C, and 2D, showing the compressed endovascular device advanced to the distal end of the delivery catheter prior to deployment at a target site within a lumen of a subject.
Figure 2F:
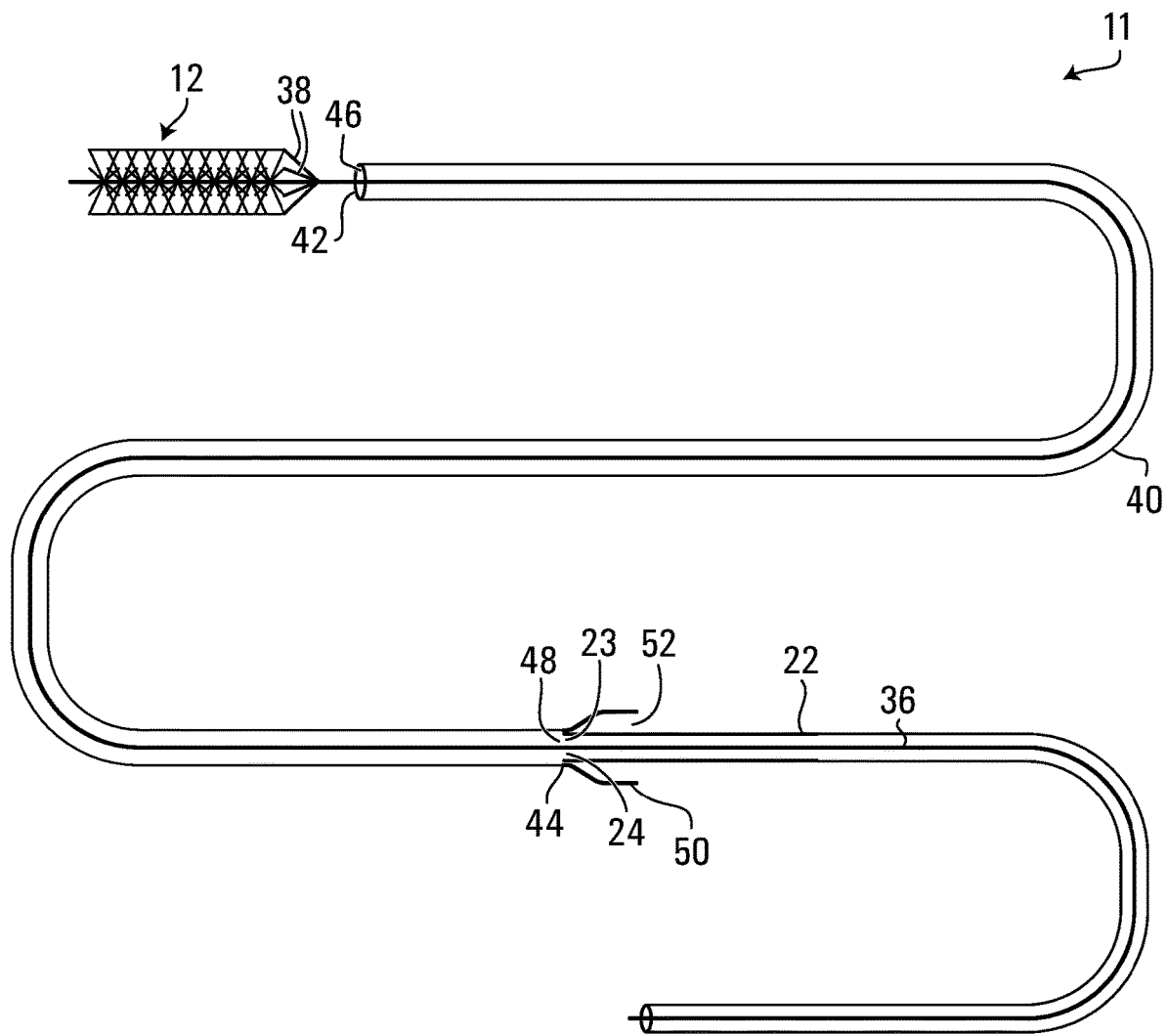
FIG. 2F is a drawing of a system for the deployment of a reversibly compressible endovascular device according to the embodiment illustrated in FIGS. 2A, 2B, 2C, 2D, and 2E showing the endovascular device advanced out of the distal opening of the delivery catheter and expanded at the target site within the lumen of a subject.

In operation, delivery catheter 40 will typically be deployed in a vessel of a subject, such that distal delivery catheter end 42 is positioned at a target site, with hub 50 remaining outside of the body of the subject. Referring to FIG. 2B, ED 12 is compressed and loaded in delivery sheath 22 as described above. Referring to FIG. 2C, tapered structure 26 may then be removed prior to engaging system 10 with delivery catheter 40. Referring to FIG. 2D, distal end 23 of delivery sheath 22, with ED 12 compressed within it, is then inserted in hub 50 through hub opening 52. Delivery sheath opening 24 is then registered with proximal delivery catheter opening 48. Referring to FIG. 2E, push wire 36 is then used to advance ED 12 distally through delivery sheath opening 24 into delivery catheter 40 through proximal delivery catheter opening 48, and then distally through the delivery catheter 40 toward distal delivery catheter opening 46. Referring to FIG. 2F, ED 12 is then advanced through distal delivery catheter opening 46 into the lumen of the vessel where it is expanded to its non-compressed position at the target site. Once ED 12 is in its non-compressed position at the target site, threads 38 can be detached from ED 12. Delivery catheter 40 may then be repositioned for the deployment of a further ED, or removed from the patient.

In embodiments where the ED is a self-expanding ED, expanding ED 12 in the lumen consists of simply allowing the ED to self-expand. Otherwise, it will be within the purview of a skilled person to select and employ an appropriate means of expanding an ED. For example, alternatives for expanding the ED may include inflating a balloon disposed within the tubular body of the ED to expand the ED.

Collapsible Compressors

Figure 3:
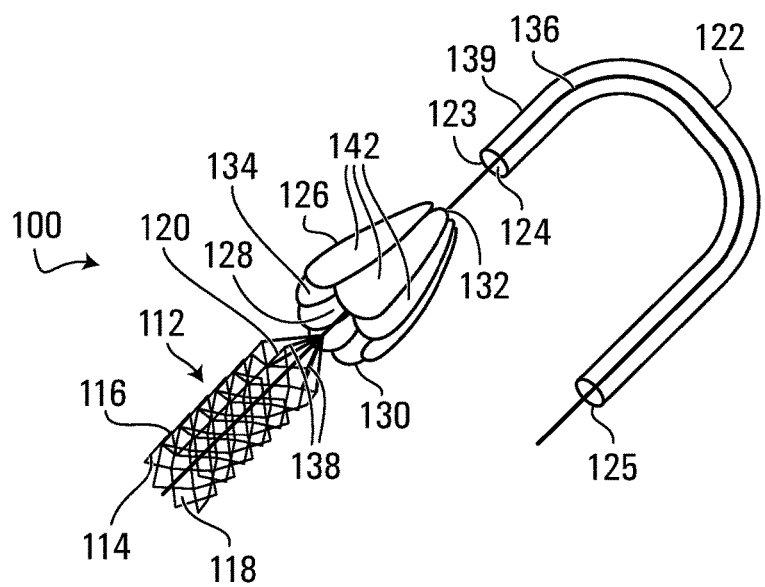
FIG. 3 is a is a drawing of a system for the radial compression of a reversibly compressible endovascular device prior to deployment according to a second embodiment of the invention involving a collapsible compressor.

Referring to FIG. 3, a system for the radial compression of a reversibly compressible endovascular device (ED) prior to deployment according to a second embodiment of the invention is shown generally at 100. The system includes a reversibly compressible ED 112 as are generally known in the art. In general, the ED comprises a tubular body that is expandable between a non-compressed position, as depicted in FIG. 3, and compressed position for loading within a delivery catheter for delivery to a target site in the lumen of a vessel within the body of a subject. The tubular body has an inner surface 114, an outer surface 116, and distal and proximal opposed ED openings 118 and 120.

The system further includes a delivery sheath 122 sized to receive and maintain the ED 112 in the compressed position upon reception in the delivery sheath in a compressed position. Delivery sheath 122 has a distal delivery sheath end 123 having a delivery sheath opening 124. Delivery sheath opening 124 has a width sized to receive the ED 112 into delivery sheath 122 in a compressed form. Delivery sheath 122 further has a proximal delivery sheath end 125.

The system further includes a compressor 126 for radially compressing the ED 112 for reception in the delivery sheath 122 through delivery sheath opening 124. The compressor includes a generally tapered structure defining an interior space 128 in which ED 112 initially may be at least partially positioned in a non-compressed position. Compressor 126 comprises distal and proximal compressor ends 130 and 132, wherein proximal end 132 is adjacent to delivery sheath opening 124.

Distal compressor end 130 comprises a distal compressor opening 134 sized to receive the ED 112 in the non-compressed position. As illustrated in FIG. 3, compressor 126 tapers from distal compressor opening 134 toward proximal compressor end 132 such that the radial cross section of the interior space 128 diminishes from distal compressor end 130 toward proximal compressor end 132. The width of compressor 126 at proximal compressor end 132 is less than the width of delivery sheath opening 124 such that proximal compressor end 132 is sized to be received within delivery sheath 122 through delivery sheath opening 124 as discussed below.

Compressor 126 is collapsible such that, as it collapses, the cross sectional area of interior space 128 at any position along the longitudinal axis of the compressor from distal compressor end 130 to proximal compressor end 132 progressively decreases. As the cross sectional area of interior space 128 decreases, compressor 126 exerts a radial force against ED 112 positioned therein to compress the ED.

Compressor 126 is sized such that, in a collapsed form, it is sized to be received within delivery sheath 122 through delivery sheath opening 124. ED 112, being compressed within interior space 128 as compressor 126 collapses, is thereby compressed for reception within delivery sheath 122.

The system further comprises a push wire 136 that is attached to proximal compressor end 132. Push wire 136 is also detachably attached to ED 112. Push wire 136 is attached to ED 112 by at least one (i.e. one or more) threads 138. In FIG. 3, threads 138 are shown radiating from push wire 136 and attached to ED 112 at proximal ED opening 120. However, the skilled person understands that threads 138 may be attached to ED 112 at a different position, for example, to inner surface 114 or outer surface 116. In some embodiments, threads 138 could be attached at distal ED opening 118.

The skilled person further understands that one or more threads 138 may attach ED 112 to compressor 126 rather than push wire 136. In some embodiments, the at least one thread is a single thread comprising a lasso, wherein the lasso is looped and tightened around the tubular body of the ED proximal to proximal ED opening to form a cincture about the proximal end of the ED.

As discussed above in respect of the first embodiment, threads 138 may be electrolytically or mechanically detachable from ED 112 once the ED is positioned at the target site within the lumen of the vessel, as is known in the field. In embodiments involving a lasso-style attachment, the loop of the lasso may be broken to release ED. Similarly, threads 138 may be made of any suitable materials as are known in the field.

Figure 4A:
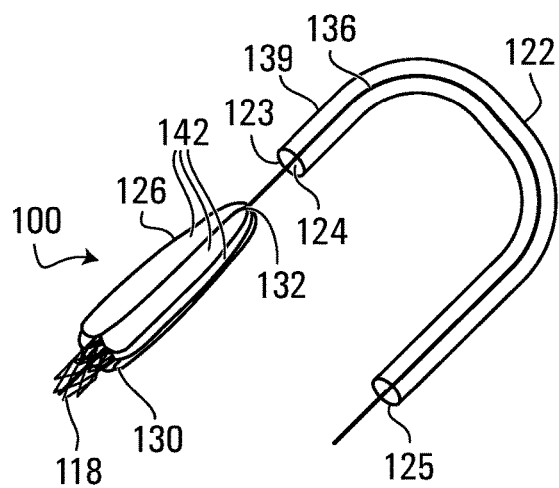
FIG. 4A is a drawing of a system for the radial compression of a reversibly compressible endovascular device prior to deployment according to a third embodiment of the invention involving a collapsible compressor that is frictionally engaged with the endovascular device.
Figure 4B:
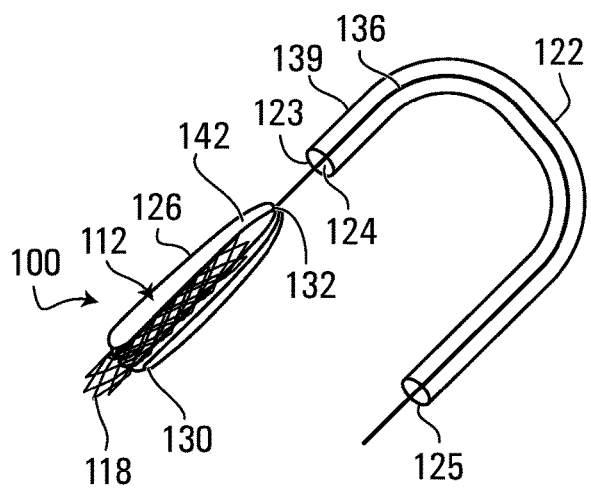
FIG. 4B is a drawing of a system for the radial compression of a reversibly compressible endovascular device prior to deployment according to the embodiment depicted in FIG. 4A, but with a couple of tongues removed to reveal the ED within.

Alternatively, referring to FIGS. 4A and 4B, ED 112 may not be connected to compressor 126 or push wire 136 by threads. Rather, compressor 126 may be sized and configured such that ED 112 is initially frictionally engaged with an interior surface of compressor 126. Accordingly, as compressor 126 is drawn into delivery sheath 122 through delivery sheath opening 124, ED 112 is drawn with it and compressed as compressor 126 collapses.

As shown in FIGS. 3, 4A, and 4B, push wire 136 is disposed within delivery sheath 122, and operable to be retracted proximally through delivery sheath 122 toward proximal delivery sheath end 125 to urge compressor 126 into delivery sheath 122 through delivery sheath opening 124. In various embodiments, an inner wall 139 of delivery sheath 122 is operable to exert a force against the outer surface of compressor 126 as compressor 126 is received within the delivery sheath, that is sufficient to collapse the tapered structure.

As shown in FIG. 3, push wire 136 may also be disposed within ED 112 through proximal ED opening 120.

A depicted in FIGS. 3, 4A, and 4B, compressor 126 may take the general form of a funnel. In some embodiments, as depicted in FIGS. 3, 4A, and 4B, the compressor 126 comprises a plurality of overlapping tongues 142 coupled at proximal compressor end 132, wherein each tongue 142 tapers toward the proximal compressor end. Each tongue 142 is slidable over an adjacent tongue to change the cross sectional area of the interior space along the longitudinal axis from distal compressor end 130 to proximal compressor end 132 as compressor 126 is drawn into delivery sheath 122 through delivery sheath opening 124.

However, the skilled person will understand that collapsible compressors according to the present disclosure could include a variety of radially compressible structures that, when at least partially received within the delivery sheath, form a tapered structure that can accommodate an ED in non compressed form and, as urged into the delivery sheath along with the ED, collapse to compress the ED to a compressed form. Such compressors could be formed of a braided structure, for example, a polypropylene braided structure or a metal braided structure as is known in the art and used in some cases for the fabrication of EDs themselves.

In various embodiments, compressor 126 is reversibly collapsible. For example, the tapered structure may be resiliently deformable such that, after reception in delivery sheath 122, it may be pushed out of delivery sheath 122 through delivery sheath opening 124 using push wire 136, into and through a delivery catheter, and out a distal delivery catheter opening (e.g. into the lumen of a vessel), at which time it will expand to a non-collapsed formation to permit release of ED 112 at the target site. Alternatively, the tapered structure may be actively expanded upon emergence from the delivery sheath, or deliver catheter as the case may be, by any means known in the art, e.g. using a balloon.

In operation, starting with ED 112 in an expanded position, retracting push wire 136 into delivery sheath 122 toward proximal delivery sheath end 125 urges compressor 126 into delivery sheath 122 through delivery sheath opening 124. As compressor 126 is urged into delivery sheath 122, the cross sectional area of interior space 128 at any position along the longitudinal axis of the compressor from distal compressor end 130 to proximal compressor end 132 is progressively reduced, wherein compressor 126 exerts a radial force against ED 112 positioned therein to radially compress the ED for reception within delivery sheath 122 through delivery sheath opening 124.

Deployment

Once ED 112 has been received within delivery sheath 122 in a compressed position, the delivery sheath 122 can be used in conjunction with a delivery catheter for delivery of the ED to the target site.

Figure 5A:
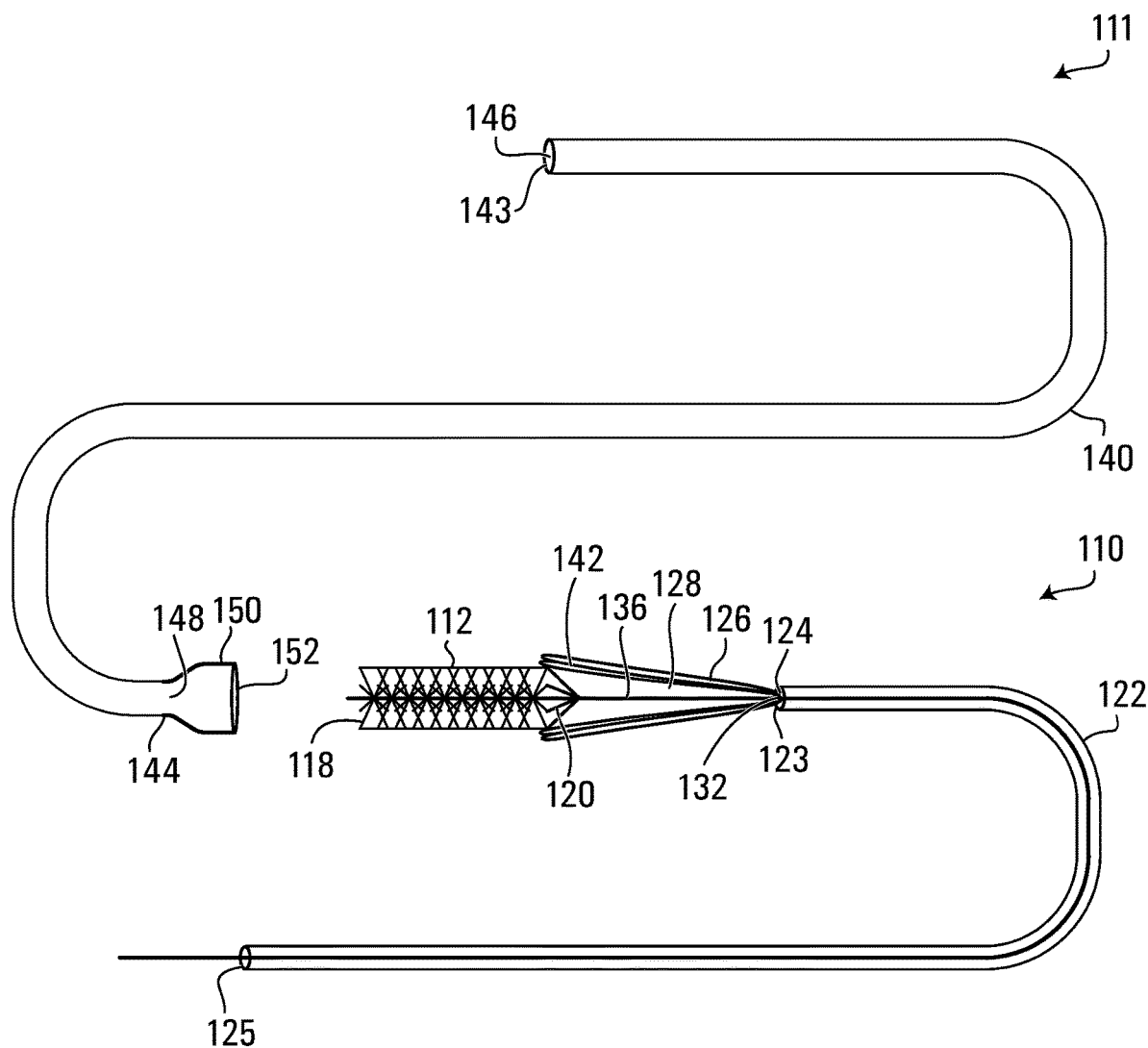
FIG. 5A is a drawing of a system for the deployment of a reversibly compressible endovascular device according to an embodiment of the invention involving a collapsible compressor as depicted in FIG. 3.
Figure 5B:
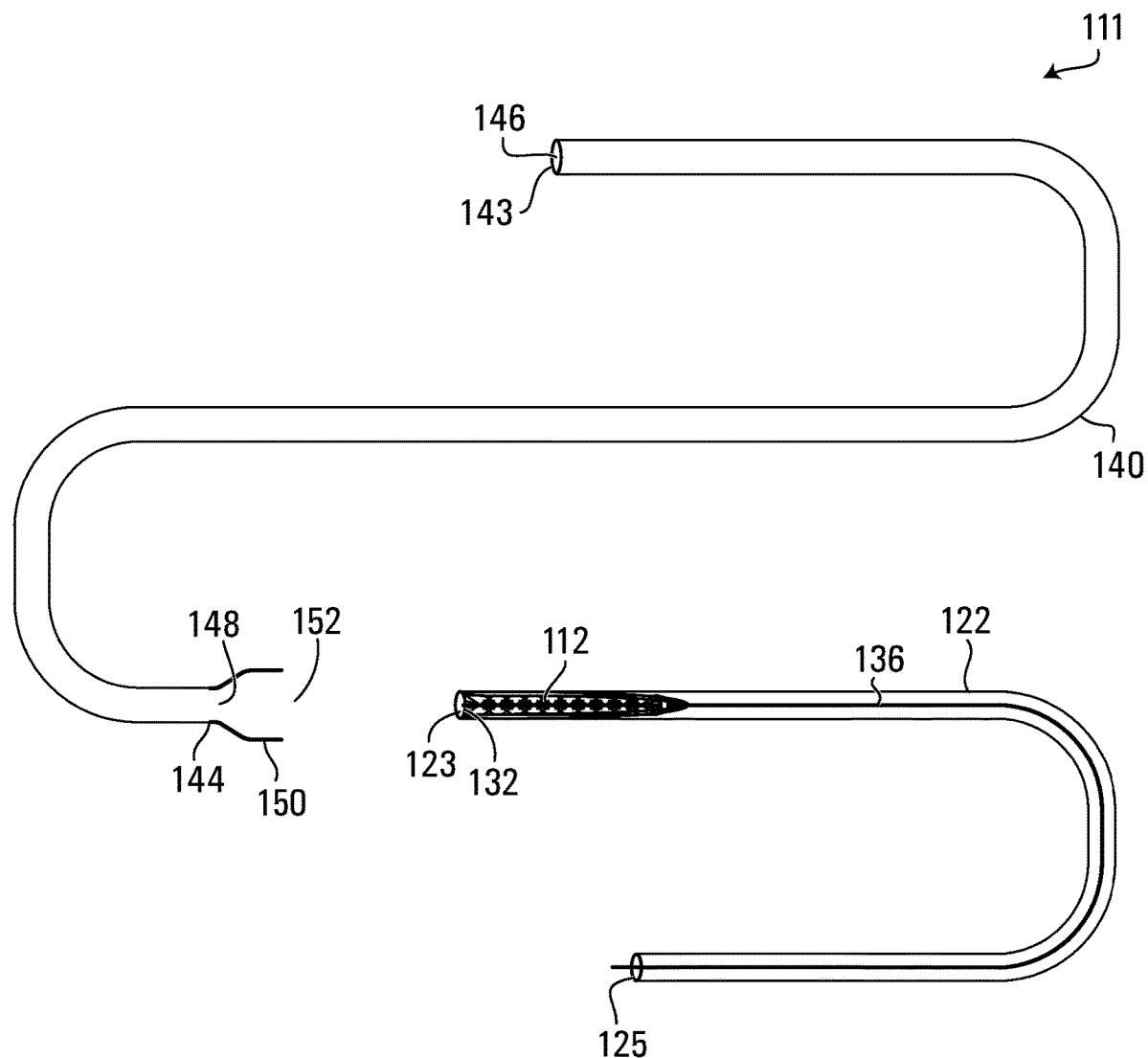
FIG. 5B is a drawing of a system for the deployment of a reversibly compressible endovascular device according to the embodiment illustrated in FIG. 5A, but with the endovascular device compressed within the delivery sheath.

Referring to FIGS. 5A and 5B, a system for deploying a reversibly compressible endovascular device within a lumen of a vessel is shown generally at 111. The system comprises a system for the radial compression of a reversibly compressible endovascular device (ED) prior to deployment as described above with reference to FIGS. 3, 4A, and 4B. The system further comprises a delivery catheter 140 having distal and proximal delivery catheter ends 143 and 144 having distal and proximal delivery catheter openings 146 and 148, respectively. Proximal delivery catheter opening 148 is for receiving ED 112 from delivery sheath 122 in a compressed position, whereas distal delivery catheter opening 146 is for deploying ED 112 into the lumen of the vessel. Accordingly, proximal delivery catheter opening 148 is of a width equal to or greater than the width of delivery sheath opening 124.

Figure 5C:
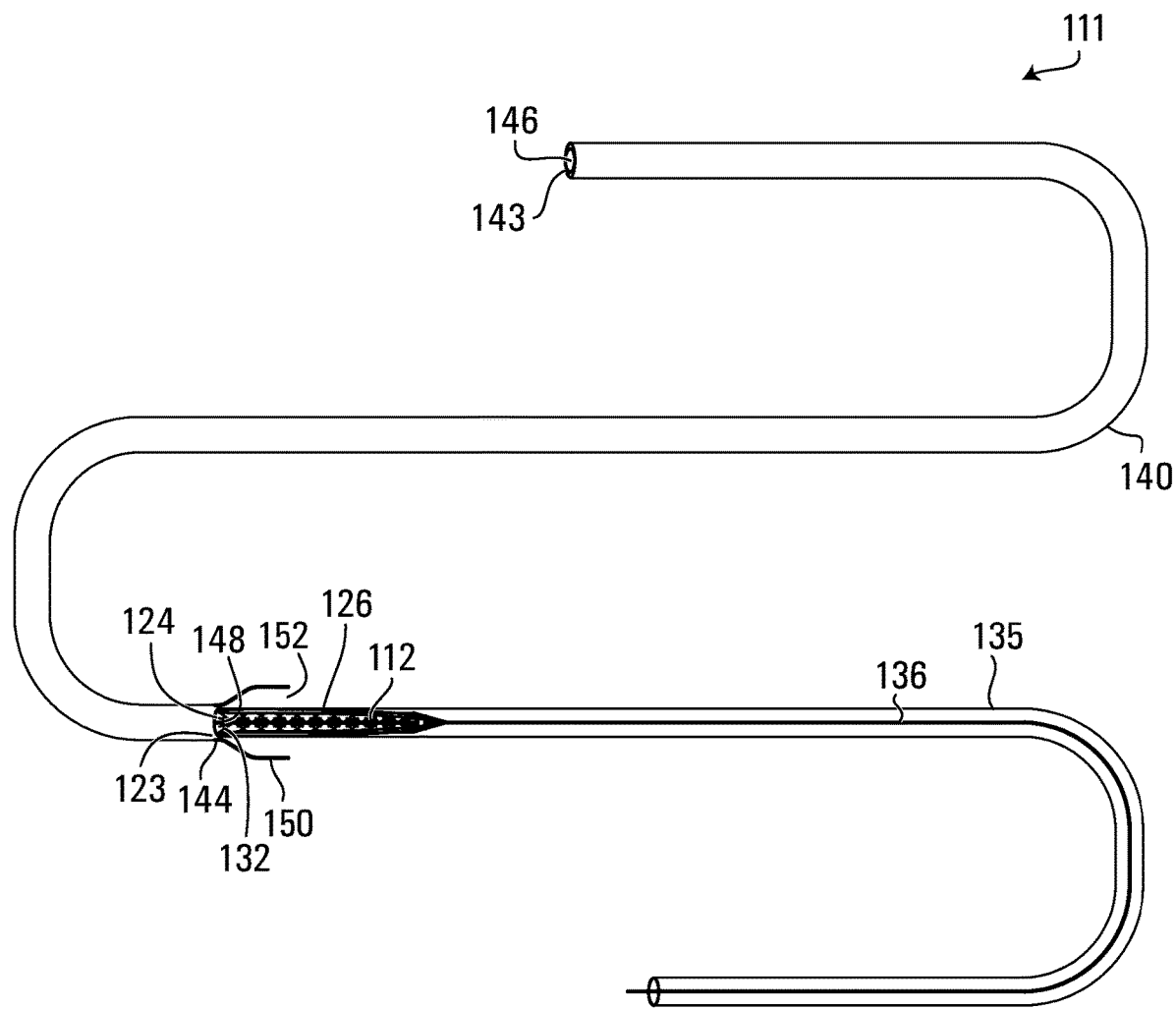
FIG. 5C is a drawing of a system for the deployment of a reversibly compressible endovascular device according to the embodiment illustrated in FIGS. 5A and 5B, but with the delivery sheath registered with the delivery catheter prior to transfer of the compressed endovascular device from the delivery sheath to the delivery catheter.

The system further comprises a hub 150 connected to proximal delivery catheter end 144 and in communication with proximal delivery catheter opening 148. Referring to FIG. 5C, hub 150 has hub opening 152 for receiving delivery sheath 122 in hub 150 when compressor 126 and ED 112 are positioned in the delivery sheath. Hub 150 is for positioning delivery sheath opening 124 in abutment with proximal delivery catheter opening 148.

Figure 5D:
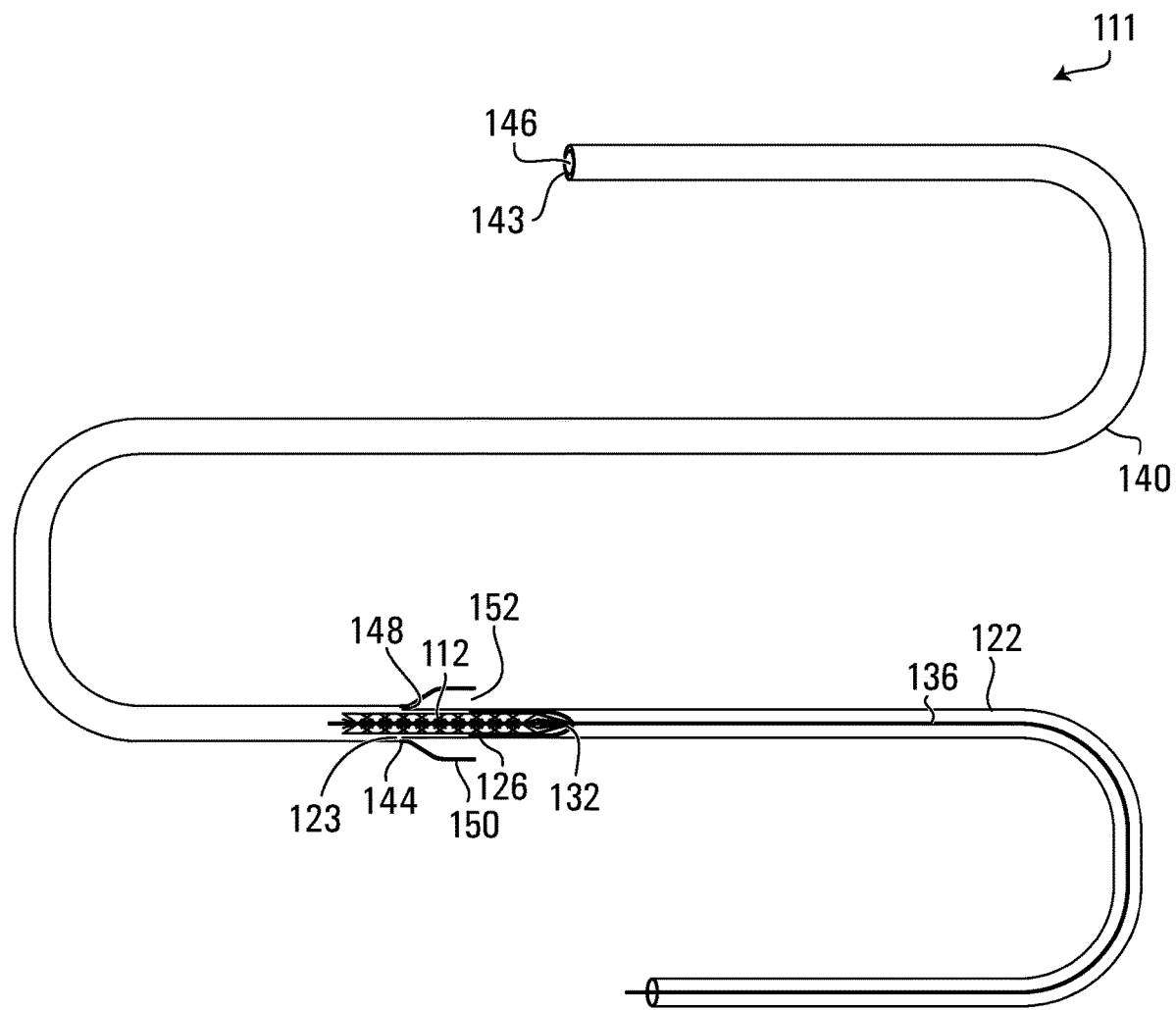
FIG. 5D is a drawing of a system for the deployment of a reversibly compressible endovascular device according to the embodiment illustrated in FIGS. 5A, 5B, and 5C, showing the compressed endovascular device and compressor advanced partially into the delivery catheter through the proximal delivery catheter opening.
Figure 5E:
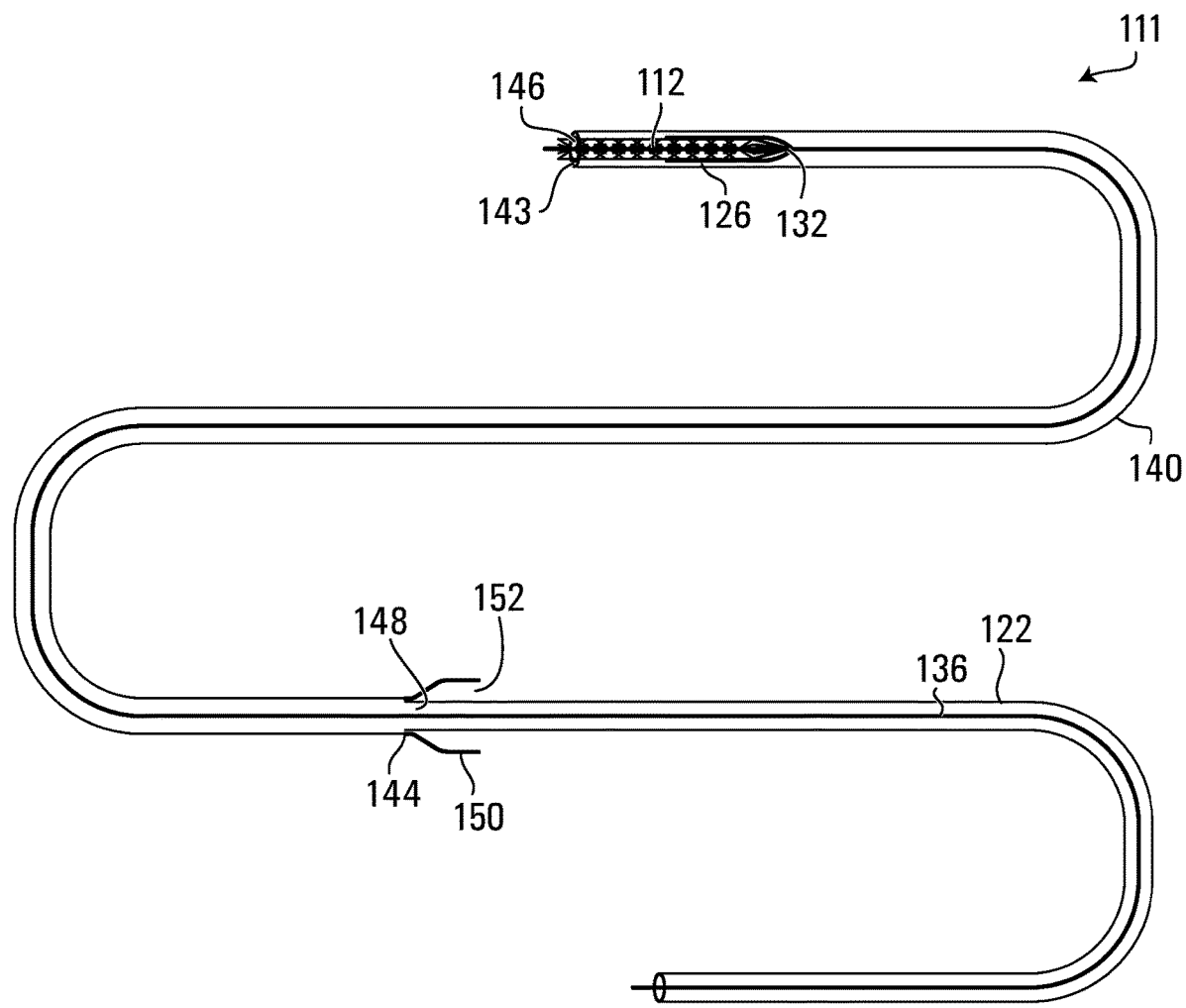
FIG. 5E is a drawing of a system for the deployment of a reversibly compressible endovascular device according to the embodiment illustrated in FIGS. 5A, 5B, 5C, and 5D, showing the compressed endovascular device and compressor advanced to the distal end of the delivery catheter prior to deployment at a target site within a lumen of a subject.
Figure 5F:
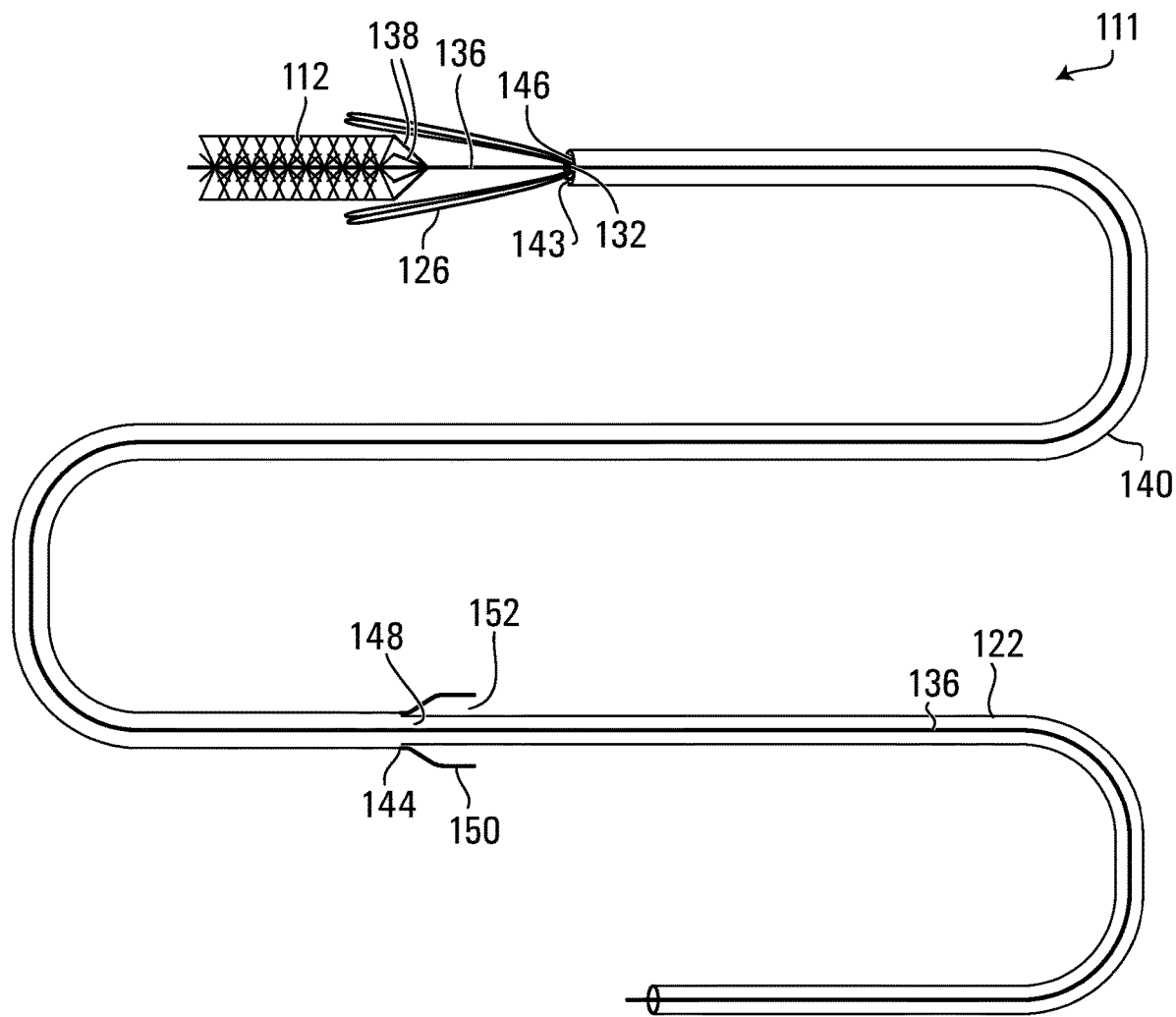
FIG. 5F is a drawing of a system for the deployment of a reversibly compressible endovascular device according to the embodiment illustrated in FIGS. 5A, 5B, 5C, 5D, and 5E showing the endovascular device and compressor advanced out of the distal delivery catheter opening of the delivery catheter and expanded at the target site within the lumen of a subject.
Figure 5G:
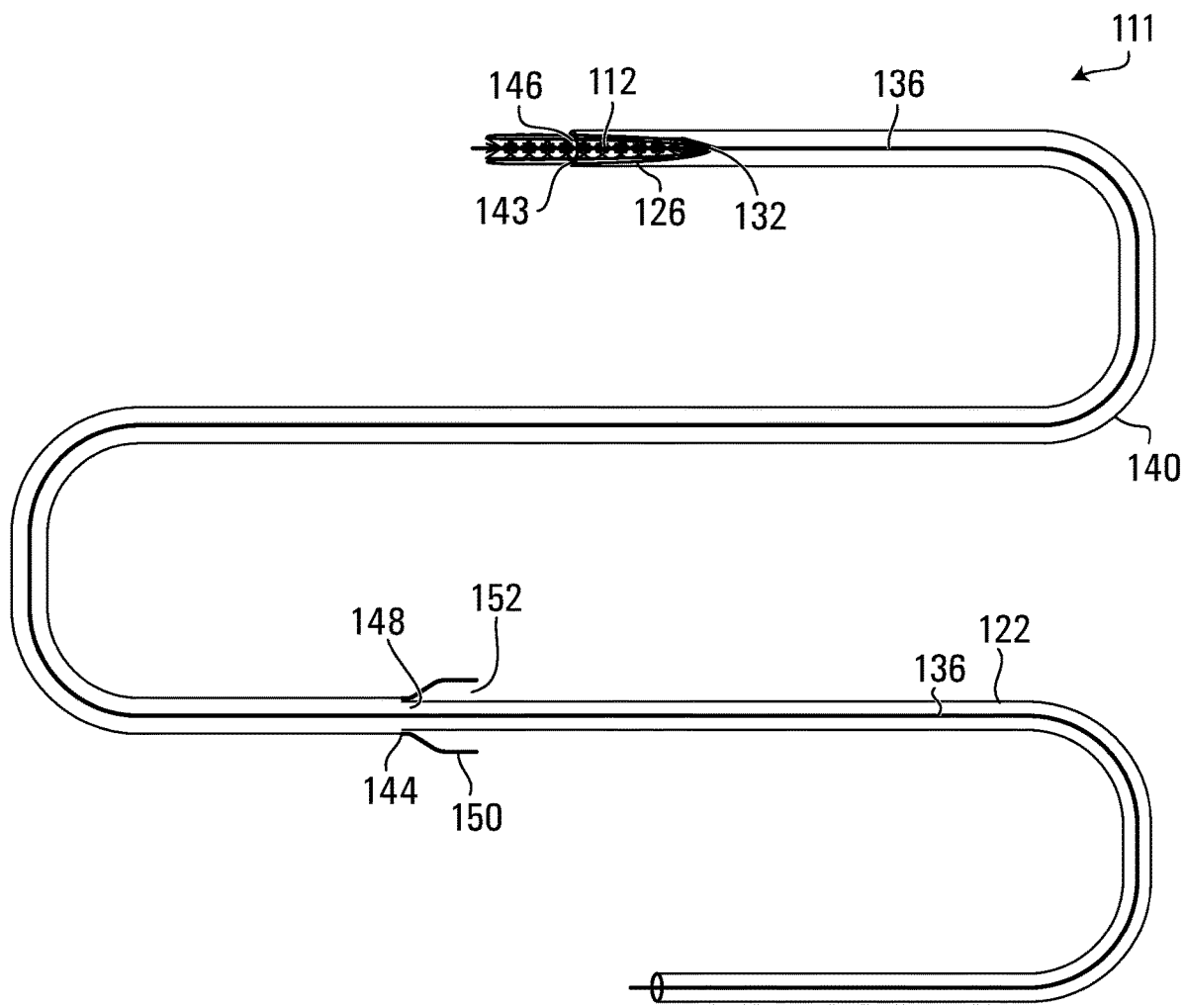
FIG. 5G is a drawing of a system for the deployment of a reversibly compressible endovascular device according to the embodiment illustrated in FIGS. 5A, 5B, 5C, 5D, 5E, and 5F showing the retraction of an initially deployed endovascular device and compressor into the delivery catheter through the distal delivery catheter opening.

Referring to FIGS. 5F and 5G push wire 136 is operable to be advanced distally through delivery sheath 122 and delivery catheter 140 to urge compressor 126 and ED 112 out from the delivery sheath through delivery sheath opening and into delivery catheter through proximal delivery catheter opening 148, and through the delivery catheter distally toward and out distal delivery catheter opening 146 into the lumen. Referring to FIG. 5F, once in the lumen at the target site and unconstrained by delivery catheter 140, compressor 126 may be expanded from its collapsed position. This, in turn, permits ED 112 to be expanded to its non-compressed position at the target site.

In embodiments where the compressor is a self-expanding compressor, expanding compressor 126 in the lumen involves allowing the compressor to self-expand. In embodiments where the ED is a self-expanding ED, expanding ED 112 in the lumen similarly involves allowing the ED to self-expand to a non-compressed position. It will be within the purview of a skilled person to select and employ an appropriate means of expanding a compressor or an ED. For example, alternatives for expanding the ED, and/or the compressor, may include inflating a balloon disposed within the tubular body of the ED to expand the ED.

Once in its non-compressed position at the target site, threads 138 may be detached from ED 112, and the delivery catheter may then be repositioned for the deployment of a further ED, or removed. Alternatively, if the embodiment relies on frictional engagement of the compressor with the ED as depicted in FIG. 4B, then there is no need to detach any threads.

Alternatively, in embodiments employing threads, it may be desirable to reposition an ED before the threads are detached. In such embodiments, and referring to FIG. 5G push wire 136 is operable to be retracted proximally toward hub 150 to urge deployed ED 112 and expanded compressor 126 back toward the distal delivery catheter opening 146, wherein collapse of compressor 126 upon reception within delivery catheter 140, as with previous reception within delivery sheath 122, exerts a radial force upon ED 112 sufficient to compress the ED for reception in the delivery catheter.

In operation, delivery catheter 140 will typically be deployed in a vessel of a subject, such that distal delivery catheter end 143 is positioned at a target site, with hub 150 remaining outside of the body of the subject. ED 112 is loaded in delivery sheath 122 as described above with reference to FIGS. 3, 4A, and 4B. Referring to FIG. 5C, distal end 123 of delivery sheath 122, with ED 112 compressed within it, is then inserted in hub 150. Delivery sheath opening 124 is then registered with proximal delivery catheter opening 148. Referring to FIGS. 5D and 5E, push wire 136 is then used to advance compressor 126 and ED 112 distally through the delivery sheath opening 124 into delivery catheter 140 through proximal delivery catheter opening 148, and then distally through the delivery catheter toward distal delivery catheter opening 146. Referring to FIG. 5F, compressor 126 and ED 112 are then advanced through distal delivery catheter opening 146 into the lumen of the vessel where the compressor is expanded to its non-collapsed position. With the expansion of the compressor 126, ED 112 may be expanded in the lumen at the target site.

In embodiments where the ED is a self-expanding ED, expanding ED 112 in the lumen involves allowing the ED to self-expand. It will be within the purview of a skilled person to select and employ an appropriate means of expanding an ED. For example, alternatives for expanding the ED may include inflating a balloon disposed within the tubular body of the ED to expand the ED.

Referring to FIG. 5G, if repositioning of ED 112 is desired, push wire 136 is retracted proximally through delivery catheter 140 to urge reversibly collapsible compressor 126 back through distal delivery catheter opening 146 to collapse compressor 126. As with previous loading within delivery sheath 122, as compressor 126 collapses, it exerts a radial force upon ED 112 to compress the ED into a compressed position for reception in delivery catheter 140. Delivery catheter 140 is then repositioned to a second position at target site, or to a second target site. Push wire 136 is again advanced distally to urge compressor 126 and ED 112 out of delivery catheter 140 and into the lumen through distal delivery catheter opening 146. Once compressor 126 is outside of delivery catheter 140, it may again be expanded, thereby allowing ED 112 to be expanded at the second position. Once ED 112 has been satisfactorily positioned within the lumen, threads 138 (as depicted in FIG. 5F) may be detached.

The delivery catheter may then be repositioned for the deployment of a further ED, or removed.

Compressors Moveable Independently of Endovascular Devices

Figure 6A:
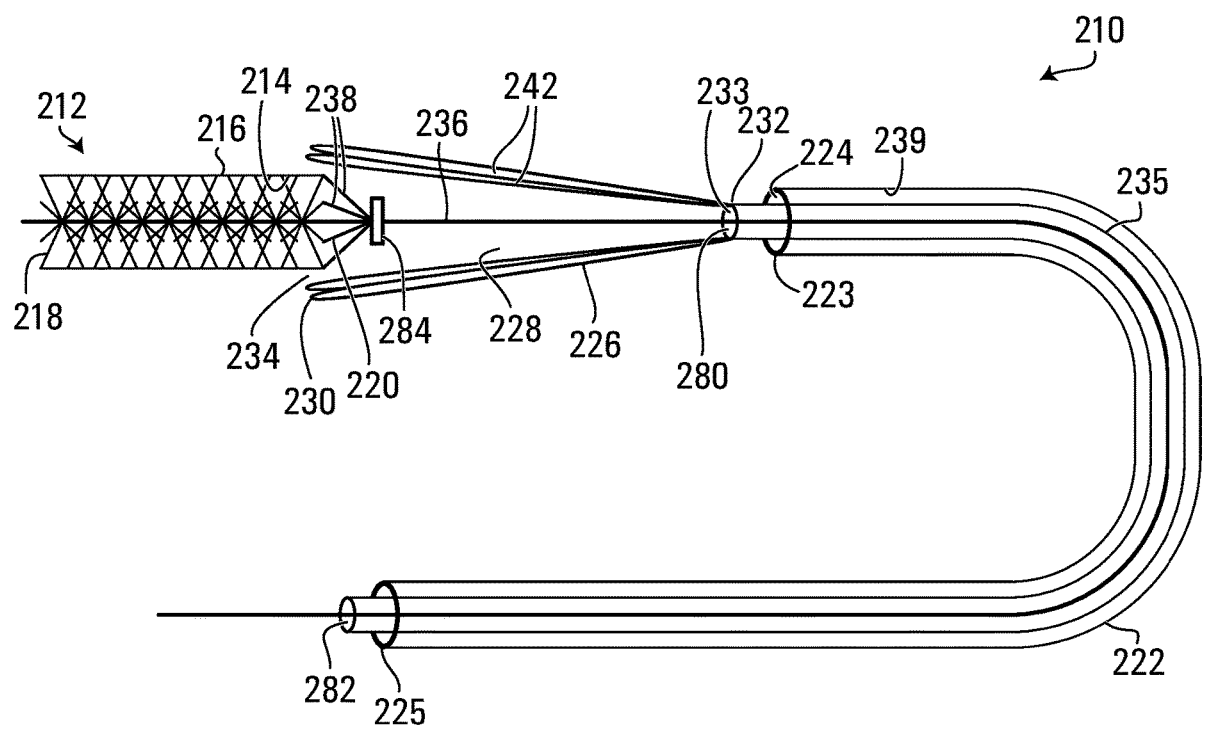
FIG. 6A is a drawing of a system for the radial compression of a reversibly compressible endovascular device prior to deployment according to a fourth embodiment of the invention involving a collapsible compressor that is moveable independent of the endovascular device.

Referring to FIG. 6A, a system for the radial compression of a reversibly compressible endovascular device (ED) prior to deployment according to a fourth embodiment of the invention is shown generally at 210. The system includes a reversibly compressible ED 212 as are generally known in the art. In general, the ED comprises a tubular body that is expandable between a non-compressed position, as depicted in FIG. 6A, and compressed position for loading within a catheter for delivery to a target site in the lumen of a vessel within the body of a subject. The tubular body has an inner surface 214, an outer surface 216, and opposed distal and proximal ED openings 218 and 220.

The system further includes a delivery sheath 222 sized to receive and maintain the ED 212 in the compressed position upon reception in the delivery sheath 222 in the compressed position. Delivery sheath 222 has a distal delivery sheath end 223 having a delivery sheath opening 224. Delivery sheath opening 224 has a width sized to receive the ED 212 into delivery sheath 222 in a compressed form. Delivery sheath 222 further has a proximal delivery sheath end 225.

The system further includes a compressor 226 for radially compressing the ED 212 for reception by the delivery sheath 222 through the delivery sheath opening 224. The compressor includes a generally tapered structure defining an interior space 228 in which ED 212 initially is at least partially positioned in a non-compressed position. The tapered structure comprises distal and proximal compressor ends 230 and 232.

Distal compressor end 230 comprises a distal compressor opening 234 sized to receive ED 212 in the non-compressed position. As illustrated in FIG. 6A, compressor 226 tapers from distal compressor opening 234 toward proximal compressor end 232 such that the radial cross section of the interior space 228 diminishes from distal compressor end 230 toward proximal compressor end 232. The width of proximal compressor end 232 is less than the width of delivery sheath opening 224 such that proximal compressor end 232 is sized to be received within delivery sheath 222 as discussed below.

Compressor 226 is collapsible, such that as it collapses, the cross sectional area of interior space 228 at any position along the longitudinal axis of the compressor from distal compressor end 230 to proximal compressor end 232 progressively decreases. As the cross sectional area of interior space 228 decreases, compressor 226 exerts a radial force against ED 212 positioned therein to compress the ED.

Compressor 226 is sized to be received, in collapsed form, within delivery sheath 222 through delivery sheath opening 224. ED 212, being compressed within interior space 228 as compressor 226 collapses, is thereby compressed for reception within delivery sheath 222.

The system further comprises means for urging compressor 226 and ED 212 proximally toward distal delivery sheath end 223 and into delivery sheath 222 through delivery sheath opening 224. The means for urging the compressor and the ED 212 proximally (or distally as the case may be) may further comprise independent means for urging the ED independently of the compressor.

Referring still to FIG. 6A, the means for urging compressor 226 and ED 212 according to this particular embodiment include a compressor wire 235 that is attached to proximal compressor end 232, which may be drawn proximally toward proximal delivery sheath end 225 to urge compressor 226 toward distal delivery sheath end 223. In this embodiment, compressor wire 235 is a hollow, tubular wire having distal and proximal compressor wire openings 280 and 282. Distal compressor wire opening 280 is in communication with a proximal compressor opening 233 at proximal compressor end 232.

In the embodiment illustrated in FIG. 6A, the means for urging compressor 226 and ED 212 further comprises a push wire 236 that is attached to the ED, but is not attached to the compressor. Push wire 236 is positioned within compressor wire 235 and extends through distal compressor wire opening 280 and proximal compressor opening 233, and is detachably attached to ED 212. Push wire 236 is attached to ED 212 by at least one (i.e. one or more) threads 238. In FIG. 6A, threads 238 are shown radiating from push wire 236 and attached to ED 212 at proximal ED opening 220. However, the skilled person understands that threads 238 may be attached to ED 212 at a different position, for example, to inner surface 214 or outer surface 216. In some embodiments, threads 238 could be attached at distal ED opening 218. In some embodiments, the at least one thread is a single thread comprising a lasso, wherein the lasso is looped and tightened around the tubular body of the ED proximal to proximal ED opening to form a cincture about the proximal end of the ED.

As discussed above in respect of the first and second embodiments, threads 238 may be electrolytically or mechanically detachable from ED 212 once the ED is positioned at the target site within the lumen of the vessel, as is known in the field. In embodiments involving a lasso-style attachment, the loop of the lasso may be broken to release ED. Threads 238 may be made of any suitable materials as are known in the field, including wires.

Thus, the skilled person will understand that compressor wire 235 and push wire 236 allow for the compressor 226 and the ED 212 to be moved independently of each other. For example, as described below, in situations where it is not desirable to deploy the compressor 226 into the lumen of vessel at the target site, push wire 236 may be advanced distally while compressor wire 235 is maintained in position or advanced proximally.

Referring again to FIG. 6A, the means for urging ED 212 further comprise a bump member 284 disposed on push wire 236 between threads 238 and proximal compressor opening 233. When compressor wire 235 is held in a static position, or retracted proximally through delivery sheath 222, while push wire 236 is advanced distally, bump member 284 abuts the proximal end of ED 212 at ED opening 220 to apply a force uniformly across the circumference of the ED 212 at the proximal end opening to urge the ED distally while the compressor 226 remains in position or is retracted proximally. In this way, ED 212 may be disengaged from the compressor 226.

In the illustrated embodiment, the bump member abuts the proximal end of ED 212 to urge the ED distally as push wire 236 is advance distally. However, the skilled person will understand that the bump member could be positioned at least partially within the ED through the proximal ED opening, such that a radially outer surface of the bump member can engage, e.g. frictionally engage, the inner surface of the ED, e.g. inner surface 214 of ED 212 to urge the ED distally as push wire 236 is advance distally. A skilled person will appreciate that a number of bumper structures could be used in the context of the presently disclosed invention in combination with a push wire to urge an ED distally independently of a compressor. For example, the skilled person will be aware of bumps, including a dual function bump, as disclosed in U.S. Pat. No. 10,292,851. Alternatively, a stent bed as described in U.S. Pat. No. 10,555,824 could be used as a bumper in the context of the presently disclosed invention.

Figure 6B:
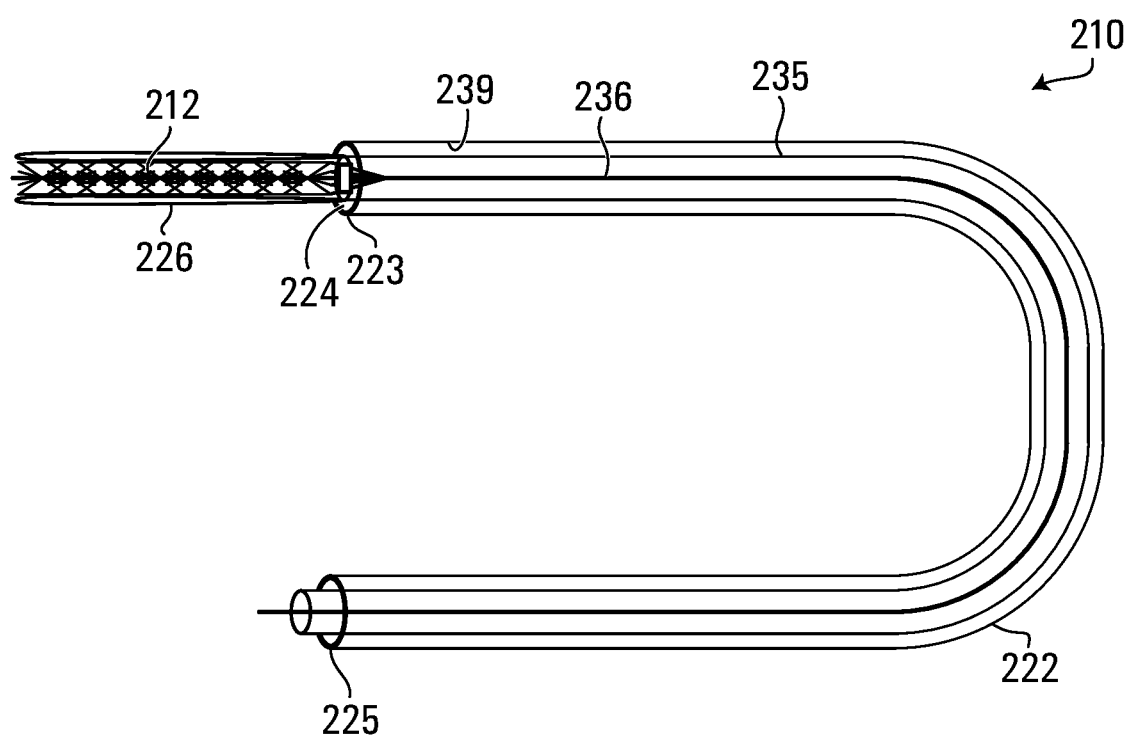
FIG. 6B is a drawing of the system depicted in FIG. 6A with the compressor and endovascular device partially received within the delivery sheath.

Referring to FIG. 6B, compressor wire 235 and push wire 236 are operable to be retracted proximally in conjunction through delivery sheath 222 toward proximal delivery sheath end 225 to urge compressor 226 into delivery sheath 222 through delivery sheath opening 224. In various embodiments, an inner wall 239 of delivery sheath 222 is operable to exert a force against the outer surface of compressor 226, as compressor 226 is received within the delivery sheath 222, that is sufficient to collapse the tapered structure.

As depicted in FIG. 6A, compressor 226 may take the general form of a funnel. In some embodiments, as depicted in FIG. 6A, compressor 226 comprises a plurality of overlapping tongues 242 coupled at proximal compressor end 232, wherein each tongue 242 tapers toward the proximal compressor end. Each tongue 242 is slidable over an adjacent tongue to change the cross sectional area of interior space 228 as the compressor 226 is collapsed or expanded.

However, the skilled person will again understand that collapsible compressors according to the present disclosure could include a variety of radially compressible structures that, when at least partially received within the delivery sheath, form a tapered structure that can accommodate an ED in noncompressed form and, as urged into the delivery sheath along with the ED, collapse to compress the ED to a compressed form. Such compressors could be formed of a braided structure, for example, a polypropylene braided or a metal braided structure as is known in the art and used in some cases for the fabrication of EDs themselves.

In various embodiments, compressor 226 is reversibly collapsible. For example, compressor 226 may be resiliently deformable such that, after reception in delivery sheath 222, it may be urged distally using compressor wire 235 from the delivery sheath into a delivery catheter, and then out of the delivery catheter through a distal delivery catheter opening (e.g. into the lumen of a vessel), at which time it will expand to a non-collapsed formation to permit release of ED 212 at the target site. Alternatively, the tapered structure may be actively expanded upon emergence from a delivery catheter opening by any means known in the art, e.g. using a balloon.

Alternatively, push wire 236 may be used to urge ED 212 distally independently of compressor 226, such that compressor 236 may remain in delivery sheath 222 (or delivery catheter, as the case may be) while ED 212 is advanced through a delivery catheter for deployment at a target site In operation, starting with ED 212 in an expanded position, retracting compressor wire 235 and push wire 236 into delivery sheath 222 toward proximal delivery sheath end 225 urges compressor 226 into delivery sheath 222 through delivery sheath opening 224. As tapered structure is urged into delivery sheath, the cross sectional area of interior space 228 at any position along the longitudinal axis of the compressor from distal compressor end 230 to proximal compressor end 232 is progressively reduced, wherein compressor 226 exerts a radial force against ED 212 positioned therein to radially compress the ED for reception within delivery sheath 222 through delivery sheath opening 224.

Deployment

Once ED 212 has been received within delivery sheath 222 in a compressed position, the delivery sheath 222 can be used in conjunction with a delivery catheter for delivery of the ED to the target site.

Referring to FIGS. 7A, 7B, 7C, and 7D, a system for deploying a reversibly compressible endovascular device within a lumen of a vessel is shown generally at 211. The system comprises a system for the radial compression of a reversibly compressible endovascular device (ED) prior to deployment as described above with reference to FIGS. 6A and 6B. The system further comprises a delivery catheter 240 having distal and proximal delivery catheter ends 243 and 244 having distal and proximal delivery catheter openings 246 and 248, respectively. Proximal delivery catheter opening 248 is for receiving ED 212 (and optionally compressor 226, as the case may be) from delivery sheath 222 in a compressed position, whereas distal delivery catheter opening 246 is for deploying ED 212 (and optionally compressor 226, as the case may be) into the lumen of the vessel. Accordingly, proximal delivery catheter opening 248 is of a width equal to or greater than the width of delivery sheath opening 224.

The system further comprises a hub 250 connected to proximal delivery catheter end 244 and in communication with proximal delivery catheter opening 248. Hub 250 has hub opening 252 for receiving delivery sheath 222 in hub 250 when compressor 226 and ED 212 are positioned in the delivery sheath. Hub 250 is for positioning delivery sheath opening 224 in abutment with proximal delivery catheter opening 248.

Figure 7A:
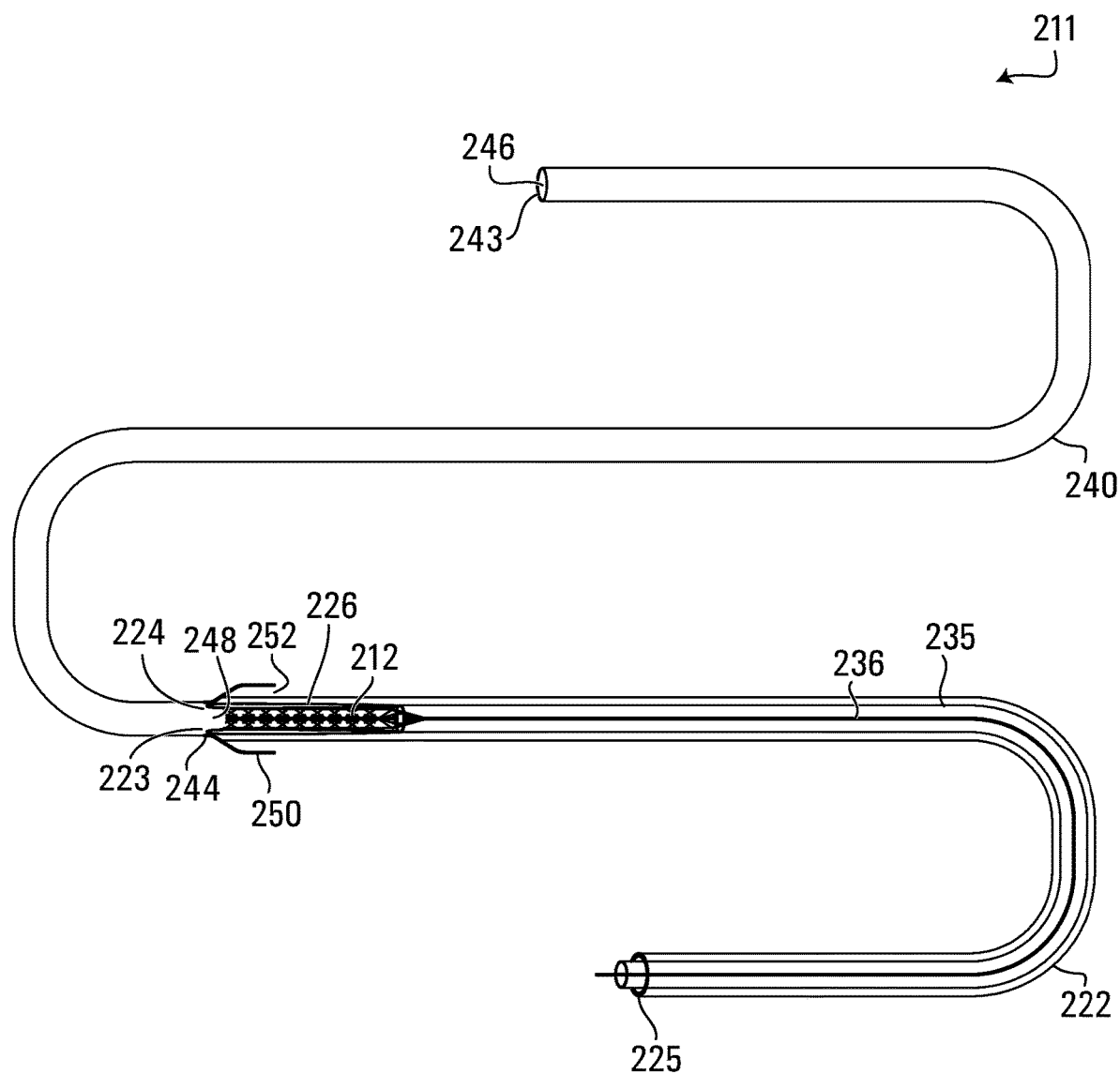
FIG. 7A is a drawing of a system for the deployment of a reversibly compressible endovascular device according to an embodiment of the invention involving a collapsible compressor as depicted in FIGS. 6A and 6B.
Figure 7B:
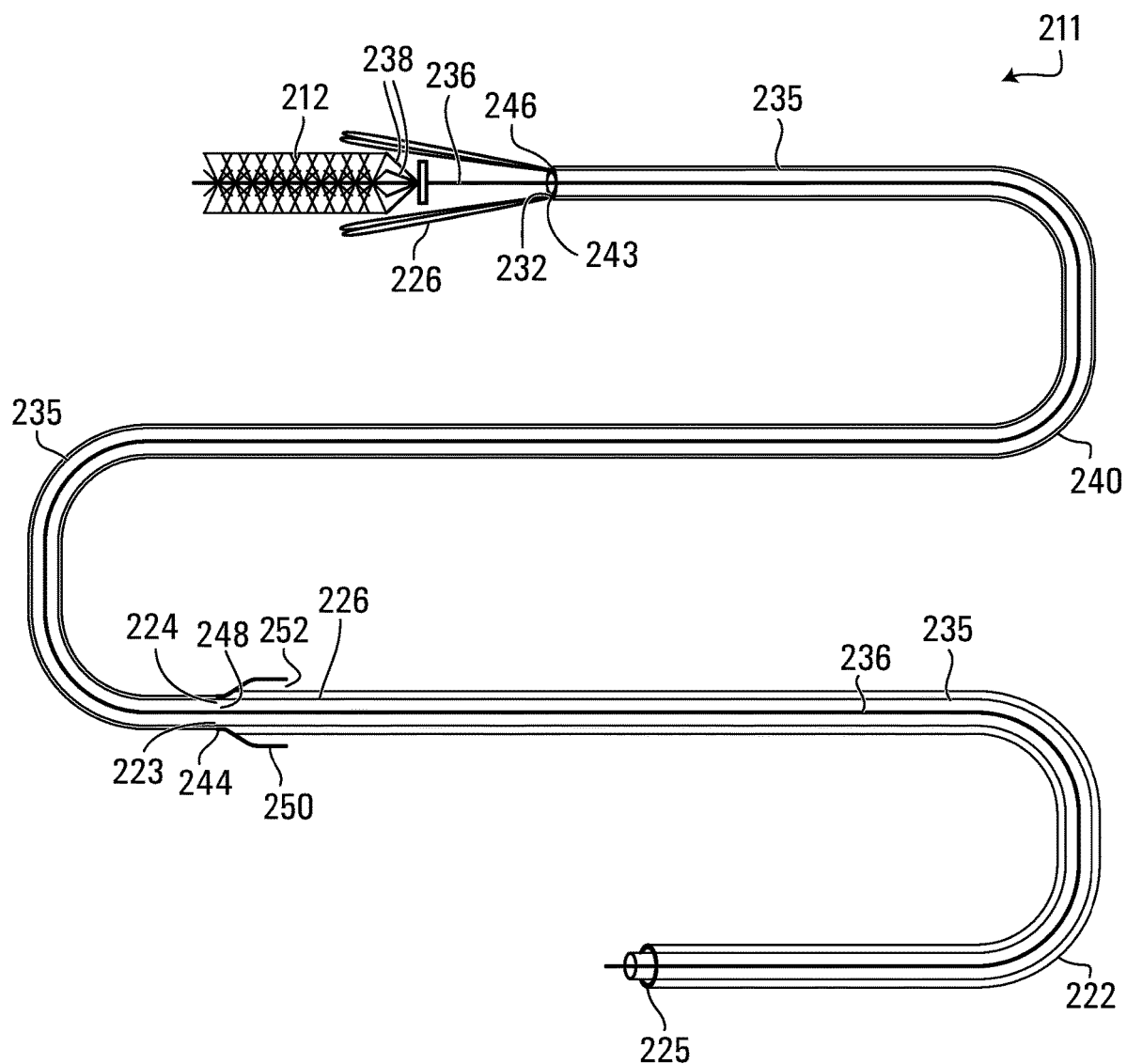
FIG. 7B is a drawing of a system for the deployment of a reversibly compressible endovascular device to the embodiment illustrated in FIG. 7A wherein the endovascular device and compressor are advanced out of the delivery catheter and into the lumen of a vessel.

Referring to FIG. 7B, compressor wire 235 and push wire 236 are operable to be advanced distally through delivery sheath 222 and delivery catheter 240 to urge compressor 226 and ED 212 from the delivery sheath and into the delivery catheter through proximal delivery catheter opening 248, and through the delivery catheter distally toward and distal catheter opening 246. Compressor 226 and ED 212 can then be advanced out distal catheter opening 246 into the lumen of a vessel of a patient. Once in the lumen at the target site and unconstrained by delivery catheter 240, compressor 226 may be expanded from its collapsed position. This, in turn, permits ED 212 to be expanded to its non-compressed position at the target site.

In embodiments where the compressor is a self-expanding compressor, expanding compressor 226 in the lumen involves allowing the compressor to self-expand. In embodiments where the ED is a self-expanding ED, expanding ED 212 in the lumen similarly involves allowing the ED to self-expand to a non-compressed position. It will be within the purview of a skilled person to select and employ an appropriate means of expanding a compressor or an ED. For example, alternatives for expanding the ED may include inflating a balloon disposed within the tubular body of the ED to expand the ED.

Figure 7C:
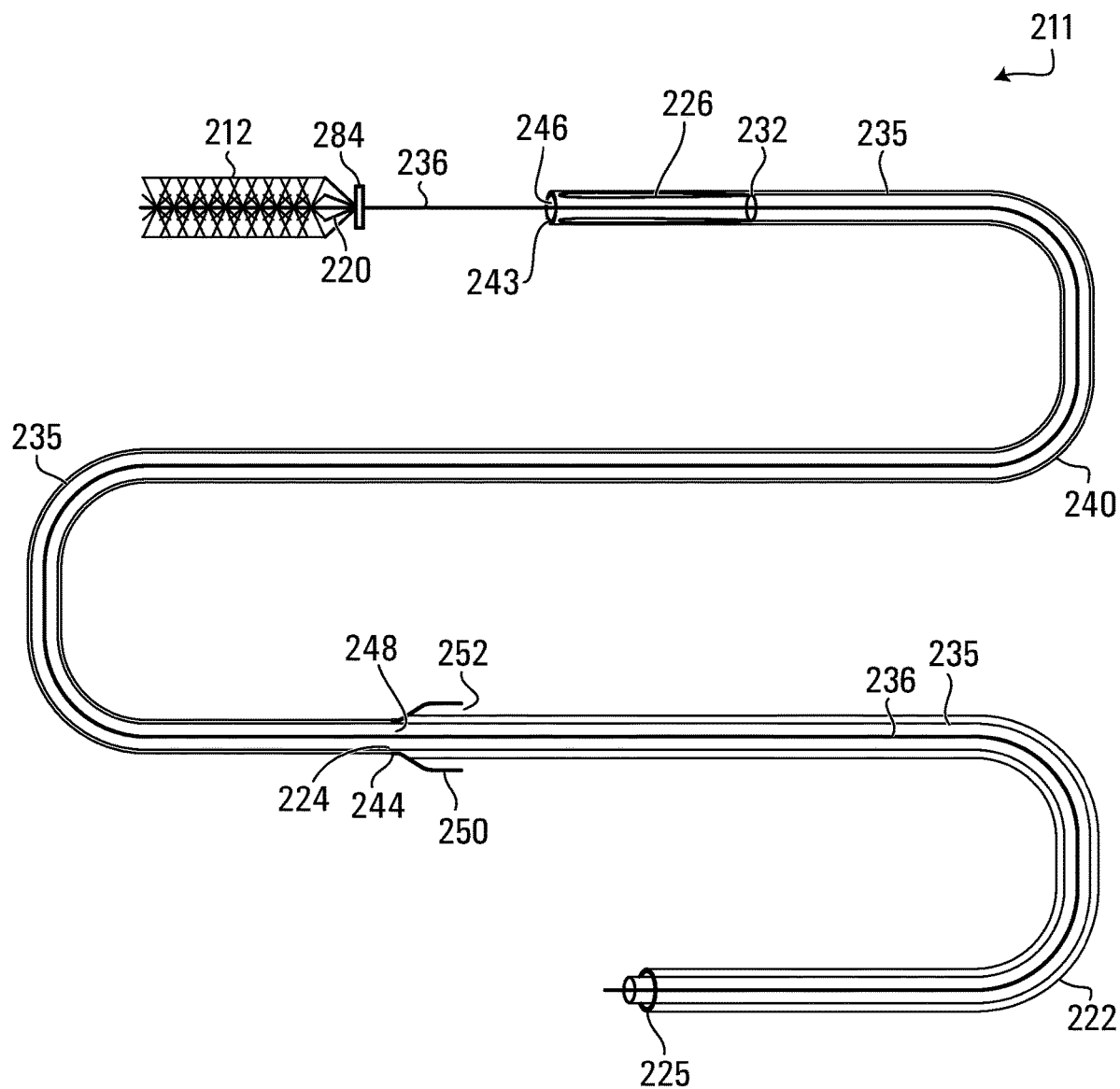
FIG. 7C is a drawing of a system for the deployment of a reversibly compressible endovascular device to the embodiment illustrated in FIG. 7A wherein the endovascular device is advanced out of the delivery catheter and into the lumen of a vessel while the compressor is retained within the delivery catheter.

Alternatively, referring to FIG. 7C, once ED 212 and compressor 226 have been advanced distally to distal delivery catheter end 242, push wire 236 can be used to urge ED 212 independently of compressor 226 out distal delivery catheter opening 246 into the lumen, where ED 212 may expand to its non-compressed position at the target site, while the compressor is retained within delivery catheter 240.

Figure 7D:
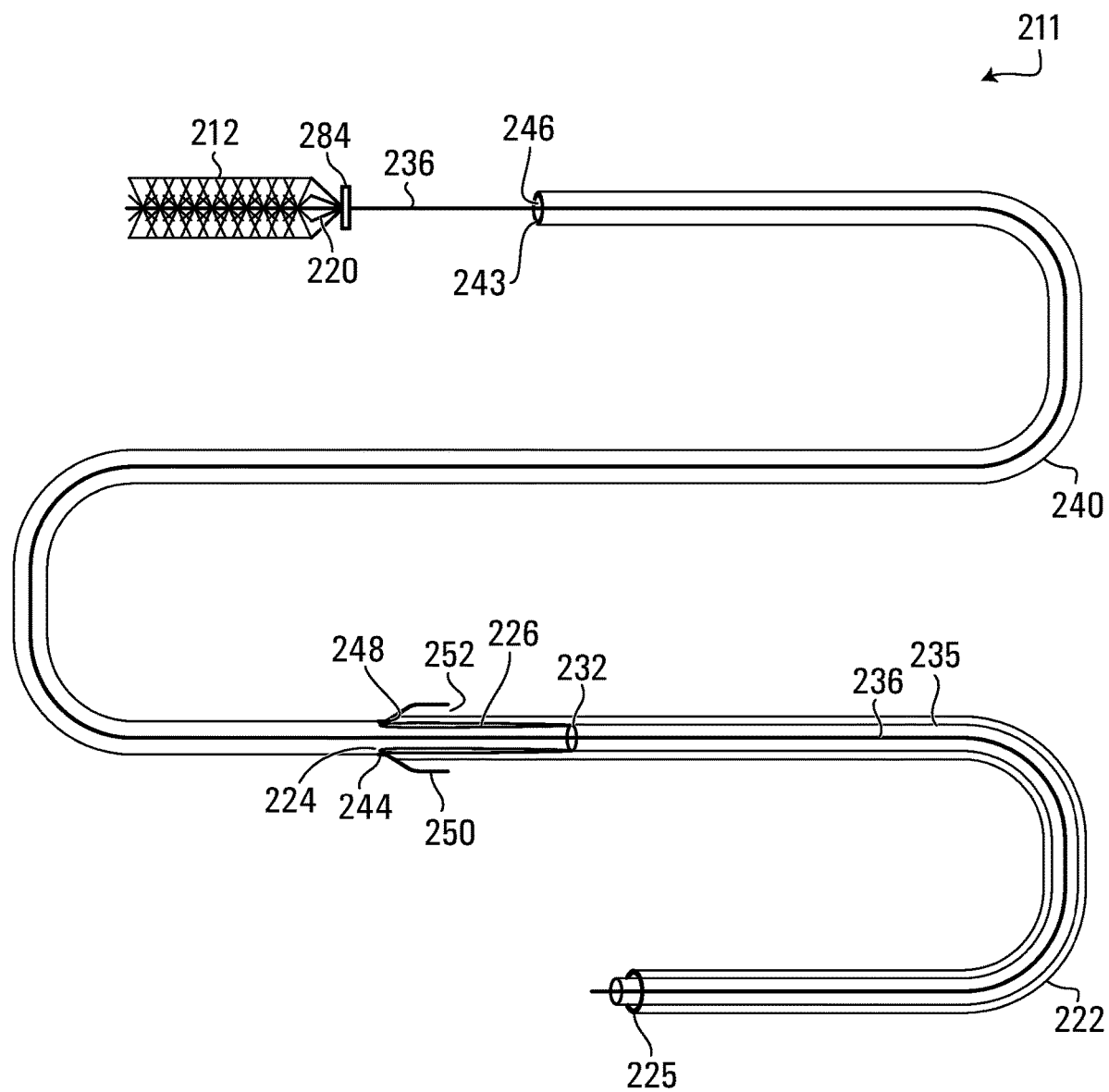
FIG. 7D is a drawing of a system for the deployment of a reversibly compressible endovascular device to the embodiment illustrated in FIG. 7A wherein the endovascular device is advanced out of the delivery catheter and into the lumen of a vessel while the compressor is retained within the delivery sheath.

Yet alternatively, and referring to FIG. 7D, push wire 236 is operable to be advanced distally through delivery sheath 222 and delivery catheter 240 independently of compressor wire 235 to advance ED 212 from the delivery sheath and into the delivery catheter through proximal delivery catheter opening 248, and through the delivery catheter distally toward distal delivery catheter opening 246, while compressor 226 is retained in delivery sheath 222. When push wire 236 is advanced distally, bump member 284 abuts the proximal end of ED 212 at proximal ED opening 220 to apply a force uniformly across the circumference of the ED at the proximal end to urge ED 212 distally while compressor 226 remains in position or is retracted proximally. Once in delivery catheter 240, ED 212 can then be advanced distally out distal catheter opening 246 into the lumen where ED 212 may expand to its non-compressed position at the target site.

Once in its non-compressed position at the target site, threads 238 may be detached from ED 212, and delivery catheter 240 may then be repositioned for the deployment of a further ED, or removed from the patient.

Alternatively, in embodiments employing threads and a compressor that is deployed within the lumen, it may be desirable to reposition an ED before the threads are detached. In such embodiments, compressor wire 235 and push wire 236 are operable to be retracted proximally toward hub 250 to urge deployed ED 212 and expanded compressor 226 back toward the distal delivery catheter opening 246, wherein collapse of compressor 226 upon reception within delivery catheter 240, as with previous reception within delivery sheath 222, exerts a radial force upon ED 212 sufficient to compress the ED for reception in the delivery catheter.

In operation, delivery catheter 240 will typically be deployed in a vessel of a subject, such that distal delivery catheter end 242 is positioned at a target site, with hub 250 remaining outside of the body of the subject. ED 212 is loaded in delivery sheath 222 as described above with reference to FIGS. 6A and 6B. Referring to FIG. 7A, distal end 223 of delivery sheath 222, with ED 212 compressed within it, is then inserted in hub 250. Delivery sheath opening 224 is then registered with proximal delivery catheter opening 248.

Referring to FIG. 7B, compressor wire 235 and push wire 236 are then used to advance compressor 226 and ED 212 through the delivery sheath opening 224 into delivery catheter 240 through proximal delivery catheter opening 248, and then distally through the delivery catheter toward distal delivery catheter end 242. Compressor 226 and ED 212 are then advanced through distal delivery catheter opening 246 into the lumen of the vessel where the compressor is expanded to its non-collapsed position. With the expansion of compressor 226, ED 212 may be expanded in the lumen at the target site.

Alternatively, referring to FIG. 7C, once ED 212 and compressor 226 are advanced to distal delivery catheter end 243, push wire 236 may be used to urge ED 212 through distal delivery catheter opening 246 independently of compressor 236 (which is held in position or retracted proximally using compressor wire 235) and into the lumen of the vessel where ED 212 may be expanded in the lumen at the target site while compressor 236 remains in the delivery catheter.

Alternatively, and referring to FIG. 7D, once delivery sheath opening 224 is registered with proximal delivery catheter opening 248, push wire 236 is used to advance ED 212, independently of compressor 236, through the delivery sheath opening 224 into delivery catheter 240 through proximal delivery catheter opening 248, and then distally through the delivery catheter toward distal delivery catheter end 243. ED 212 is then advanced through distal delivery catheter opening 246 into the lumen of the vessel where ED 212 may be expanded in the lumen at the target site while compressor 236 remains in delivery sheath 222.

In embodiments where the ED is a self-expanding ED, expanding ED 212 in the lumen involves allowing the ED to self-expand. It will be within the purview of a skilled person to select and employ an appropriate means of expanding an ED. For example, alternatives for expanding the ED may include inflating a balloon disposed within the tubular body of the ED to expand the ED.

In embodiments where compressor 236 is deployed into the lumen, if repositioning of the ED is desired, compressor wire 235 and push wire 236 are retracted proximally through delivery catheter 240 to urge reversibly collapsible compressor 226 and ED 212 back through distal delivery catheter opening 246 to collapse compressor 226. As with previous loading within delivery sheath 222, as compressor 226 collapses, it exerts a radial force upon ED 212 to compress the ED into a compressed position for reception in delivery catheter 240. Delivery catheter 240 is then repositioned to a second position. Compressor wire 235 and push wire 236 are again advanced distally to urge compressor 226 and ED 212 out of delivery catheter 240 and into the lumen through distal delivery catheter opening 246. Once compressor 226 is outside of delivery catheter 240, it may again be expanded, thereby allowing ED 212 to be expanded at the second position. Once the ED 212 has been satisfactorily positioned within the lumen, threads 238 may be detached.

The delivery catheter may then be repositioned for the deployment of a further ED, or removed.

Direct Loading of Endovascular Device Within Delivery Catheter

The skilled person will understand that, in some embodiments, it may not be necessary to initially load an ED within a delivery sheath prior to loading the compressed ED within a delivery catheter. Rather, an ED could be directly loaded into the distal end of a delivery catheter.

For example, in a conventional method of introducing an ED into the lumen of a vessel, a multi-catheter system, e.g. a triaxial system, is employed. Typically, a guide catheter having proximal and distal guide catheter openings is introduced into a vessel of a patient through the skin. The guide catheter is advanced within the vessel until the distal guide catheter opening is proximal to the target site in the vessel. An intermediate catheter having proximal and distal intermediate catheter openings is then advanced through the guide catheter until the distal intermediate catheter opening is at the target site. Finally, a delivery catheter having proximal and distal delivery catheter openings is advanced through the intermediate catheter until the distal delivery catheter opening is at the target site. In such embodiments, delivery catheters could be supplied pre-packaged with a reversibly compressible ED in a non-compressed position for direct loading into the distal end of a delivery catheter, similar to the systems for loading into the distal ends of a delivery sheath as described above with reference to FIGS. 1, 3, 4A, 4B, 6A, and 6B.

Figure 8:
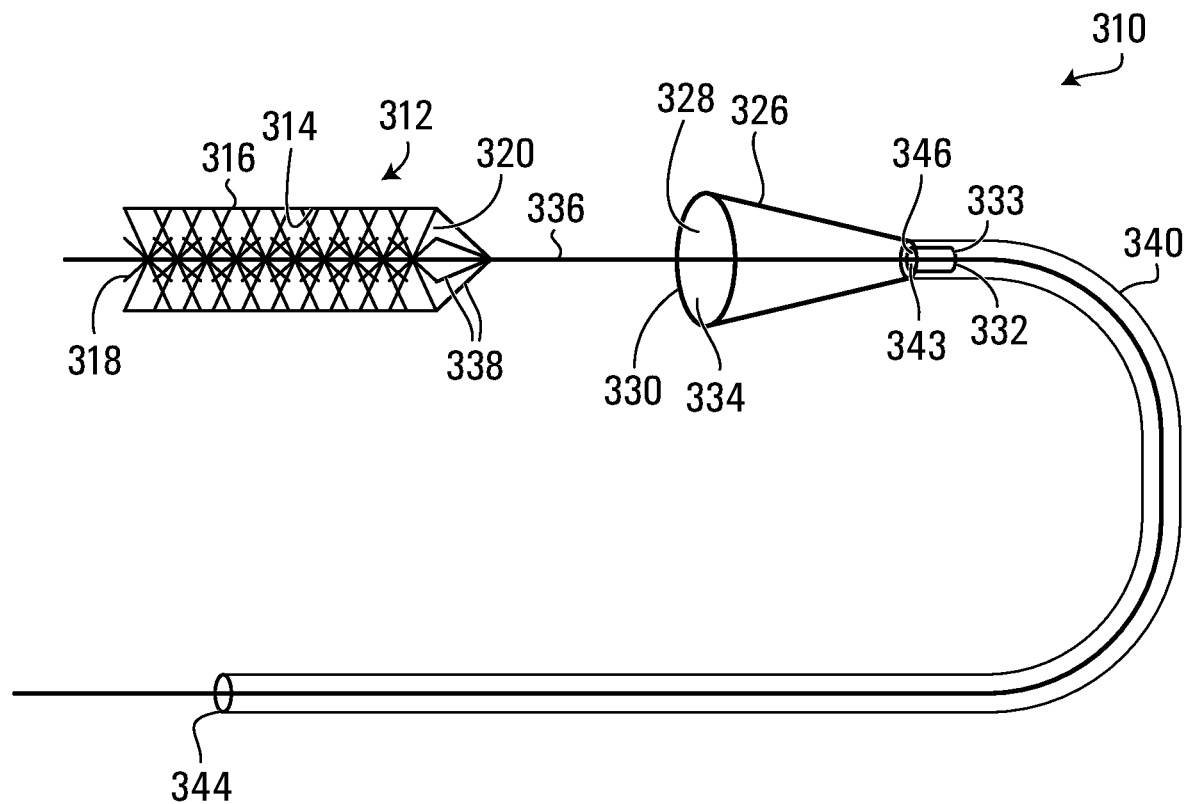
FIG. 8 is a drawing of a system for the radial compression of a reversibly compressible endovascular device directly into a delivery catheter prior to deployment according to a fifth embodiment of the invention.

Accordingly, referring to FIG. 8, a system for the radial compression of a reversibly compressible endovascular device (ED) prior to deployment according to a fifth embodiment of the invention is shown generally at 310. The system includes a reversibly compressible ED 312 as are generally known in the art. In general, the ED comprises a tubular body that is resiliently deformable from a non-compressed position, as depicted in FIG. 8, to a compressed position for loading within a delivery catheter for delivery to a target site in the lumen of a vessel within the body of a subject. The tubular body has an inner surface 314, an outer surface 316, and opposed distal and proximal ED openings 318 and 320.

The system further includes a delivery catheter 340 sized to receive and maintain the ED 312 in the compressed position upon reception in the delivery catheter in the compressed position. Delivery catheter 340 has a distal delivery catheter end 343 having a distal delivery catheter opening 346. Distal delivery catheter opening 346 has a width sized to receive the ED 312 into delivery catheter 340 in a compressed form.

The system further includes a compressor 326 for radially compressing ED 312 for reception by delivery catheter 340 through the distal delivery catheter opening 346. The compressor 326 has a generally tapered structure defining an interior space 328. The tapered structure comprises distal and proximal compressor ends 330 and 332, wherein proximal compressor end 332 is proximal to distal delivery catheter opening 346.

Distal compressor end 330 comprises a distal compressor opening 334 sized to receive the ED 312 in the non-compressed position. As illustrated in FIG. 8, compressor 326 tapers from distal compressor opening 334 toward proximal compressor end 332 such that the radial cross section of the interior space 328 diminishes from distal compressor end 330 toward proximal compressor end 332. Proximal compressor end 332 comprises a proximal compressor opening 333 in communication with distal delivery catheter opening 346. The width of proximal compressor opening 333 is smaller than the radial diameter of the ED 312 when the ED is in the non-compressed position. The radial cross sectional area of interior space 328 proximal at proximal compressor end 332, e.g. at proximal compressor opening 333, is equal to or less than the radial cross sectional area of distal delivery catheter opening 346. In this way, as ED 312 moves through compressor 326, it will be compressed to have a radial cross section less than the radial cross section of the distal delivery catheter opening 346, such that ED 312 can be received within delivery catheter 340 in the compressed position. As such, ED 312, in a compressed form, can be urged through proximal compressor opening 333 and received within delivery catheter 340 through distal delivery catheter opening 346.

The system further comprises a push wire 336 that is detachably attached to ED 312. Push wire 336 is attached to ED 312 by at least one (i.e. one or more) threads 338. In FIG. 8, threads 338 are shown radiating from push wire 336 and attached to ED 312 at proximal ED opening 320. However, the skilled person understands that threads 338 may be attached to ED 312 at a different position, for example, to inner surface 314 or outer surface 316. In some embodiments, threads 338 could be attached at distal ED opening 318.

In some embodiments, the at least one thread is a single thread comprising a lasso, wherein the lasso is looped and tightened around the tubular body of the ED near proximal ED opening to form a cincture about the proximal end of the ED.

Threads 338 may be electrolytically detachable from ED 312 once the ED is positioned at the target site within the lumen of the vessel, as is known in the field. Alternatively, threads 338 may be mechanically detachable from ED 312. It is within the purview of the skilled person to select an appropriate means of detaching threads 338 from the ED. In embodiments involving a lasso-style attachment, the loop of the lasso may be broken to release ED.

Threads 338 may be made of any suitable materials as are known in the field. For example, threads 338 may be made of metal wire.

As shown in FIG. 8, and push wire 336 is disposed within delivery catheter 340, and operable to be advanced proximally through delivery catheter 340 to urge ED 212 through compressor 326, whereby ED 312 is deformed into a compressed position as it is urged through the compressor from distal compressor end 330 to proximal compressor end 332, and further urged through proximal compressor opening 333 into delivery catheter 340 in a compressed position.

As shown in FIG. 8, push wire 336 may also be disposed within ED 312 through proximal ED opening 320.

A depicted in FIG. 8, compressor 326 may take the form of a funnel. In some embodiments, the width of proximal compressor end 332 is smaller than the width of distal delivery catheter opening 346 such that proximal compressor end 332 is sized to be received within delivery catheter 340 through distal delivery catheter opening 346. However, in alternative embodiments, the second compressor end may abut the distal delivery catheter end 343. The skilled person understands that the proximal compressor end and the distal delivery catheter end can be designed to cooperate in numerous different ways, and that it is only important that proximal compressor opening have a width equal to or less than the distal delivery catheter opening so that the ED will be in a sufficiently compressed position to be received within the delivery catheter as the ED approaches the proximal compressor end.

As depicted in FIG. 8, the tapered structure (i.e. compressor 326) may have a unitary (i.e. one-piece) body. In the illustrated embodiment, compressor 326 is removable once ED 312 has been received in a compressed position within delivery catheter 340.

In operation, starting with ED 312 in an expanded position, retracting push wire 336 proximally into delivery catheter 340 urges ED 312 into interior space 328 of compressor 326 via distal compressor opening 334, and toward proximal compressor end 332 to radially compress ED 312 to a compressed (i.e. unexpanded) position as the cross sectional area of interior space 328 diminishes along the longitudinal axis from distal compressor end 330 toward proximal compressor end 332. Further retraction of push wire 336 proximally toward proximal delivery catheter opening 344 urges ED 312 in the compressed position through proximal compressor opening 333 and into delivery catheter 340 through distal delivery catheter opening 346.

Deployment

Once ED 312 has been received within delivery catheter 340 in a compressed position, the delivery catheter can be used in conjunction with a multi-catheter system as described above for delivery of the ED to the target site.

Figure 9A:
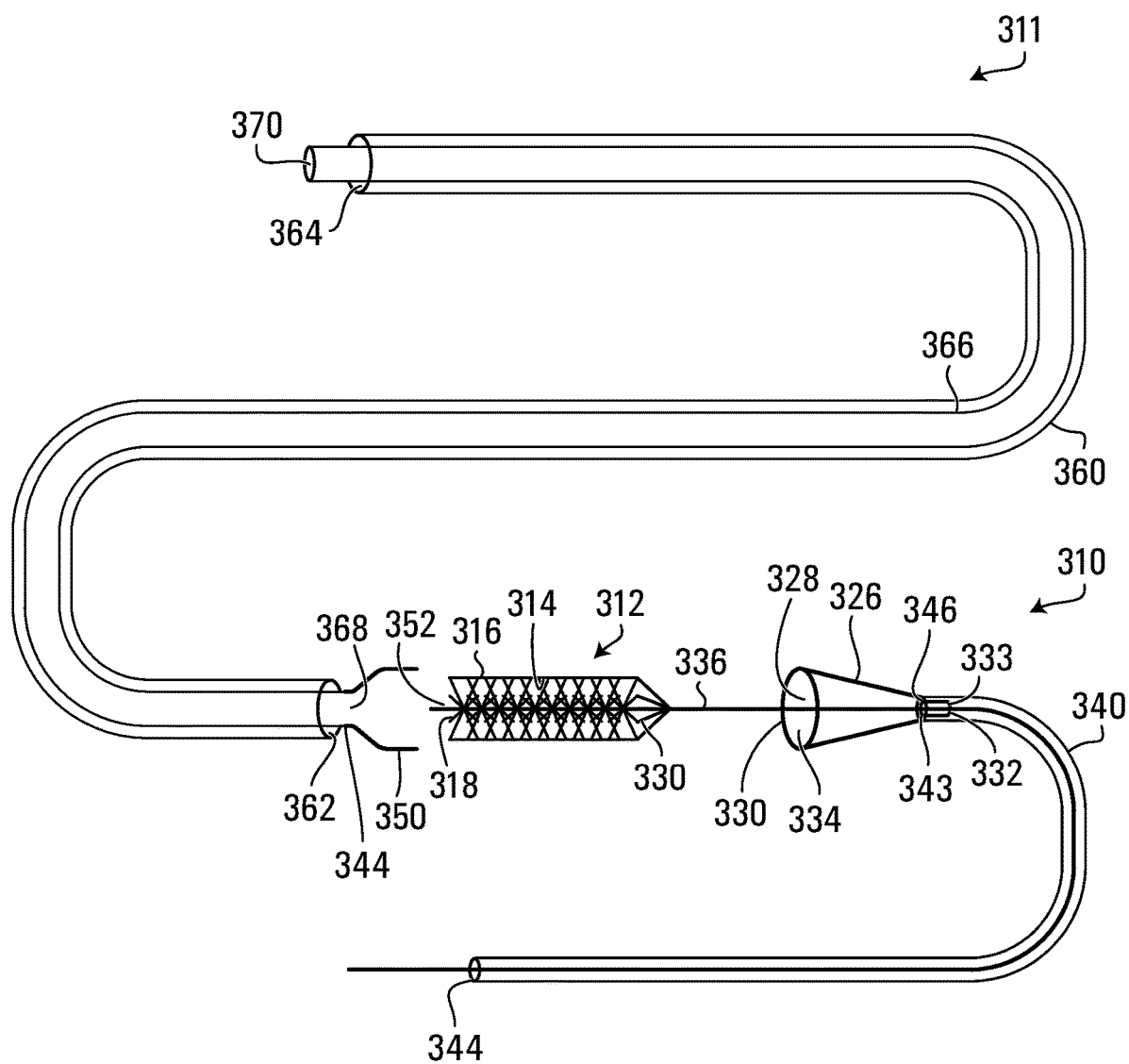
FIG. 9A is a drawing of a system for the deployment of a reversibly compressible endovascular device according to a fifth embodiment of the invention.
Figure 9B:
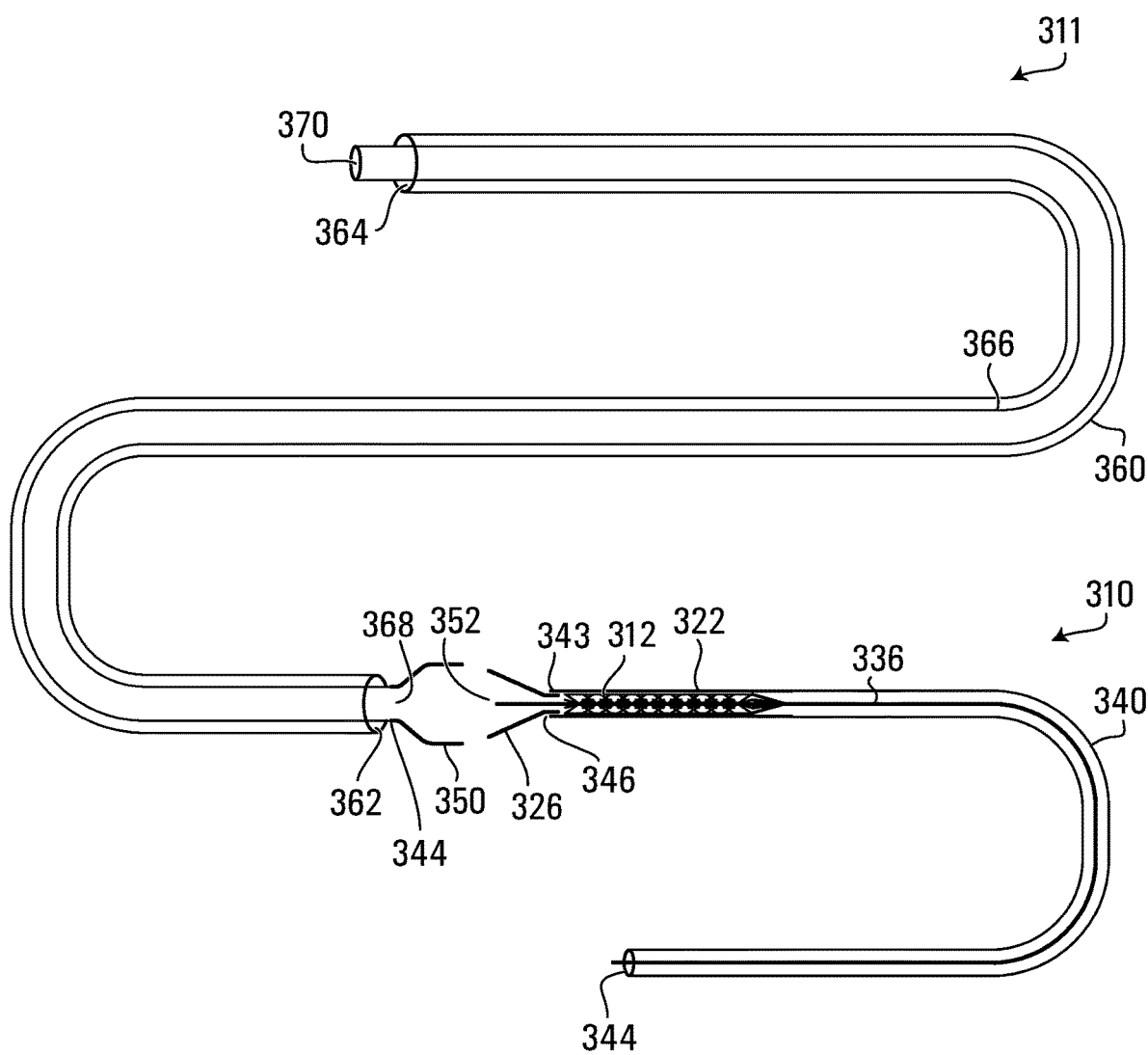
FIG. 9B is a drawing of a system for the deployment of a reversibly compressible endovascular device according to the embodiment illustrated in FIG. 9A, but with the endovascular device compressed within the delivery catheter.

Referring to FIGS. 9A and 9B, a system for deploying a reversibly compressible endovascular device within a lumen of a vessel is shown generally at 311. The system comprises a system for the radial compression of a reversibly compressible endovascular device (ED) prior to deployment as described above with reference to FIG. 8. The system further comprises a guide catheter 360 having proximal and distal guide catheter openings 362 and 364. Guide catheter 360 is for advancement in a vessel of a subject to a position wherein distal guide catheter opening 364 is proximal to a target site.

The system further comprises an intermediate catheter 366 comprising proximal and distal intermediate catheter openings 368 and 370. Intermediate catheter 366 is for advancement within guide catheter 360 to a position where distal intermediate catheter opening 370 is at the target site.

Delivery catheter 340 is for advancement within intermediate catheter 366 to a position where distal delivery catheter opening 346 is at the target site.

Push wire 336 is operable to be advanced through delivery catheter 340 to urge ED 312 distally from the delivery catheter and out distal delivery catheter opening 346.

Figure 9C:
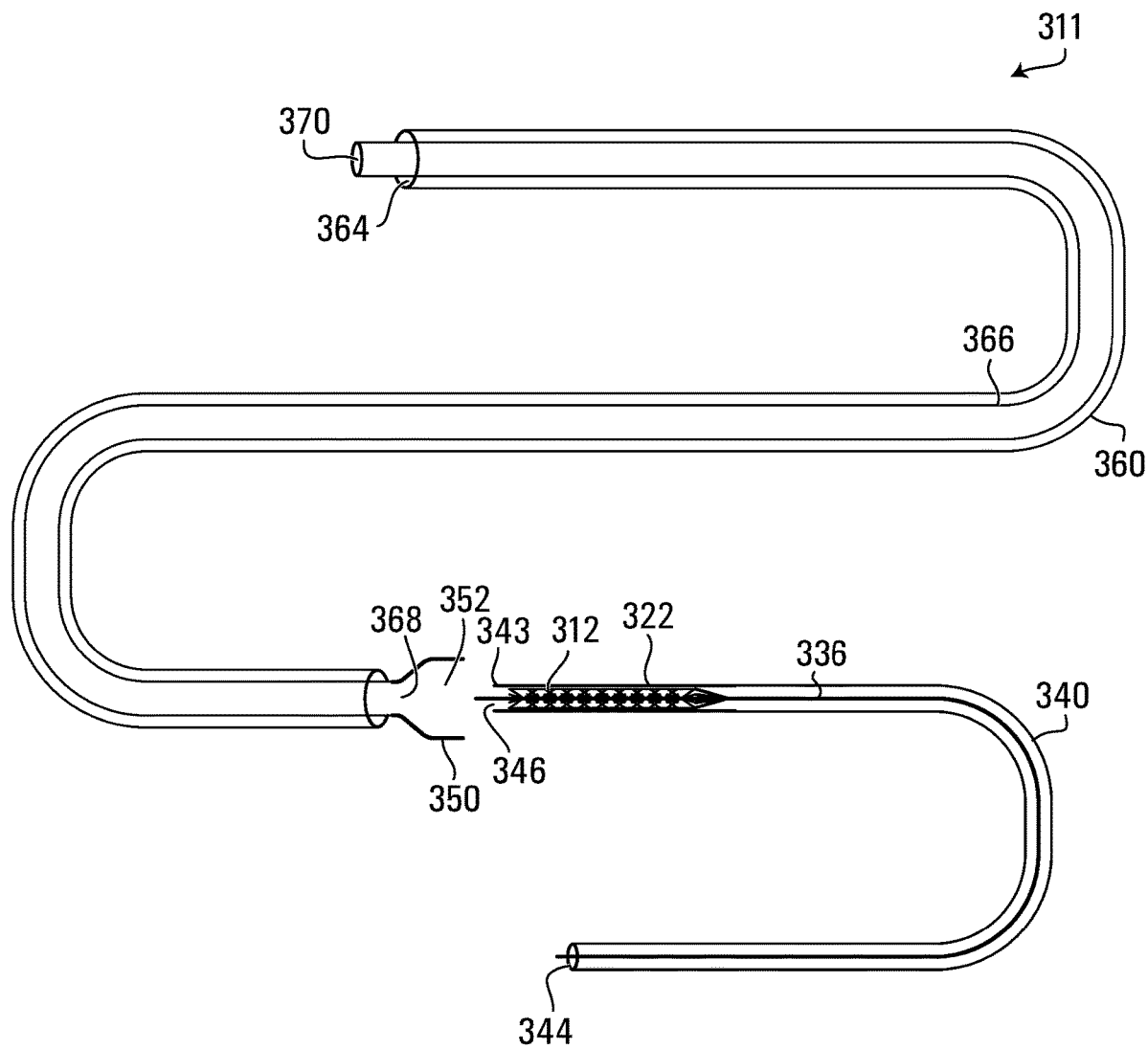
FIG. 9C is a drawing of a system for the deployment of a reversibly compressible endovascular device according to the embodiment illustrated in FIGS. 9A and 9B, but after the compressor has been removed.

In operation, guide catheter 360 and intermediate catheter 366 will typically be deployed in a vessel of a subject, such that distal guide catheter opening 364 and distal intermediate catheter opening 370 are positioned at the target site. Referring to-FIGS. 9A and 9B, ED 312 is loaded in delivery catheter 340 as described above. Referring to FIGS. 9B and 9C, compressor 326 may then be removed from system 310 prior to engaging loaded delivery catheter 340 with intermediate catheter 366.

Figure 9D:
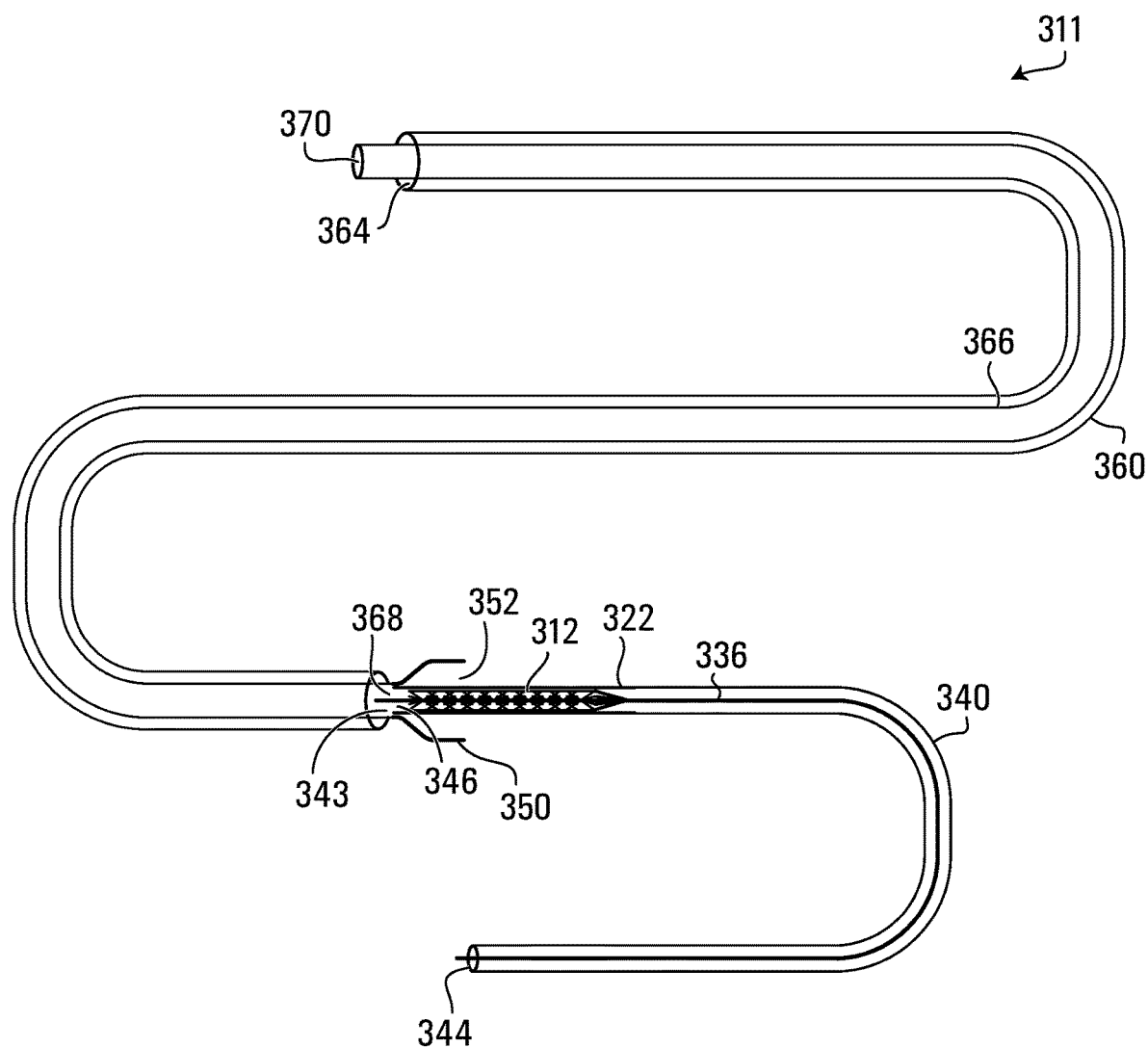
FIG. 9D is a drawing of a system for the deployment of a reversibly compressible endovascular device according to the embodiment illustrated in FIGS. 9A, 9B, and 9C, but with the delivery catheter inserted within the intermediate catheter through the hub opening.
Figure 9E:
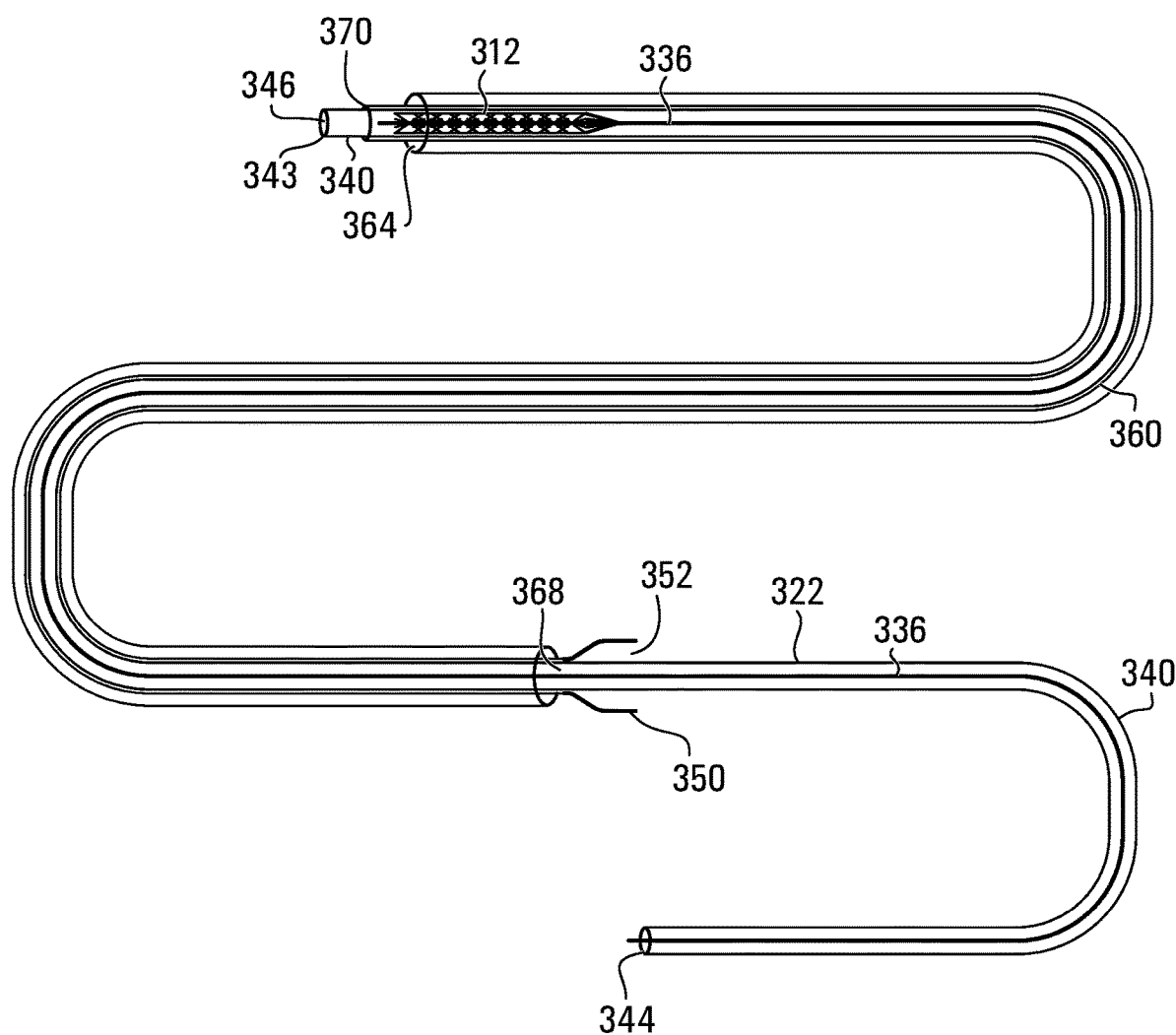
FIG. 9E is a drawing of a system for the deployment of a reversibly compressible endovascular device according to the embodiment illustrated in FIGS. 9A, 9B, 9C, and 9D, showing the delivery catheter with the compressed endovascular device at the distal delivery catheter end advanced to the distal intermediate catheter opening prior to deployment of the endovascular device at a target site within a lumen of a subject.
Figure 9F:
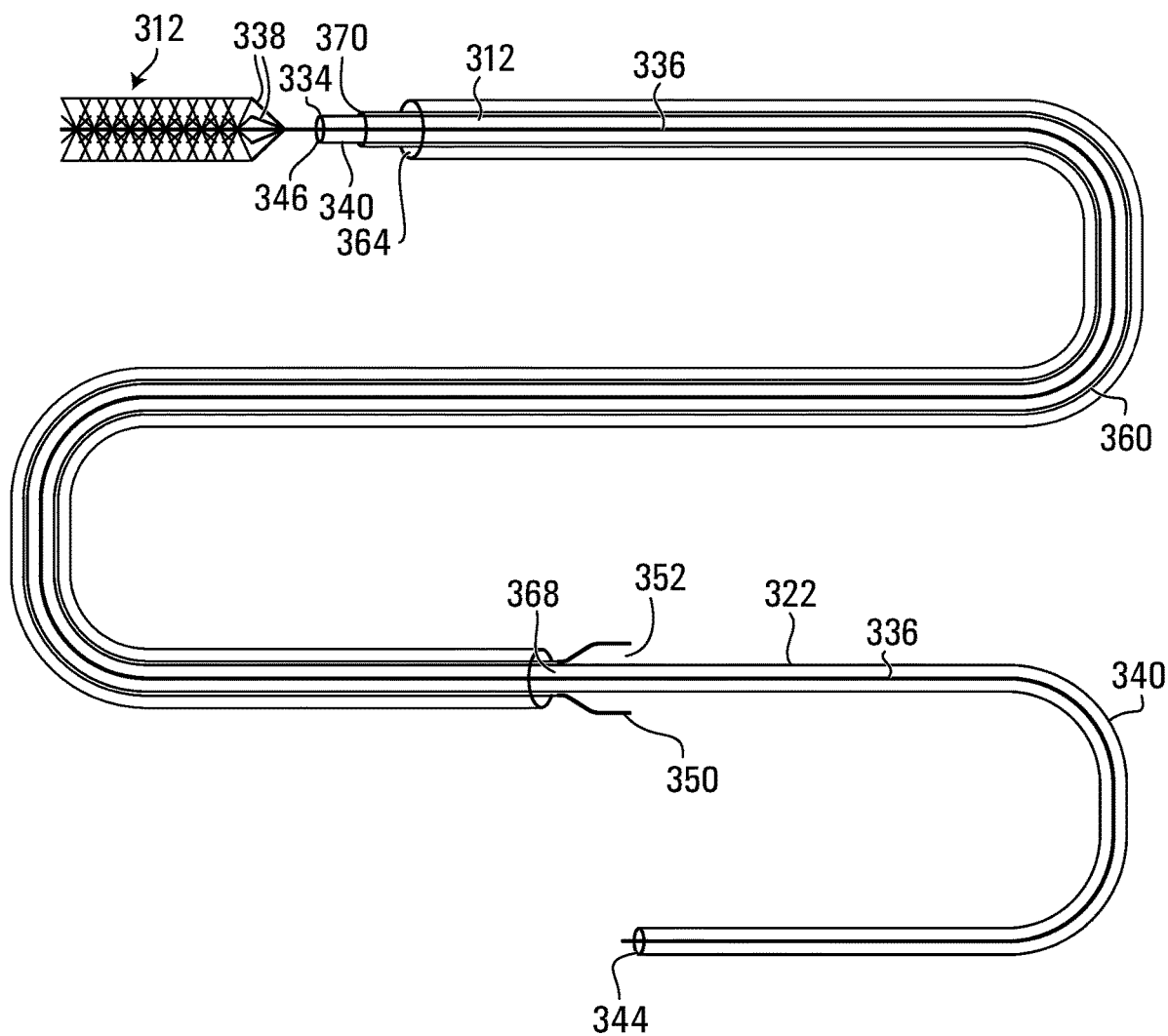
FIG. 9F is a drawing of a system for the deployment of a reversibly compressible endovascular device according to the embodiment illustrated in FIGS. 9A, 9B, 9C, 9D, and 9E showing the endovascular device advanced out of the distal opening of the delivery catheter and expanded at the target site within the lumen.

Referring to FIG. 9D, distal delivery catheter end 343, with ED 312 compressed within it, is then inserted in intermediate catheter 366 through proximal intermediate catheter opening 368. Referring to FIG. 9E, delivery catheter 340 is then advanced distally through intermediate catheter 366 until distal delivery catheter opening 346 is at the target site. Referring to FIG. 9F, push wire 336 is then used to advance ED 312 distally through distal delivery catheter opening 346 into the lumen of the vessel where it is expanded to its non-compressed position at the target site. Once in its non-compressed position at the target site, threads 338 are detached from ED 312. Delivery catheter 340 may then be removed, at which time a new delivery catheter, loaded with an ED, can be introduced.

In embodiments where the ED is a self-expanding ED, expanding ED 312 in the lumen involves allowing the ED to self-expand. It will be within the purview of a skilled person to select and employ an appropriate means of expanding an ED. For example, alternatives for expanding the ED may include inflating a balloon disposed within the tubular body of the ED to expand the ED.

While direct loading of a delivery catheter has been described above with regards to embodiments involving a non-collapsible compressor, the skilled person will readily understand that the embodiments involving a collapsible compressor as described with reference to FIGS. 3, 4A, 4B, and 5A to 5G, or a collapsible compressor and an ED that are moveable independent of each as described in FIGS. 6A, 6B, and 7A to 7D in connection with a delivery sheath could also be adapted for direct loading of an ED into the distal end of a delivery catheter.

The skilled person will also understand that, in some embodiments, an ED could be directly loaded into a delivery catheter through the proximal delivery catheter opening. That is, the compressor could be positioned in reversed orientation, i.e. such that it tapered from the proximal compressor end to the distal compressor end, to radially compress ED 312 for reception by the delivery catheter through proximal delivery catheter opening 344. In such embodiments, the distal compressor opening is in communication with the proximal delivery catheter opening 344. The width of the distal compressor opening would be smaller than the radial diameter of the ED 312 when the ED is in the non-compressed position. The radial cross sectional area of interior space at the distal compressor end, e.g. at the distal compressor opening, would equal to or less than the radial cross sectional area of proximal delivery catheter opening 344. In this way, as the ED is urged through the compressor, it would be compressed to have a radial cross section less than the radial cross section of the proximal delivery catheter opening 344, such that ED 312 could be received within delivery catheter in the compressed position. As such, the ED, in a compressed form, can be urged through distal compressor opening and received within the delivery catheter. The threads by which the push wire was attached to the ED may preferably be attached at the distal ED opening, such that advancing the push wire into the delivery catheter through the compressor would effectively pull the ED through the compressor. Alternatively, a pull wire extending through the distal delivery catheter opening, the delivery catheter, and the proximal delivery catheter, and attached to the ED at the distal ED opening, could be used to pull the ED through the compressor (thereby compressing the ED) and into the delivery catheter through the proximal delivery catheter opening. The pull wire could then be used to pull the ED through the delivery catheter to the distal catheter end. The pull wire is detachably attached to the ED such that, when the ED is at the distal delivery catheter end, the pull wire could be detached from the ED. The delivery catheter, with the ED loaded inside, could then be introduced to patient using, for example, a triaxial system as described above.

Operation

While specific embodiments of the invention have been described and illustrated, such embodiments should be considered illustrative of the invention only and not as limiting the invention as construed in accordance with the accompanying claims.

All documents referred to herein, including patent application publications, patents, and other publications are incorporated by reference in their entirety.

EMBODIMENTS

1. A system for the radial compression of a reversibly compressible endovascular device (ED) prior to deployment, the system comprising:
the ED, wherein the ED comprises a tubular body, wherein the body is expandable between a compressed position and an non-compressed position, the tubular body having an inner surface, an outer surface, and opposed distal and proximal ED openings;
a delivery sheath sized to receive and maintain the ED in the compressed position, the delivery sheath having a delivery sheath opening having a width sized to receive the ED into the delivery sheath in a compressed form;
a compressor for compressing the ED for reception by the delivery sheath through the delivery sheath opening, wherein the compressor comprises:
a generally tapered structure defining an interior space, the tapered structure comprising distal and proximal compressor ends, wherein the proximal compressor end is proximal to the delivery sheath opening, wherein the distal compressor end comprises a distal compressor opening sized to receive the ED in the non-compressed position, wherein the tapered structure tapers from the distal compressor opening toward the proximal compressor end such that the cross section of the interior space diminishes toward the proximal compressor end, wherein the cross sectional area of the interior space at the second end is equal to or less than the cross sectional area of the delivery sheath opening; and
a push wire detachably attached to the ED and disposed within the delivery sheath,
wherein the push wire is operable to be advanced proximally through the delivery sheath to urge the ED through the compressor, whereby the ED is deformed into the compressed position as it is urged proximally through the compressor.

2. The system of embodiment 1, wherein the compressor comprises a second compressor opening at the second compressor end.

3. The system of embodiment 2, wherein the second compressor opening is in communication with the delivery sheath opening 4. The system of embodiment 2 or 3, wherein the width of the second compressor opening is smaller than the radial diameter of the ED when the ED is in the non-compressed position.

5. The system of embodiment 2, 3, or 4, wherein the push wire is disposed within the ED through the second compressor opening.

6. The system of any one of embodiments 2 to 5, wherein the push wire is operable to be advanced proximally through the delivery sheath to urge the ED through the second compressor opening and into the delivery sheath.

7. The system of any one of embodiments 1 to 6, wherein the compressor is a funnel.

8. The system of any one of embodiments 1 to 7, wherein the tapered structure comprises a unitary body.

9. The system of any one of embodiments 1 to 8, wherein the push wire is detachably attached to the ED by one or more threads.

10. The system of embodiment 9, wherein the one or more threads are attached to the inner surface of the ED.

11. The system of 9 or 10, wherein the one or more threads are electrolytically detachable from the ED.

12. The system of embodiment 9 or 10, wherein the one or more threads is a single wire comprising a lasso looped around the tubular body at a proximal end of the ED.

13. The system of embodiment 9, 10, or 12, wherein the one or more threads are mechanically detachable from the ED.

14. The system of any one of embodiments 1 to 13, wherein the compressor is detachable.

15. The system of any one of embodiments 1 to 3, wherein the compressor is collapsible.

16. The system of any one of embodiments 1 to 3, wherein the compressor is reversibly collapsible.

17. The system of embodiment 15 or 16, wherein the compressor comprises a braided structure.

18. The system of embodiment 17, wherein the braided structure is a polypropylene braided structure.

19. The system of embodiment 17, wherein the braid structure is a metal braided structure.

20. The system of embodiment 15 or 16, wherein the tapered structure comprises a plurality of overlapping tongues coupled at the second compressor end, wherein each tongue tapers toward the second compressor end.

21. The system of embodiment 15, 16, or 20, wherein the second compressor end is sized to be received within the delivery sheath through the delivery sheath opening.

22. The system of embodiment 21, wherein the compressor is sized to be received within the delivery sheath when the compressor is in a collapsed position.

23. The system of embodiment 22, wherein an inner wall of the delivery sheath is operable to exert a force against the side of the tapered structure, as the compressor is received within the delivery sheath that is sufficient to collapse the compressor.

24. The system of any one of embodiments 14 to 23, wherein the push wire is attached to the compressor, wherein the compressor is attached to the ED by one or more threads.

25. The system of embodiment 24, wherein the one or more threads are attached to the inner surface of the ED.

26. The system of 24 or 25, wherein the one or more threads are electrolytically detachable from the ED.

27. The system of embodiment 24 or 25, wherein the one or more threads are mechanically detachable from the ED.

28. The system of embodiment 24 or 25, wherein the one or more threads is a single wire comprising a lasso looped around the tubular body at a proximal end of the ED.

29. The system of any one of embodiments 14 to 23, wherein the push wire is attached to the compressor, wherein an interior surface of the tapered structure is operable to frictionally engage the outer surface of the ED.

30. The system of any one of embodiments 14 to 29, wherein the push wire is operable to be advanced proximally through the delivery sheath to urge the ED and the compressor toward the delivery sheath, whereby collapse of the compressor upon reception within the delivery sheath exerts a radial force upon the ED sufficient to compress the ED for reception in the delivery sheath.

31. The system of any one of embodiments 14 to 23, wherein the push wire is detachably attached to the ED by one or more threads.

32. The system of embodiment 31, wherein the one or more threads are attached to the inner surface of the ED.

33. The system of embodiment 31 or 32, wherein the one or more threads are electrolytically detachable from the ED.

34. The system of embodiment 31 or 32, wherein the one or more threads is a single wire comprising a lasso looped around the tubular body at a proximal end of the ED.

35. The system of embodiment 31, 32, or 33, wherein the one or more wires are mechanically detachable from the ED.

36. The system of any one of embodiments 31 to 35, wherein an interior surface of the tapered structure is operable to frictionally engage the outer surface of the ED.

37. The system of any one of embodiments 31 to 36, further comprising a hollow compressor wire attached to the compressor and disposed within the delivery sheath, wherein the compressor wire is operable to be advanced through the delivery sheath to urge the compressor through the delivery sheath opening to collapse the compressor, whereby the ED is deformed into the compressed position as the compressor collapses as the ED and the compressor are urged through the delivery sheath opening.

38. The system of embodiment 37, wherein the push wire is disposed within the compressor wire, wherein the push wire is operable to be advanced through the delivery sheath independently of the compressor wire to urge the ED independently of the compressor.

39. The system of embodiment 37 or 38, further comprising a bump member disposed on the push wire between the ED and the compressor, wherein the bump member is for abutting the ED along the circumference of the proximal ED opening to urge the ED distally through the delivery sheath when the push wire is advanced distally through the delivery sheath.

40. The system of embodiment 37, 38, or 39, wherein the push wire and compressor wire are operable to be advanced proximally through the delivery sheath to urge the ED and the compressor toward the delivery sheath, whereby collapse of the compressor upon reception within the delivery sheath exerts a radial force upon the ED sufficient to compress the ED for reception in the delivery sheath.

41. The system of any one of embodiments 1 to 40, wherein the ED is a self-expanding ED.

42. A system for deploying a reversibly compressible endovascular device within a lumen of a vessel, the system comprising:
- a system for the radial compression of a reversibly compressible endovascular device (ED) prior to deployment as defined in any one of embodiments 1 to 41;
- a delivery catheter comprising proximal and distal delivery catheter openings, wherein the distal delivery catheter opening is for deploying the ED in to the lumen, and wherein the proximal delivery catheter opening is for receiving the ED from the delivery sheath, wherein the proximal delivery catheter opening is of a width equal to or greater than the width of the delivery sheath opening; and
- a hub connected to the proximal delivery catheter opening, the hub having a hub opening for receiving the delivery sheath in the hub when the ED is positioned in the delivery sheath, and positioning the delivery sheath in abutment with the proximal delivery catheter opening,
- wherein the push wire is operable to be advanced through the delivery catheter to urge the ED through the delivery catheter and out distal delivery catheter opening.

43. The system of embodiment 42, wherein the push wire is operable to be advanced through the delivery catheter to urge the compressor through the delivery catheter and out the distal delivery catheter opening, wherein the compressor is operable to expand.

44. The system of embodiment 42 or 43, wherein the push wire is operable to be retracted toward the hub to urge a deployed ED and expanded compressor toward the distal delivery catheter opening, whereby collapse of the compressor upon reception within the delivery catheter exerts a radial force upon the ED sufficient to compress the ED for reception in the delivery catheter.

45. A system for deploying a reversibly compressible endovascular device within a lumen of a vessel, the system comprising:
- a system for the radial compression of a reversibly compressible endovascular device (ED) prior to deployment as defined in any one of embodiments 37 to 41,
- a delivery catheter comprising proximal and distal delivery catheter openings, wherein the distal delivery catheter opening is for deploying the ED in to the lumen, and wherein the proximal delivery catheter opening is for receiving the ED from the delivery sheath, wherein the proximal delivery catheter opening is of a width equal to or greater than the width of the delivery sheath opening; and
- a hub connected to the proximal delivery catheter opening, the hub having a hub opening for receiving the delivery sheath in the hub when the ED is positioned in the delivery sheath, and positioning the delivery sheath in abutment with the proximal delivery catheter opening,
- wherein the push wire and compressor wire are operable to be advanced through the delivery catheter to urge the ED and the compressor through the delivery catheter and out distal delivery catheter opening, wherein the compressor is operable to expand.

46. The system of embodiment 45, wherein the push wire is operable to be retracted toward the hub to urge a deployed ED and expanded compressor toward the distal delivery catheter opening, whereby collapse of the compressor upon reception within the delivery catheter exerts a radial force upon the ED sufficient to compress the ED for reception in the delivery catheter.

47. A method of loading a reversibly compressible endovascular device (ED) into a delivery sheath having an interior width less than the radial width of the ED in an unexpanded position, the method comprising:
- compressing the ED from an expanded position to an unexpanded position for reception in the delivery sheath, wherein compressing comprises urging the ED in the expanded position through an interior space of a compressor, wherein the compressor comprises a tapered structure tapered from a distal compressor end toward a proximal compressor end of the tapered structure, wherein the width of the interior space at the distal compressor end is greater than the diameter of the ED in the expanded position and the width of the interior space at the proximal compressor end is less than the diameter of the ED in the expanded position, to radially compress the ED to an unexpanded position;
- urging the ED in the unexpanded position through a proximal compressor opening at the proximal compressor end and into the delivery sheath through a delivery sheath opening.

48. The method of embodiment 47, wherein the tapered structure is resiliently collapsible.

49. The method of embodiment 48, wherein the tapered structure comprises a plurality of overlapping tongues coupled at the proximal compressor end, wherein each tongue tapers toward the proximal compressor end.

50. The method of embodiment 49, wherein each tongue is slidable over an adjacent tongue to change the cross sectional area of the interior space.

51. A method of loading a reversibly compressible endovascular device (ED) into a delivery sheath having a width less than the ED in an unexpanded position, the method comprising:
- compressing the ED from an expanded position to an unexpanded position for reception in the delivery sheath, wherein compressing comprises collapsing a compressor, the compressor comprising a tapered structure having a wall defining an interior space in which the ED is positioned in the expanded position, wherein the wall exerts a radial force upon the ED to compress the ED, wherein the tapered structure is sized to be received in the delivery sheath when collapsed; and
- urging the compressor, with the ED positioned in the interior space in the unexpanded position, into the delivery sheath through a delivery sheath opening sized to receive the compressor in a collapsed position.

52. The method of embodiment 51, wherein collapsing the compressor comprises progressively reducing the radial cross sectional area of the interior space across the length of the tapered structure.

53. The method of embodiment 51 or 52, wherein the wall comprises a plurality of overlapping tongues coupled at a proximal end of the compressor, wherein each tongue tapers toward the proximal end of the compressor.

54. The method of embodiment 53, wherein the collapsing the compressor comprises sliding the overlapping tongues over each other to progressively reducing the radial cross sectional area of the interior space across the length of the tapered structure.

55. The method of any one of embodiments 51 to 54, further comprising frictionally engaging the ED with an interior surface of the wall to retain the ED in the interior space.

56. A method of deploying a reversibly compressible endovascular device in a vessel, the method comprising:
loading the ED in a delivery sheath according to a method as defined in any one of embodiments 47 to 55;
registering the delivery sheath opening with a proximal delivery catheter opening of a delivery catheter, wherein the delivery catheter is disposed within the vessel, and wherein a distal delivery catheter opening of the delivery catheter is at a target site in the vessel;
advancing the ED through the delivery sheath opening into the delivery catheter through the proximal delivery catheter opening, and through the delivery catheter toward a distal delivery catheter opening of the delivery catheter;
advancing the ED through the distal delivery catheter opening and into the lumen of the vessel at the target site; and
expanding the ED in the lumen at the target site.

57. The method of embodiment 56, wherein the ED is a self-expanding ED and expanding the ED in the lumen involves allowing the ED to self-expand in the lumen.

58. The method of embodiment 57, wherein expanding the ED within the lumen comprises inflating a balloon disposed within the tubular body to expand the ED.

59. The method of embodiment 56, 57, or 58, wherein the compressor is a reversibly collapsible compressor, the method further comprising advancing the reversibly collapsible compressor through the distal delivery catheter opening into the lumen, and expanding the compressor to an expanded position.

60. The method of embodiment 59, wherein the compressor is a self-expanding compressor.

61. The method of embodiment 59 or 60, further comprising:
positioning the expanded ED within the interior space of the expanded compressor; and
compressing the ED from the expanded position to an compressed position for reception in the delivery catheter, wherein compressing comprises collapsing the compressor, wherein the wall exerts a radial force upon the ED to compress the ED, wherein the tapered structure is sized to be received in the delivery catheter when collapsed; and
urging the compressor, with the ED positioned in the interior space in the compressed position, into the delivery catheter through the distal delivery catheter opening to receive the compressor in a collapsed position.

62. The method of embodiment 61, further comprising repositioning the delivery catheter in the lumen at a second position and advancing the ED through the distal delivery catheter opening into the lumen of the vessel, and expanding the ED in the lumen.

63. The method of embodiment 62, wherein the ED is a self-expanding ED, and wherein expanding the ED in the lumen involves allowing the ED to self-expand in the lumen.

64. The method of any one of embodiments 56 to 63, wherein the delivery catheter comprises a hub connected to the proximal delivery catheter opening and sized to receive the distal delivery sheath end, wherein registering the delivery sheath opening with the proximal deliver catheter opening comprises inserting the delivery sheath within the hub and abutting the delivery sheath opening to the proximal delivery catheter opening.

65. A system for the radial compression of a reversibly compressible endovascular device (ED) prior to deployment, the system comprising:
the ED, wherein the ED comprises a tubular body, wherein the body is self-expandable between a compressed position and an non-compressed position, the tubular body having an inner surface, an outer surface, and opposed distal and proximal ED openings;
a delivery catheter sized to receive and maintain the ED in the compressed position, the delivery catheter having proximal and distal delivery catheter ends, and a distal delivery catheter opening at the distal delivery catheter end, wherein the distal delivery catheter opening has a width sized to receive the ED into the delivery catheter in a compressed form;
a compressor for compressing the ED for reception by the delivery catheter through the distal delivery catheter opening, wherein the compressor comprises:
a generally tapered structure defining an interior space, the tapered structure comprising distal and proximal compressor ends, wherein the proximal compressor end is proximal to the distal delivery catheter opening, wherein the distal compressor end comprises a distal compressor opening sized to receive the ED in the non-compressed position, wherein the tapered structure tapers from the distal compressor end toward the proximal compressor end such that the cross section of the interior space diminishes toward the proximal end, wherein the cross sectional area of the interior space at the proximal compressor end is equal to or less than the cross sectional area of the distal delivery catheter opening; and
a push wire detachably attached to the ED and disposed within the delivery catheter,
wherein the push wire is operable to be advanced proximally through the delivery catheter toward the proximal delivery catheter end to urge the ED through the compressor, whereby the ED is deformed into the compressed position as it is urged through the compressor.

66. The system of embodiment 65, wherein the compressor comprises a proximal compressor opening at the proximal compressor end.

67. The system of embodiment 66, wherein the proximal compressor opening is in communication with the distal delivery catheter opening.

68. The system of embodiment 66 or 67, wherein the width of the proximal compressor opening is smaller than the radial diameter of the ED when the ED is in the non-compressed position.

69. The system of embodiment 66, 67, or 68, wherein the push wire is disposed within the ED through the proximal compressor opening.

70. The system of any one of embodiments 66 to 69, wherein the push wire is operable to be advanced proximally through the delivery catheter to urge the ED through the proximal compressor opening and into the delivery catheter.

71. The system of any one of embodiments 65 to 70, wherein the compressor is a funnel.

72. The system of any one of embodiments 65 to 71, wherein the tapered structure comprises a unitary body.

73. The system of any one of embodiments 65 to 72, wherein the push wire is detachably attached to the ED by one or more threads.

74. The system of embodiment 73, wherein the one or more threads are attached to the inner surface of the ED.

75. The system of 73 or 74, wherein the one or more threads are electrolytically detachable from the ED.

76. The system of embodiment 73 or 74, wherein the one or more threads is a single wire comprising a lasso looped around the tubular body at a proximal end of the ED.

77. The system of embodiment 73, 74, or 75, wherein the one or more threads are mechanically detachable from the ED.

78. The system of any one of embodiments 65 to 77, wherein the compressor is detachable.

79. The system of any one of embodiments 65 to 68, wherein the compressor is collapsible.

80. The system of any one of embodiments 65 to 67, wherein the compressor is reversibly collapsible.

81. The system of embodiment 79 or 80, wherein the compressor comprises a braided structure.

82. The system of embodiment 81, wherein the braided structure is a polypropylene braided structure.

83. The system of embodiment 81, wherein the braid structure is a metal braided structure.

84. The system of embodiment 76 or 77, wherein the tapered structure comprises a plurality of overlapping tongues coupled at the proximal compressor end, wherein each tongue tapers toward the proximal compressor end.

85. The system of embodiment 79, 80, or 84, wherein the proximal compressor end is sized to be received within the delivery catheter through the distal delivery catheter opening.

86. The system of embodiment 85, wherein the compressor is sized to be received within the delivery catheter when the compressor is in a collapsed position.

87. The system of embodiment 86, wherein an inner wall of the delivery catheter is operable to exert a force against the side of the tapered structure, as the compressor is received within the delivery catheter, that is sufficient to collapse the compressor.

88. The system of any one of embodiments 78 to 87, wherein the push wire is attached to the compressor, wherein the compressor is attached to the ED by one or more threads.

89. The system of embodiment 88, wherein the one or more threads are attached to the inner surface of the ED.

90. The system of 88 or 89, wherein the one or more wires are electrolytically detachable from the ED.

91. The system of embodiment 88 or 89, wherein the one or more wires are mechanically detachable from the ED.

92. The system of embodiment 88 or 89, wherein the one or more threads is a single wire comprising a lasso looped around the tubular body at a proximal end of the ED.

93. The system of any one of embodiments 78 to 87, wherein the push wire is attached to the compressor, wherein an interior surface of the tapered structure is operable to frictionally engage the outer surface of the ED.

94. The system of any one of embodiments 78 to 93, wherein the push wire is operable to be advanced through the delivery catheter to urge the ED and the compressor toward the distal delivery catheter opening, whereby collapse of the compressor upon reception within the delivery catheter exerts a radial force upon the ED sufficient to compress the ED for reception in the delivery catheter.

95. The system of any one of embodiments 78 to 87, wherein the push wire is detachably attached to the ED by one or more threads.

96. The system of embodiment 95, wherein the one or more threads are attached to the inner surface of the ED.

97. The system of 95 or 96, wherein the one or more threads are electrolytically detachable from the ED.

98. The system of embodiment 85 or 96, wherein the one or more threads is a single wire comprising a lasso looped around the tubular body at a proximal end of the ED.

99. The system of embodiment 95, 96, or 98, wherein the one or more threads are mechanically detachable from the ED.

100. The system of any one of embodiments 89 to 93, wherein an interior surface of the tapered structure is operable to frictionally engage the outer surface of the ED.

101. The system of any one of embodiments 96 to 100, further comprising a hollow compressor wire attached to the compressor and disposed within the delivery catheter, wherein the compressor wire is operable to be advanced through the delivery catheter to urge the compressor through the distal delivery catheter opening, whereby the ED is deformed into the compressed position as it is urged through the compressor.

102. The system of embodiment 101, wherein the push wire is disposed within the compressor wire, wherein the push wire is operable to be advanced through the delivery catheter independently of the compressor wire to urge the ED independently of the compressor.

103. The system of embodiment 100, 101, or 102, further comprising a bump member disposed on the push wire between the ED and the compressor, wherein the bump member is for abutting the ED along the circumference of the proximal ED opening to urge the ED distally through the delivery sheath when the push wire is advanced distally through the delivery sheath.

104. The system of embodiment 101, 102, or 103, wherein the push wire and compressor wire are operable to be advanced proximally through the delivery catheter to urge the ED and the compressor toward the delivery catheter, whereby collapse of the compressor upon reception within the delivery catheter exerts a radial force upon the ED sufficient to compress the ED for reception in the delivery sheath.

105. The system of any one of embodiments 62 to 104, wherein the ED is a self-expanding ED.

106. A system for deploying a reversibly compressible endovascular device within a lumen of a vessel of a patient, the system comprising:
a system for the radial compression of a reversibly compressible endovascular device (ED) prior to deployment as defined in any one of embodiments 65 to 105;
a guide catheter comprising proximal and distal guide catheter openings, wherein the distal guide catheter opening is for positioning at a target site in the lumen, and wherein the proximal guide catheter opening is for receiving the delivery catheter external to the patient, wherein the proximal guide catheter opening is of a width greater than the width of the delivery catheter;
wherein the delivery catheter is operable to be inserted in the guide catheter through the proximal guide catheter opening and advanced through the guide catheter and out the distal guide catheter opening at the target site, wherein the push wire is operable to be advanced through the delivery catheter to urge the ED through the delivery catheter and out distal delivery catheter, wherein the ED is operable to expand.

107. The system of embodiment 106, wherein push wire is operable to be advanced through the delivery catheter to urge the compressor through the delivery catheter and out distal delivery catheter opening, wherein the compressor is operable to expand.

108. The system of embodiment 107, wherein the push wire is operable to be retracted proximally to urge a deployed ED and expanded compressor toward the distal delivery catheter opening, whereby collapse of the compressor upon reception within the delivery catheter exerts a radial force upon the ED sufficient to compress the ED for reception in the delivery catheter.

109. A system for deploying a reversibly compressible endovascular device within a lumen of a vessel of a patient, the system comprising:
   a system for the radial compression of a reversibly compressible endovascular device (ED) prior to deployment as defined in any one of embodiments 101 to 105;
   a guide catheter comprising proximal and distal guide catheter openings, wherein the distal guide catheter opening is for positioning at a target site in the lumen, and wherein the proximal guide catheter opening is for receiving the delivery catheter external to the patient, wherein the proximal guide catheter opening is of a width greater than the width of the delivery catheter; and
   wherein the push wire and compressor wire are operable to be advanced through the delivery catheter to urge the ED and the compressor through the delivery catheter and out distal delivery catheter opening, wherein the compressor is operable to expand.

110. The system of embodiment 109, wherein the push wire and compressor wire are operable to be retracted proximally to urge a deployed ED and expanded compressor toward the distal delivery catheter opening, whereby collapse of the compressor upon reception within the delivery catheter exerts a radial force upon the ED sufficient to compress the ED for reception in the delivery catheter.

111. A method of loading a reversibly compressible endovascular device (ED) into a delivery catheter having an interior width less than the radial width of the ED in an unexpanded position, the method comprising:
   compressing the ED from an expanded position to an unexpanded position for reception in the delivery catheter, wherein compressing comprises urging the ED in the expanded position through an interior space of a compressor, wherein the compressor comprises a tapered structure tapered from a distal compressor end toward a proximal compressor end, wherein the width of the interior space at the distal compressor end is greater than the diameter of the ED in the expanded position and the width of the interior space at the proximal compressor end is less than the diameter of the ED in the expanded position, to radially compress the ED to an unexpanded position;
   urging the ED in the unexpanded position through a proximal compressor opening at the proximal compressor end and into the delivery catheter through a distal delivery catheter opening.

112. The method of embodiment 111, wherein the tapered structure is resiliently collapsible.

113. The method of embodiment 111 or 112, wherein the tapered structure comprises a plurality of overlapping tongues coupled at the proximal compressor end, wherein each tongue tapers toward the second compressor end.

114. The method of embodiment 113, wherein each tongue is slidable over an adjacent tongue to change the cross sectional area of the interior space.

115. A method of loading a reversibly compressible endovascular device (ED) into a delivery sheath having a width less than the ED in an unexpanded position, the method comprising:
   compressing the ED from an expanded position to an unexpanded position for reception in the delivery catheter, wherein compressing comprises collapsing a compressor, the compressor comprising a tapered structure having a wall defining an interior space in which the ED is positioned in the expanded position, wherein the wall exerts a radial force upon the ED to compress the ED, wherein the tapered structure is sized to be received in the delivery catheter when collapsed; and
   urging the compressor, with the ED positioned in the interior space in the unexpanded position, into the delivery catheter through a distal delivery catheter opening sized to receive the compressor in a collapsed position.

116. The method of embodiment 115, wherein collapsing the compressor comprises progressively reducing the radial cross sectional area of the interior space across the length of the tapered structure.

117. The method of embodiment 115 or 116, wherein the wall comprises a plurality of overlapping tongues coupled at a proximal compressor end of the compressor proximal to the distal delivery catheter opening, wherein each tongue tapers toward the proximal compressor end.

118. The method of embodiment 117, wherein the collapsing the compressor comprises sliding the overlapping tongues over each other to progressively reducing the radial cross sectional area of the interior space across the length of the tapered structure.

119. The method of any one of embodiments 115 to 118, further comprising frictionally engaging the ED with an interior surface of the wall to retain the ED in the interior space.

120. A method of deploying a reversibly compressible endovascular device in a vessel, the method comprising:
   loading the ED in a delivery catheter according to a method as defined in any one of embodiments 111 to 119;
   advancing the delivery catheter through a guide catheter disposed within the vessel, wherein the guide catheter has a distal guide catheter opening positioned at a target site in the vessel, to position the distal delivery catheter opening at the target site;
   advancing the ED through the distal delivery catheter opening into the lumen of the vessel at a first position; and
   expanding the ED in the lumen.

121. The method of embodiment 120, wherein the ED is a self-expanding ED and expanding the ED in the lumen involves allowing the ED to self-expand in the lumen.

122. The method of embodiment 121, wherein expanding the ED within the lumen comprises inflating a balloon disposed within the tubular body to expand the ED.

123. The method of embodiment 120, 121, or 122, wherein the compressor is a reversibly collapsible compressor, wherein the method further comprises advancing the reversibly collapsible compressor through the distal delivery catheter opening and into the lumen, and expanding the compressor to an expanded position.

124. The method of embodiment 123, wherein the compressor is a self-expanding compressor.

125. The method of embodiment 123 or 124, further comprising:

positioning the expanded ED within the interior space of the expanded compressor; and compressing the ED from the expanded position to a compressed position for reception in the delivery catheter, wherein compressing comprises collapsing the compressor, wherein the wall exerts a radial force upon the ED to compress the ED, wherein the tapered structure is sized to be received in the delivery catheter when in a collapsed form; and urging the compressor, with the ED positioned in the interior space in the compressed position, into the delivery catheter through the distal delivery catheter opening to receive the compressor in a collapsed position.

126. The method of embodiment 125, further comprising repositioning the delivery catheter in the lumen at a second position and advancing the ED through the distal delivery catheter opening into the lumen of the vessel, and expanding the ED in the lumen at the second position.

127. The method of embodiment 126, wherein the ED is a self-expanding ED, and wherein expanding the ED in the lumen involves allowing the ED to self-expand in the lumen.

The invention claimed is:

1. A system for the radial compression of a reversibly compressible endovascular device (ED) prior to deployment, the system comprising:

the ED, wherein the ED comprises a tubular body, wherein the body is expandable between a compressed position and a non-compressed position, the tubular body having an inner surface, an outer surface, opposed distal and proximal ED ends, and opposed distal and proximal ED openings;

a delivery sheath sized to receive and maintain the ED in the compressed position, the delivery sheath having a delivery sheath opening having a diameter sized to receive the ED into the delivery sheath in a compressed form;

a collapsible compressor for compressing the ED for reception by the delivery sheath through the delivery sheath opening, wherein the compressor comprises a generally tapered structure defining an interior space, the tapered structure comprising distal and proximal compressor ends, wherein the proximal compressor end is proximal to the delivery sheath opening, wherein the distal compressor end comprises a distal compressor opening sized to receive the ED in the non-compressed position, wherein the tapered structure tapers from the distal compressor opening toward the proximal compressor end such that the cross section of the interior space diminishes toward the proximal compressor end, wherein the cross sectional area of the interior space at the proximal compressor end is equal to or less than the cross sectional area of the delivery sheath opening, and wherein an interior surface of the tapered structure is frictionally engaged with the outer surface of the ED;

a hollow compressor tube attached to the compressor and disposed within the delivery sheath, wherein the hollow compressor tube is operable to be advanced proximally through the delivery sheath to urge the compressor and the ED frictionally engaged therein through the delivery sheath opening to collapse the compressor, wherein collapse of the compressor upon reception within the delivery sheath exerts a radial force upon the ED sufficient to compress the ED into the compressed position for reception in the delivery sheath; and a push wire disposed within the hollow compressor tube and operable to be advanced through the delivery sheath independently of the hollow compressor tube, wherein the push wire has a bump member disposed thereon proximal to the proximal ED end, wherein the bump member comprises a circular contact surface having a diameter sized to contact the ED at the proximal ED end about a circumference of the proximal ED end of the ED in the compressed position, the bump member being configured so that a distal face of the bump member contacts the ED at the proximal ED end, wherein the bump member is not required to be engaged with the ED during compression by the collapsible compressor, and wherein the bump member is configured to be advanced distally relative to the tapered structure in order for the contact surface to contact the proximal ED end and apply a distal force at the proximal ED end about the circumference of the proximal ED end only in a distal direction in order for the ED to be disengaged from the compressor.

2. The system of claim 1, wherein the compressor comprises a proximal compressor opening at the proximal compressor end, wherein the proximal compressor opening is in communication with the hollow compressor tube.

3. The system of claim 2, wherein the width of the proximal compressor opening is smaller than the radial diameter of the ED when the ED is in the non-compressed position.

4. The system of claim 2, wherein the push wire is disposed within the ED through the proximal compressor opening, and wherein the push wire is operable to be advanced proximally through the delivery sheath.

5. The system of claim 1, wherein the compressor is at least one of a funnel or is reversibly collapsible.

6. The system of claim 1, wherein the compressor comprises a braided structure.

7. The system of claim 6, wherein the braided structure is a polypropylene braided structure or a metal braided structure.

8. The system of claim 1, wherein the tapered structure comprises a plurality of overlapping tongues coupled at the proximal compressor end, wherein each tongue tapers toward the proximal compressor end.

9. The system of claim 1, wherein the proximal compressor end is sized to be received within the delivery sheath through the delivery sheath opening.

10. The system of claim 9, wherein the compressor is sized to be received within the delivery sheath when the compressor is in a collapsed position.

11. The system of claim 1, wherein the ED is a self-expanding ED.

12. A system for deploying a reversibly compressible endovascular device within a lumen of a vessel, the system comprising:

a system for the radial compression of a reversibly compressible endovascular device (ED) prior to deployment as defined in claim 1;

a delivery catheter comprising proximal and distal delivery catheter openings, wherein the distal delivery catheter opening is for deploying the ED in to the lumen, and wherein the proximal delivery catheter opening is for receiving the ED from the delivery sheath, wherein the proximal delivery catheter opening is of a width equal to or greater than the width of the delivery sheath opening; and a hub connected to the proximal delivery catheter opening, the hub having a hub opening for receiving the delivery sheath in the hub when the ED is positioned in the delivery sheath, and positioning the delivery sheath in abutment with the proximal delivery catheter opening, wherein the push wire is operable to be advanced through the delivery catheter to urge the ED through the delivery catheter and out of the distal delivery catheter opening.

13. A system for the radial compression of a reversibly compressible endovascular device (ED) prior to deployment, the system comprising:

the ED, wherein the ED comprises a tubular body, wherein the body is self-expandable between a compressed position and a non-compressed position, the tubular body having an inner surface, an outer surface, opposed distal and proximal ED ends, and opposed distal and proximal ED openings;

a delivery catheter sized to receive and maintain the ED in the compressed position, the delivery catheter having proximal and distal delivery catheter ends, and a distal delivery catheter opening at the distal delivery catheter end, wherein the distal delivery catheter opening has a diameter sized to receive the ED into the delivery catheter in a compressed form;

a collapsible compressor for compressing the ED for reception by the delivery catheter through the distal delivery catheter opening, wherein the compressor comprises a generally tapered structure defining an interior space, the tapered structure comprising distal and proximal compressor ends, wherein the proximal compressor end is proximal to the distal delivery catheter opening, wherein the distal compressor end comprises a distal compressor opening sized to receive the ED in the non-compressed position, wherein the tapered structure tapers from the distal compressor end toward the proximal compressor end such that the cross section of the interior space diminishes toward the proximal compressor end, wherein the cross sectional area of the interior space at the proximal compressor end is equal to or less than the cross sectional area of the distal delivery catheter opening, and wherein an interior surface of the tapered structure is frictionally engaged with the outer surface of the ED;

a hollow compressor tube attached to the compressor and disposed within the delivery catheter, wherein the hollow compressor tube is operable to be advanced proximally through the delivery catheter toward the proximal delivery catheter end to urge the compressor and the ED frictionally engaged therein through the distal delivery catheter opening, wherein collapse of the compressor upon reception within the delivery catheter exerts a radial force upon the ED sufficient to compress the ED into the compressed position for reception in the delivery catheter; and a push wire disposed within the hollow compressor tube and operable to be advanced through the delivery catheter independently of the hollow compressor tube, wherein the push wire has a bump member disposed thereon proximal to the proximal ED end, wherein the bump member comprises a circular contact surface having a diameter sized to contact the ED at a proximal ED end about a circumference of the proximal ED end of the ED in the compressed position, the bump member being configured so that a distal face of the bump member contacts the ED at the proximal ED end, wherein the bump member is not required to be engaged with the ED during compression by the collapsible compressor, and wherein the bump member is configured to be advanced distally relative to the tapered structure in order for the contact surface to contact the proximal ED end and apply a distal force at the proximal ED end about the circumference of the proximal ED end only in a distal direction in order for the ED to be disengaged from the compressor.

14. The system of claim 13, wherein the compressor comprises a proximal compressor opening at the proximal compressor end, wherein the proximal compressor opening is in communication with the hollow compressor tube.

15. The system of claim 14, wherein the width of the proximal compressor opening is smaller than the radial diameter of the ED when the ED is in the non-compressed position.

16. The system of claim 14, wherein the push wire is disposed within the ED through the proximal compressor opening, and wherein the push wire is operable to be advanced proximally through the delivery catheter.

17. The system of claim 13, wherein the compressor is a funnel, comprises a braided structure, or is reversibly collapsible.

18. The system of claim 13, wherein the compressor comprises a polypropylene braided structure or a metal braided structure.

19. The system of claim 13, wherein the tapered structure comprises a plurality of overlapping tongues coupled at the proximal compressor end, and wherein each tongue tapers toward the proximal compressor end.

20. The system of claim 13, wherein the proximal compressor end is sized to be received within the delivery catheter through the distal delivery catheter opening.

21. The system of claim 20, wherein the compressor is sized to be received within the delivery catheter when the compressor is in a collapsed position.

22. The system of claim 13, wherein the ED is a self-expanding ED.

* * * * *